US011833209B2

(12) United States Patent
Stover et al.

(10) Patent No.: US 11,833,209 B2
(45) Date of Patent: Dec. 5, 2023

(54) FORMULATED AND/OR CO-FORMULATED LIPOSOME COMPOSITIONS CONTAINING PD-1 ANTAGONIST PRODRUGS USEFUL IN THE TREATMENT OF CANCER AND METHODS THEREOF

(71) Applicant: Nammi Therapeutics, Inc., Los Angeles, CA (US)

(72) Inventors: David Stover, Encino, CA (US); Dhruba Bharali, Sherman Oaks, CA (US); Bruce A Hay, Niskayuna, NY (US); Tahmineh Safaie, Los Angeles, CA (US)

(73) Assignee: Nammi Therapeutics, Inc., Los Angeles, CA (US)

( * ) Notice: Subject to any disclaimer, the term of this patent is extended or adjusted under 35 U.S.C. 154(b) by 137 days.

(21) Appl. No.: 17/300,655

(22) Filed: Sep. 10, 2021

(65) Prior Publication Data

US 2022/0080051 A1    Mar. 17, 2022

Related U.S. Application Data

(60) Provisional application No. 63/204,101, filed on Sep. 11, 2020.

(51) Int. Cl.
*A61K 47/54* (2017.01)
*A61K 47/69* (2017.01)
*A61P 35/00* (2006.01)

(52) U.S. Cl.
CPC .......... *A61K 47/554* (2017.08); *A61K 47/548* (2017.08); *A61K 47/549* (2017.08); *A61K 47/6911* (2017.08); *A61K 47/6929* (2017.08); *A61P 35/00* (2018.01)

(58) Field of Classification Search
CPC .. A61K 47/554; A61K 47/548; A61K 47/549; A61K 47/6911; A61K 47/6929; A61P 35/00
See application file for complete search history.

(56) References Cited

U.S. PATENT DOCUMENTS

| | | | |
|---|---|---|---|
| 8,232,313 | B2 | 7/2012 | Munn et al. |
| 9,732,035 | B2 | 8/2017 | Mautino et al. |
| 9,850,225 | B2 | 12/2017 | Chupak et al. |
| 9,872,852 | B2 | 1/2018 | Chupak et al. |
| 10,144,706 | B2 | 12/2018 | Yeung et al. |
| 10,308,644 | B2 | 6/2019 | Wu et al. |
| 10,639,284 | B2 | 5/2020 | Lange et al. |
| 10,806,785 | B2 | 10/2020 | Lu et al. |
| 10,882,844 | B2 | 1/2021 | Yeung et al. |
| 11,046,675 | B2 | 6/2021 | Yeung et al. |
| 11,246,877 | B2 | 2/2022 | Lin et al. |
| 2011/0178164 | A1 | 7/2011 | Cunha Dias Real Oliveira et al. |
| 2018/0065917 | A1 | 3/2018 | Webber et al. |
| 2018/0177870 | A1 | 6/2018 | Liu et al. |
| 2018/0179202 | A1 | 6/2018 | Wu et al. |
| 2018/0214563 | A1 | 8/2018 | Li et al. |
| 2018/0305315 | A1 | 10/2018 | Aktoudianakis et al. |
| 2019/0016681 | A1 | 1/2019 | Domling |
| 2020/0061030 | A1 | 2/2020 | Sasikumar et al. |
| 2021/0369862 | A1 | 12/2021 | De Smedt et al. |

FOREIGN PATENT DOCUMENTS

| | | | |
|---|---|---|---|
| WO | WO 2017/006227 A1 | 1/2017 | |
| WO | WO 2018/213631 A1 | 11/2018 | |

OTHER PUBLICATIONS

Kohli, et. al., Designer Lipids for Drug Delivery: From Heads to Tails, J. Control Release, (Sep. 28, 2014). 0; pp. 274-287, Author Manuscript.
Konstantinidou, et. al., Immune Checkpoint PD-1/PD-L1: Is There Life Beyond Antibodies?, Agnew. Chem. Int. Ed. (2018), 57; pp. 4840-4848.
Garcia-Pinel, et. al., Lipid-Based Nanoparticles: Application and Recent Advances in Cancer Treatment, Nanomaterials (2019), 9, 623, pp. 1-23.
Akbarzadeh, et. al., Liposome: Classification, Preparation, and Applications, Nanoscale Research Letters, (2013), 8:102 (pp. 1-9).
Skalniak, et. al., Small-Molecule Inhibitors of PD-1/PD-L1 Immune Checkpoint Alleviate the PD-L1 Induced Exhaustion . . . , Oncotarget, (2017), vol. 8, (No. 42), pp. 72167-72181.
Wang, et. al., Development of Inhibitors of the Programmed Cell Death-1/Programmed Cell Death-Ligand 1 Signaling Pathway, J. Med. Chem. (2019), 62, pp. 1715-1730.
Soremekun, et. al., Recruiting Monomer for Dimer Formation: Resolving the Antagonistic Mechanisms of Novel Immune . . . , Immunotherapy, Mol. Simulation, 45:10, pp. 777-789.
Zhong, et. al., The Characteristics of PD-L1 Inhibitors, from Peptides to Small Molecules, Molecules (2019), 24, 1940, pp. 1-17.
Dabkowska, et. al., The Effect of Neutral Helper Lipids on the Structure of Cationic Lipid Monolayers, J.R. Soc. Interface (2012), 9, pp. 548-561.
Mochizuki, et. al., The Role of Helper Lipid Dioleoylphosphatidylethanolamine (DOPE) for DNA Transfection . . . , Biochimica et. Biophysica Acta 1828 (2013) pp. 412-418.
Ojeda, et. al., The Role of Helper Lipids in the Intracellular Disposition and Transfection Efficiency of Niosome Formulations . . . , Int. J. Pharm., 503(1-2), pp. 115-126 (2016).
Smith, et. al., Therapeutic Targeting of Immune Checkpoints with Small Molecule Inhibitors, Am. J. Transl. Res., (2019); 11(2):529-541.

(Continued)

Primary Examiner — Robert S Cabral
(74) Attorney, Agent, or Firm — LOSMP; Shane M. Popp

(57) ABSTRACT

Formulated and/or co-formulated nanocarriers (e.g., LNPs and/or SLNPs) comprising PD-1 Prodrugs and methods of making the nanocarriers are disclosed herein. The PD-1 Prodrug compositions comprise a drug moiety, a lipid moiety, and linkage unit that inhibit PD-1-L1/L2. The PD-1 Prodrugs can be formulated and/or co-formulated into a nanocarrier to provide a method of treating cancer, immunological disorders, and other disease by utilizing a targeted drug delivery vehicle.

15 Claims, 23 Drawing Sheets

(56) References Cited

OTHER PUBLICATIONS

Gu, et. al., Undo the Brake of Tumour Immune Tolerance with Antibodies, Peptide Mimetrics and Small Molecule Compounds . . . , Clin. Exp. Pharmacol Physiol, (2019); 46:105-115.

Wang, et. al., Programmed Death-Ligand 1 Monoclonal Antibody-Linked Immunoliposomes for Synergistic Efficiacy . . . , Nanomedicine (Lond.) (2019), 14(13), pp. 1729-1744.

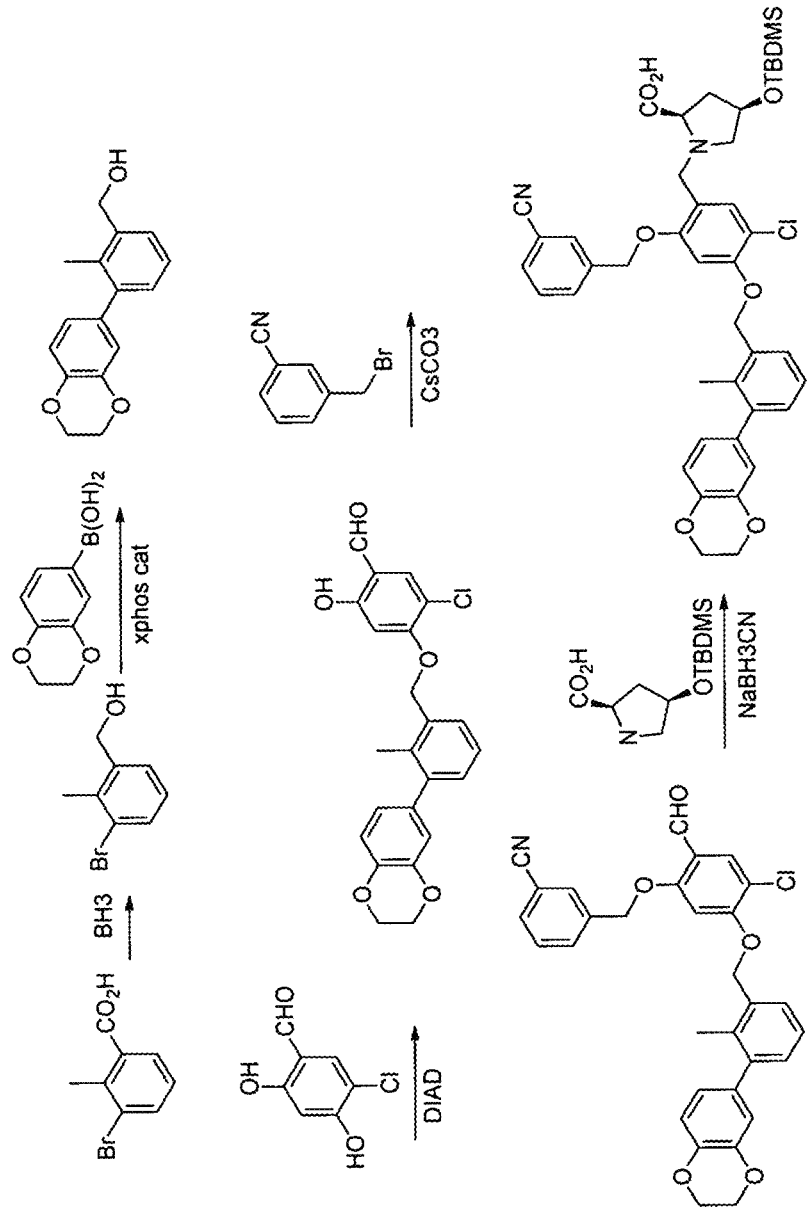
Figure 1. Chemical Synthesis for Protected PD3-Prodrug

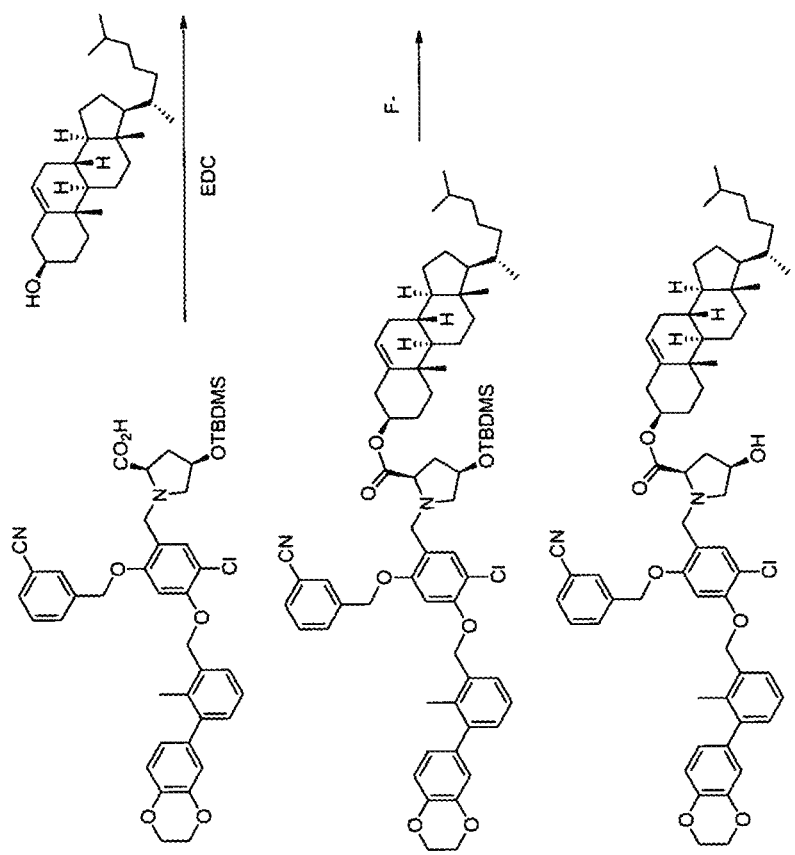
Figure 2. Chemical Synthesis for Protected PD3-Prodrug, continued

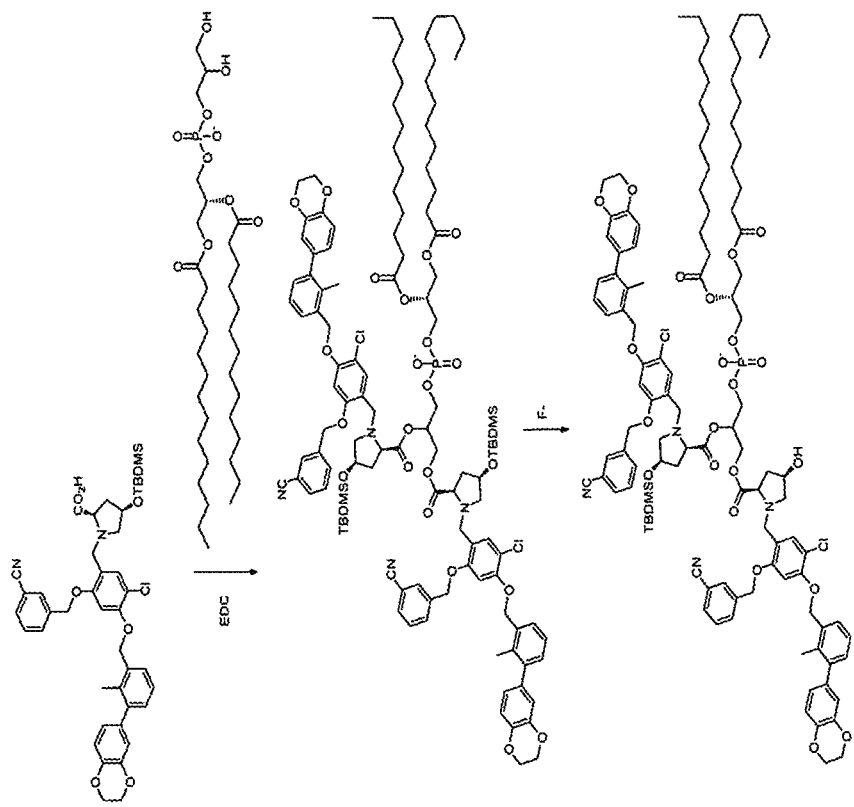
Figure 3. Chemical Synthesis for Protected PD3-Prodrug, continued

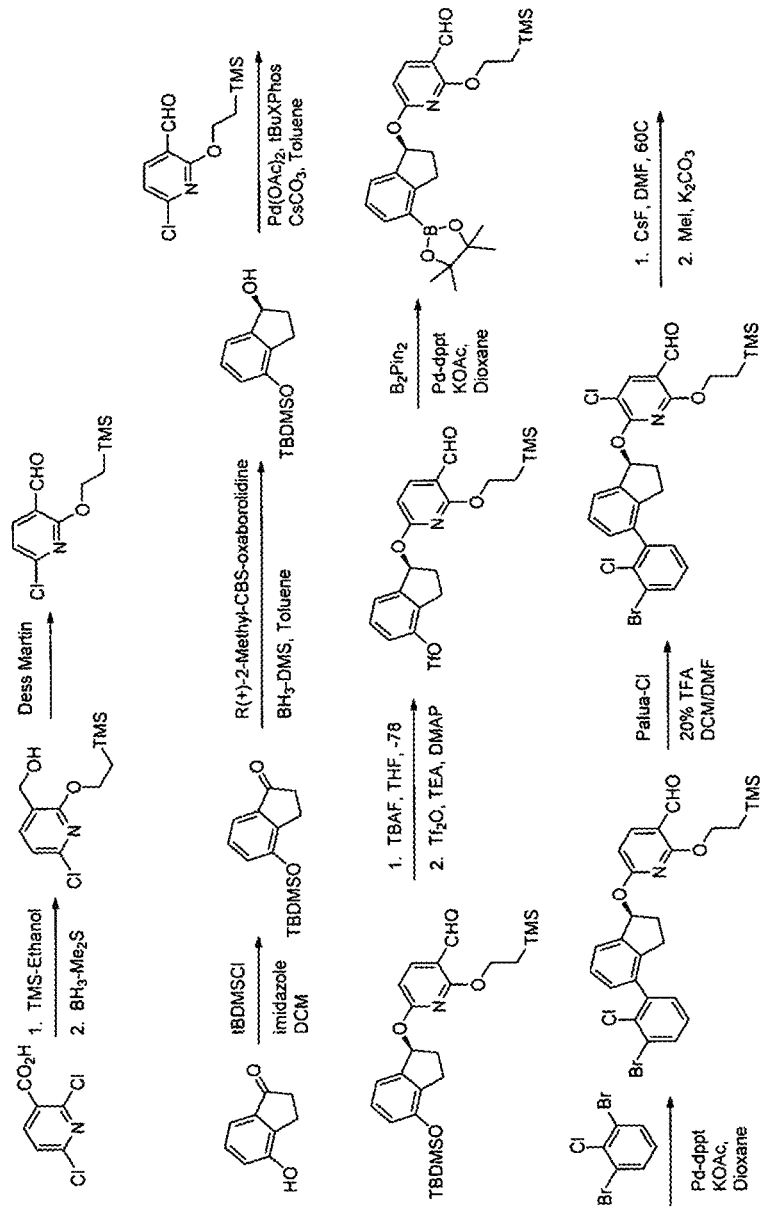
Figure 4. Chemical Synthesis for Protected PD6-Prodrug

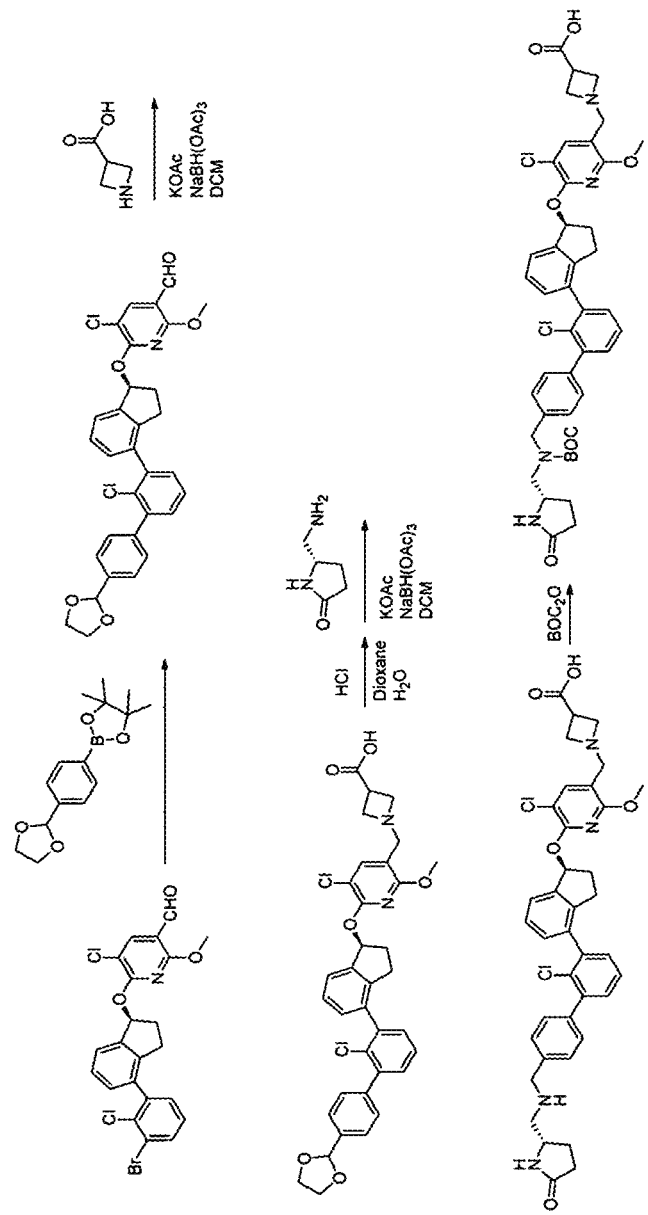
Figure 5. Chemical Synthesis for Protected PD6-Prodrug, Continued

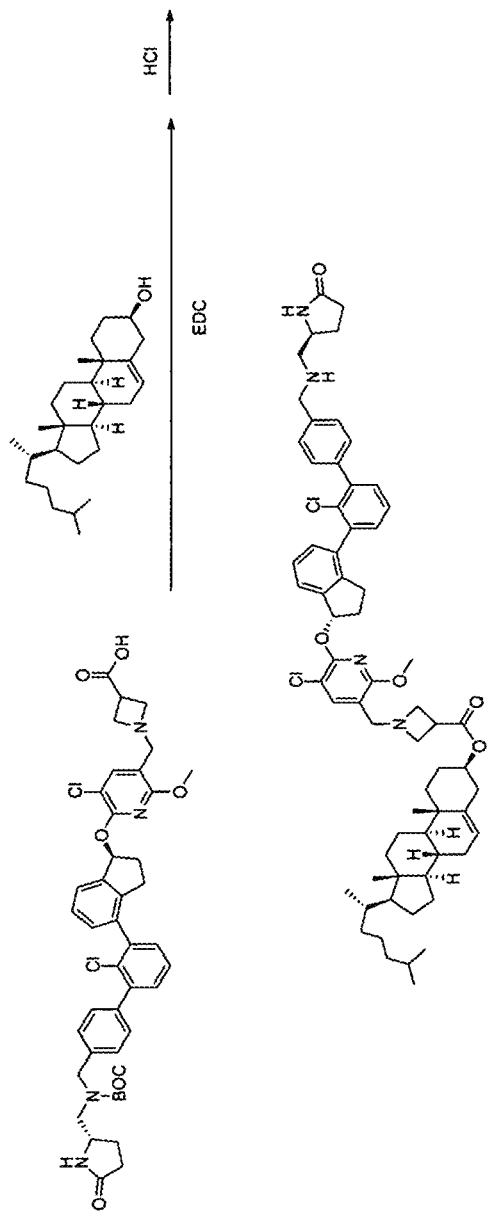
Figure 6. Chemical Synthesis for Protected PD6-Prodrug, Continued

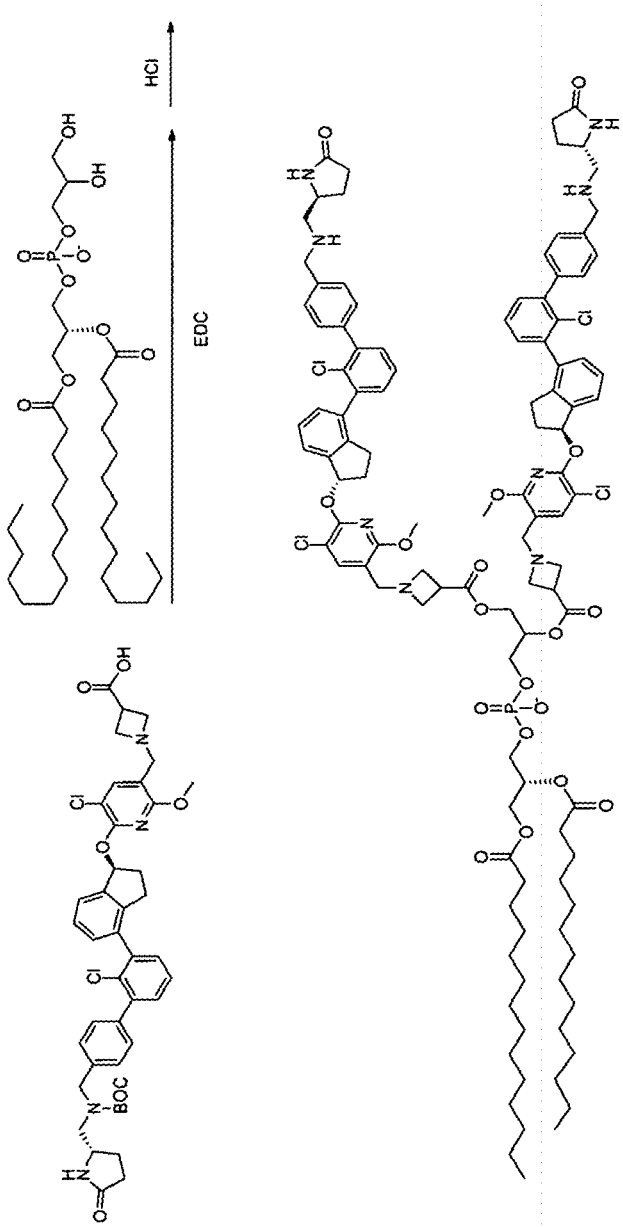
Figure 7. Chemical Synthesis for Protected PD6-Prodrug, Continued

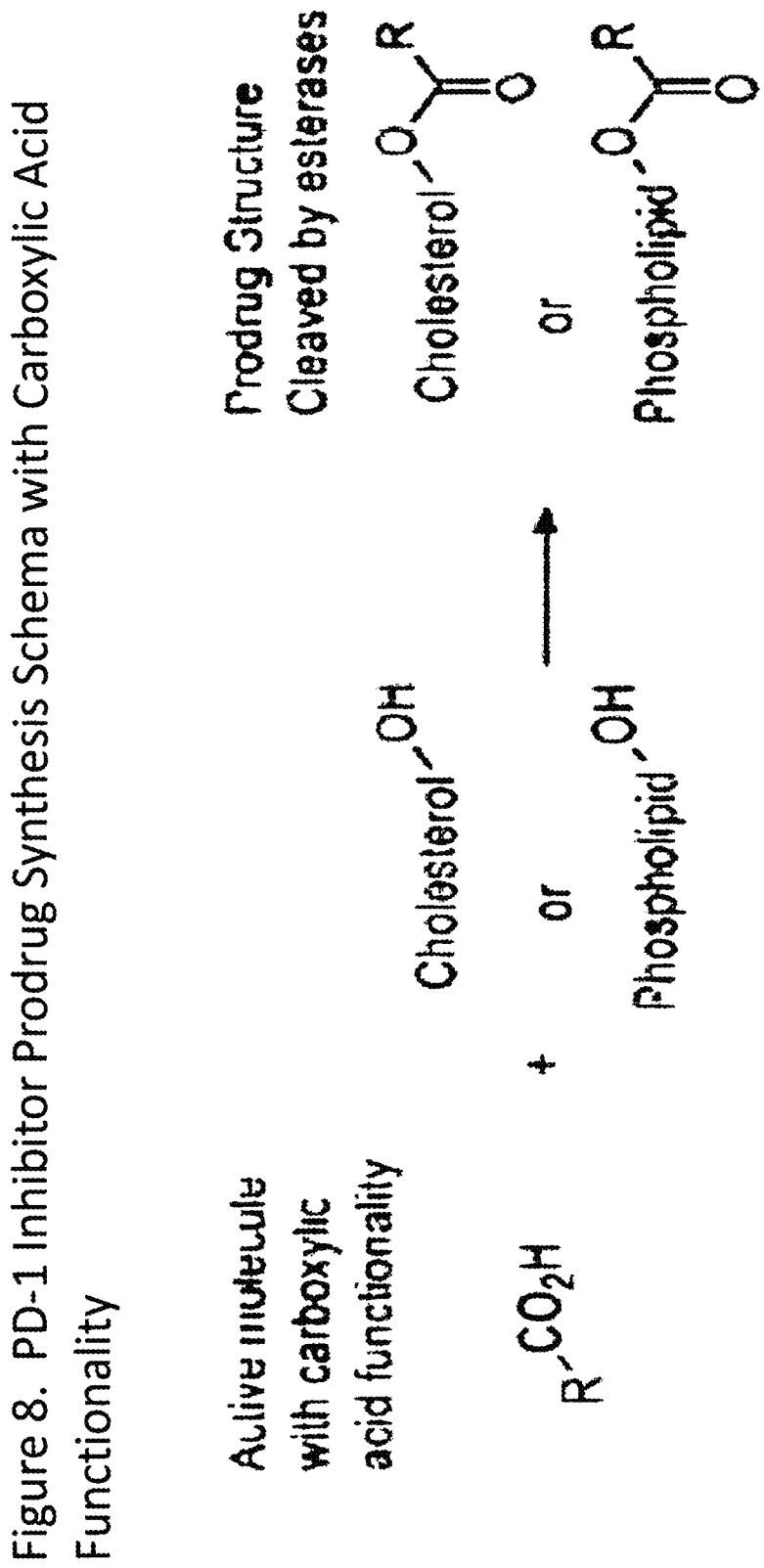
Figure 8. PD-1 Inhibitor Prodrug Synthesis Schema with Carboxylic Acid Functionality

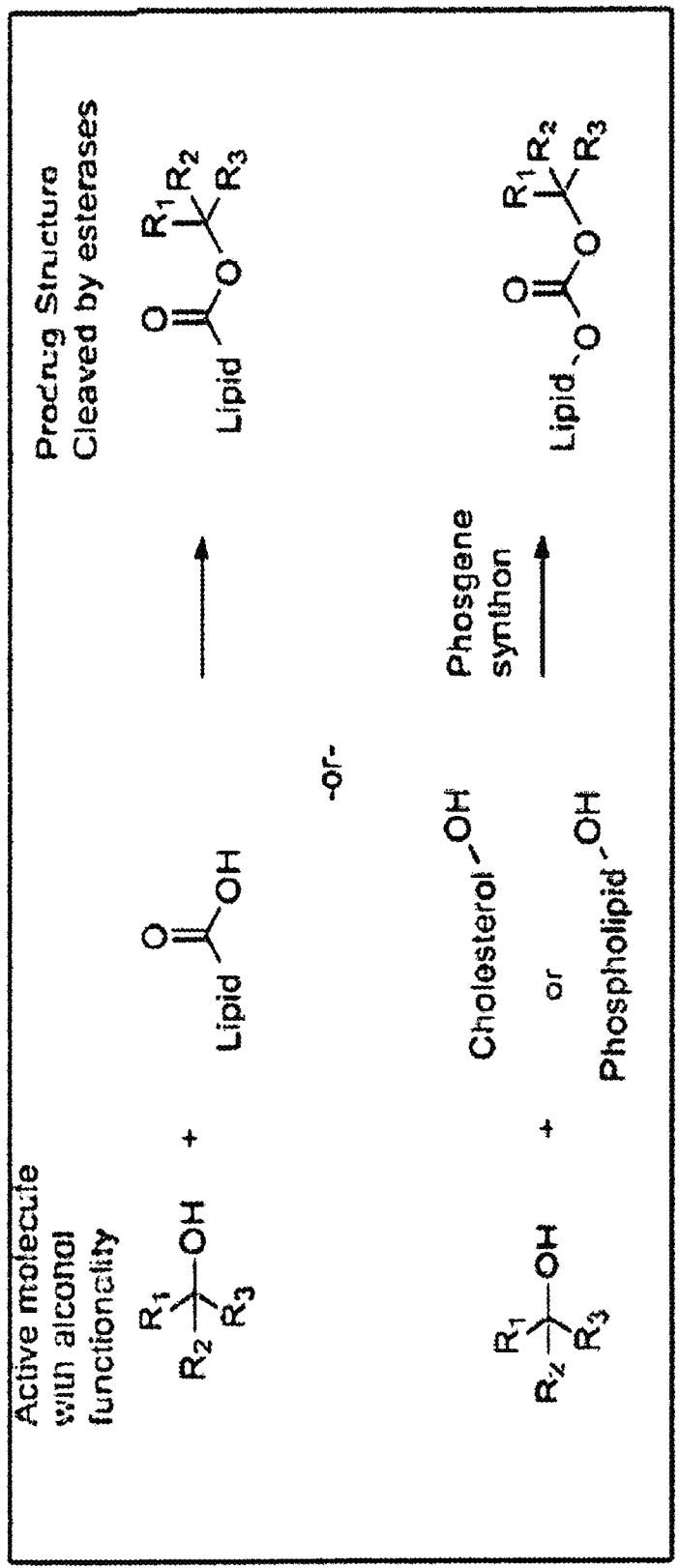
Figure 9. PD-1 Inhibitor Prodrug Synthesis Schema with Alcohol Functionality

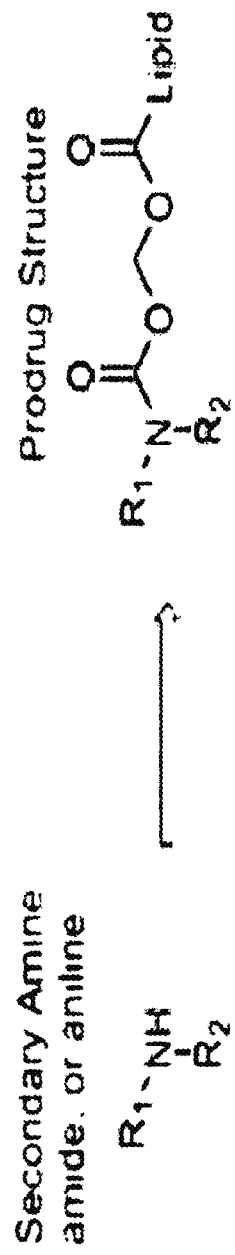
Figure 10. PD-1 Inhibitor Prodrug Synthesis Schema with Secondary Amine, Amide, or Aniline Functionality

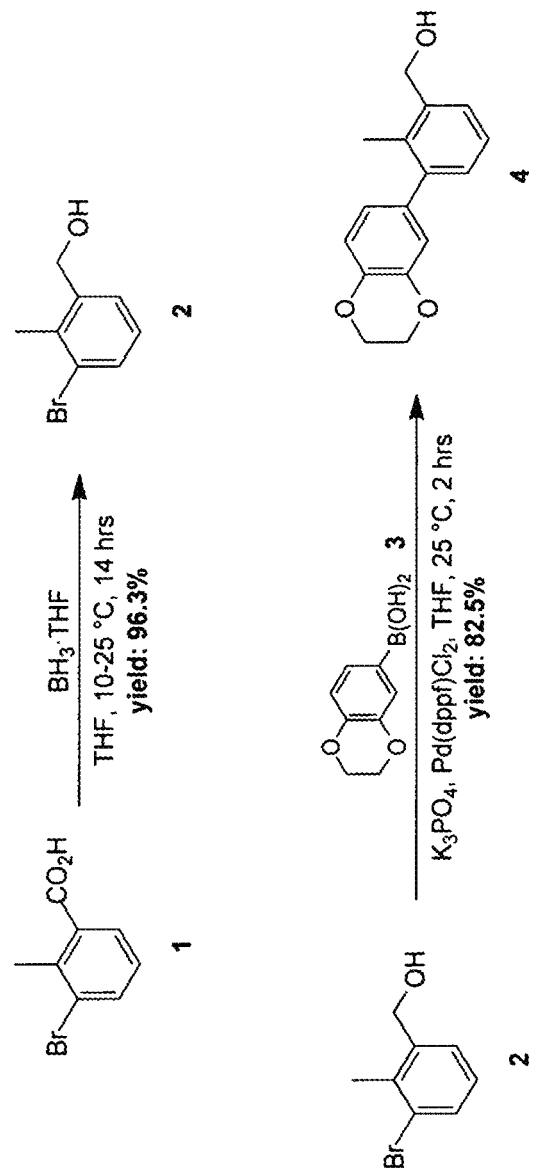
Figure 11. Chemical Synthesis for Protected PD3-Prodrug Comprising Cholesterol

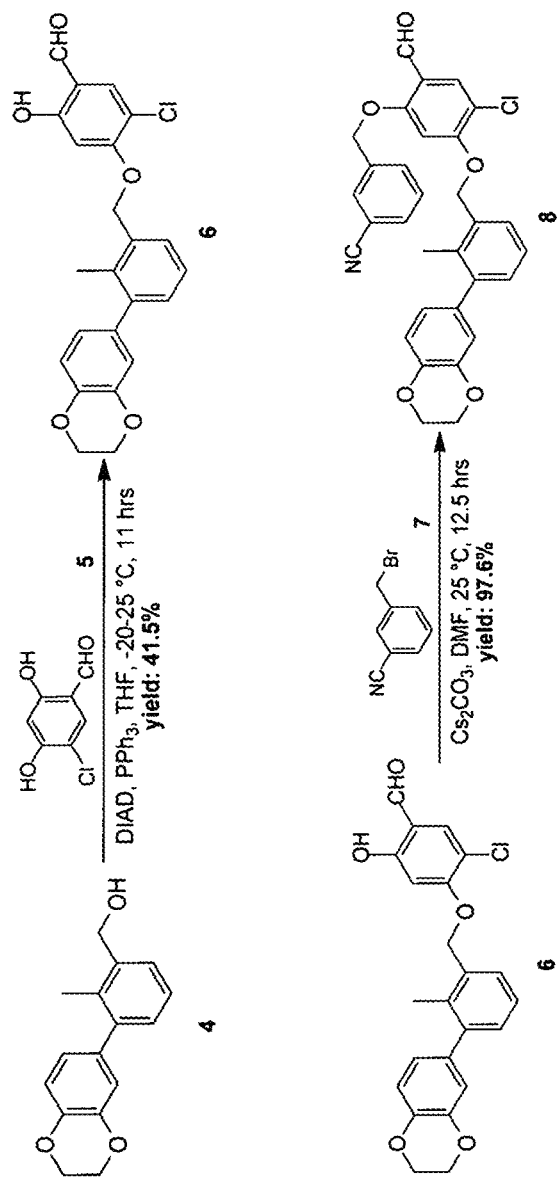
Figure 12. Chemical Synthesis for Protected PD3-Prodrug Comprising Cholesterol, continued.

Figure 13. Chemical Synthesis for Protected PD3-Prodrug Comprising Cholesterol, continued.
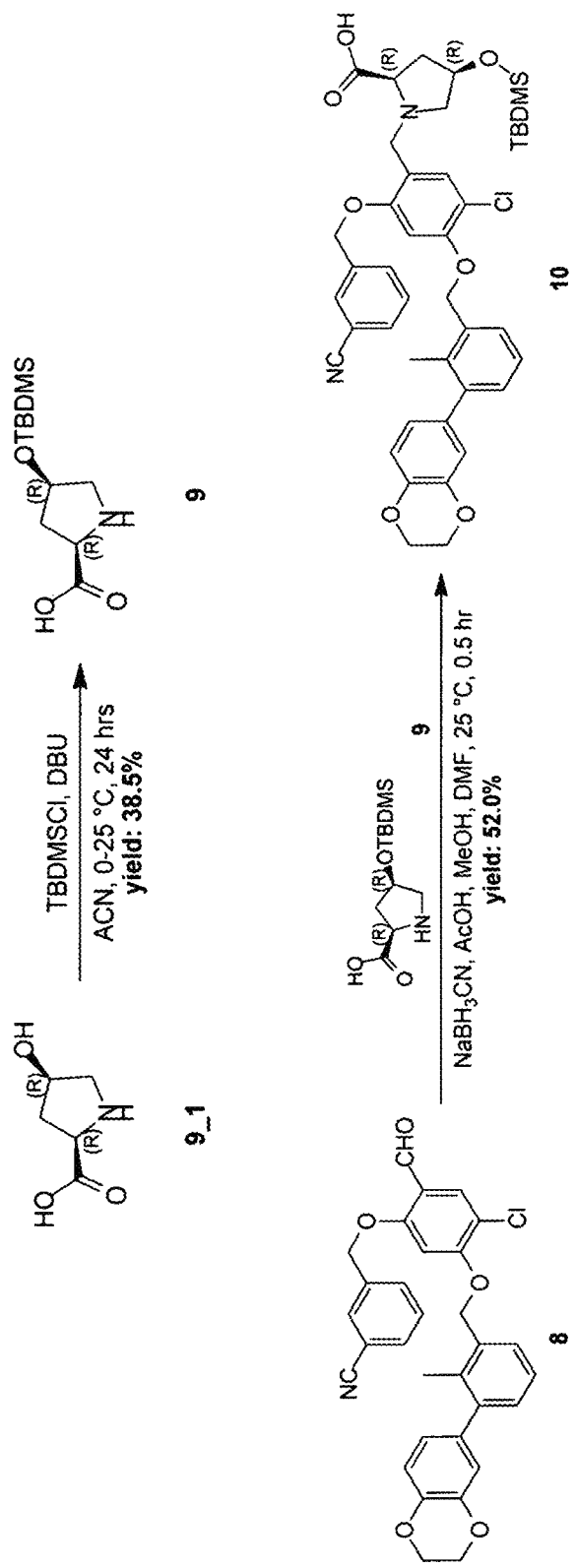

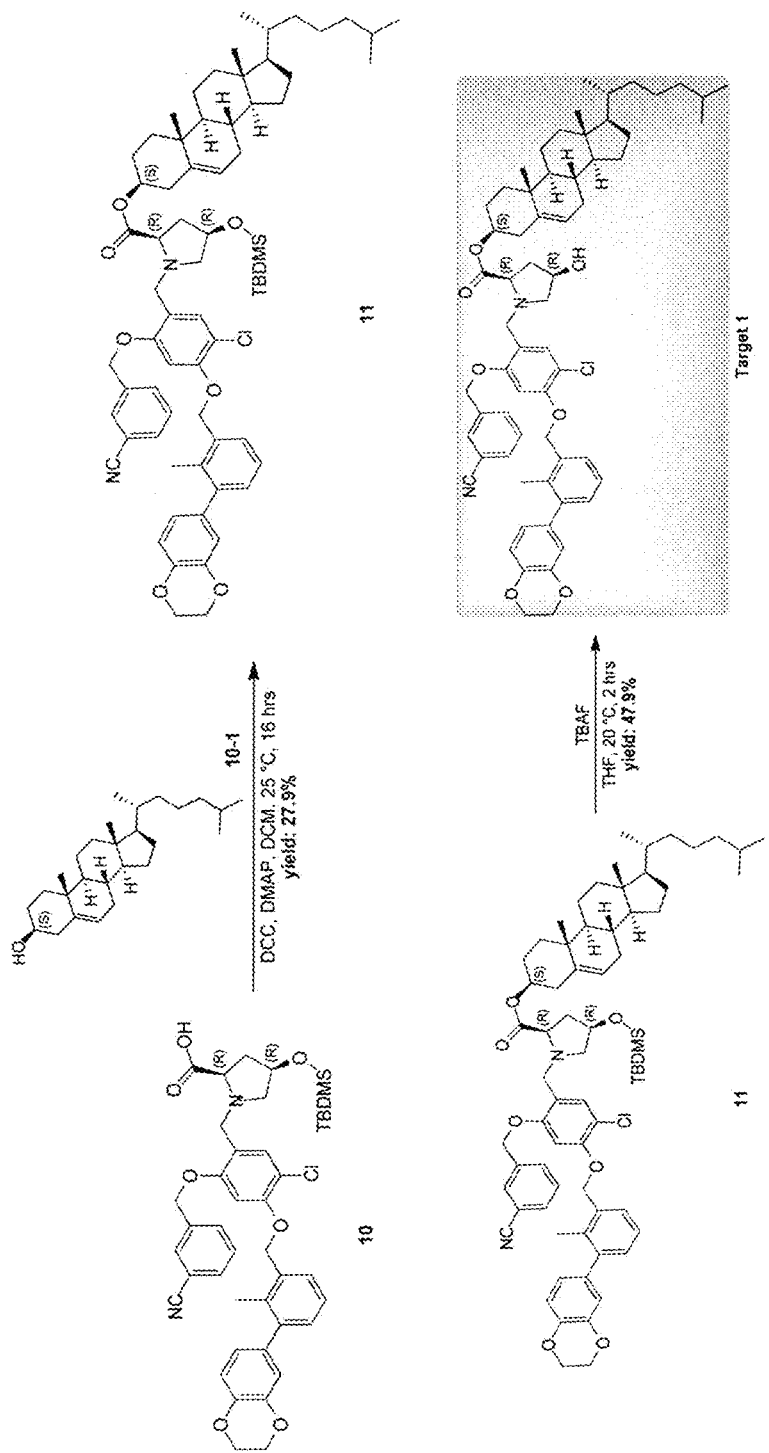
Figure 14. Chemical Synthesis for Protected PD3-Prodrug Comprising Cholesterol, continued.

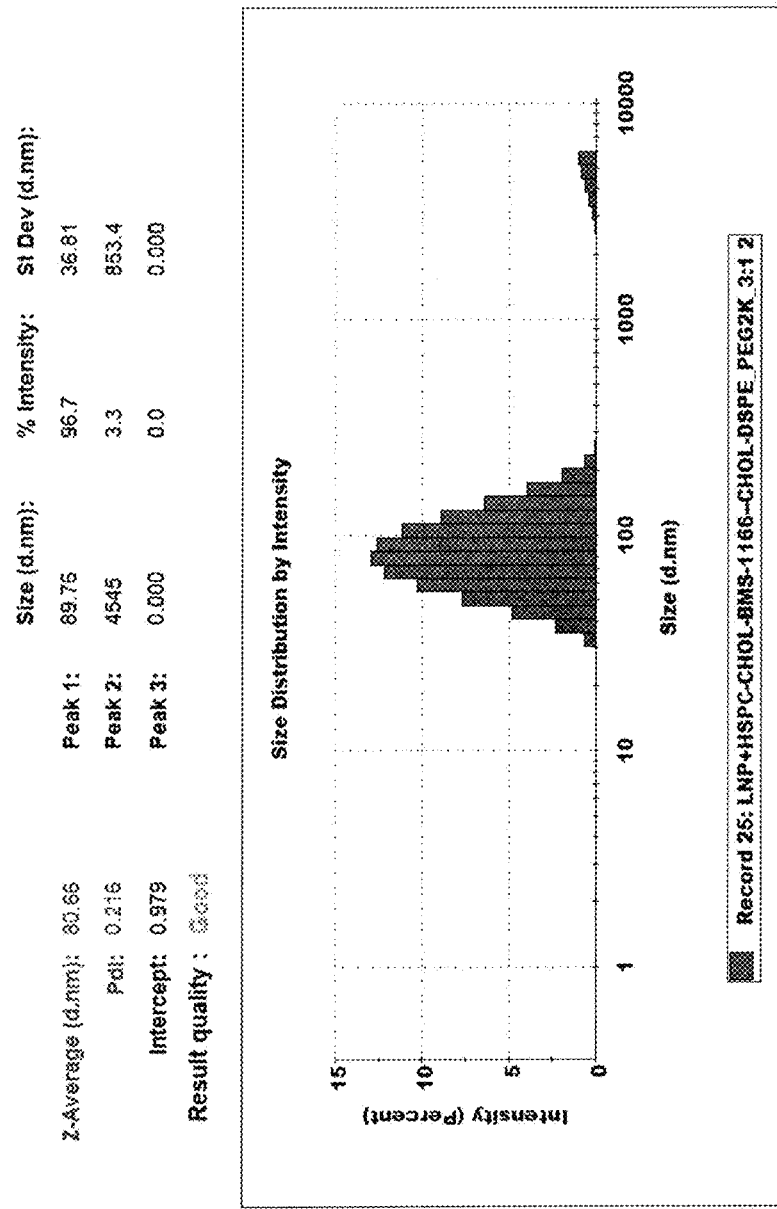
Figure 15. Characterization of LNP-PD3 Liposome

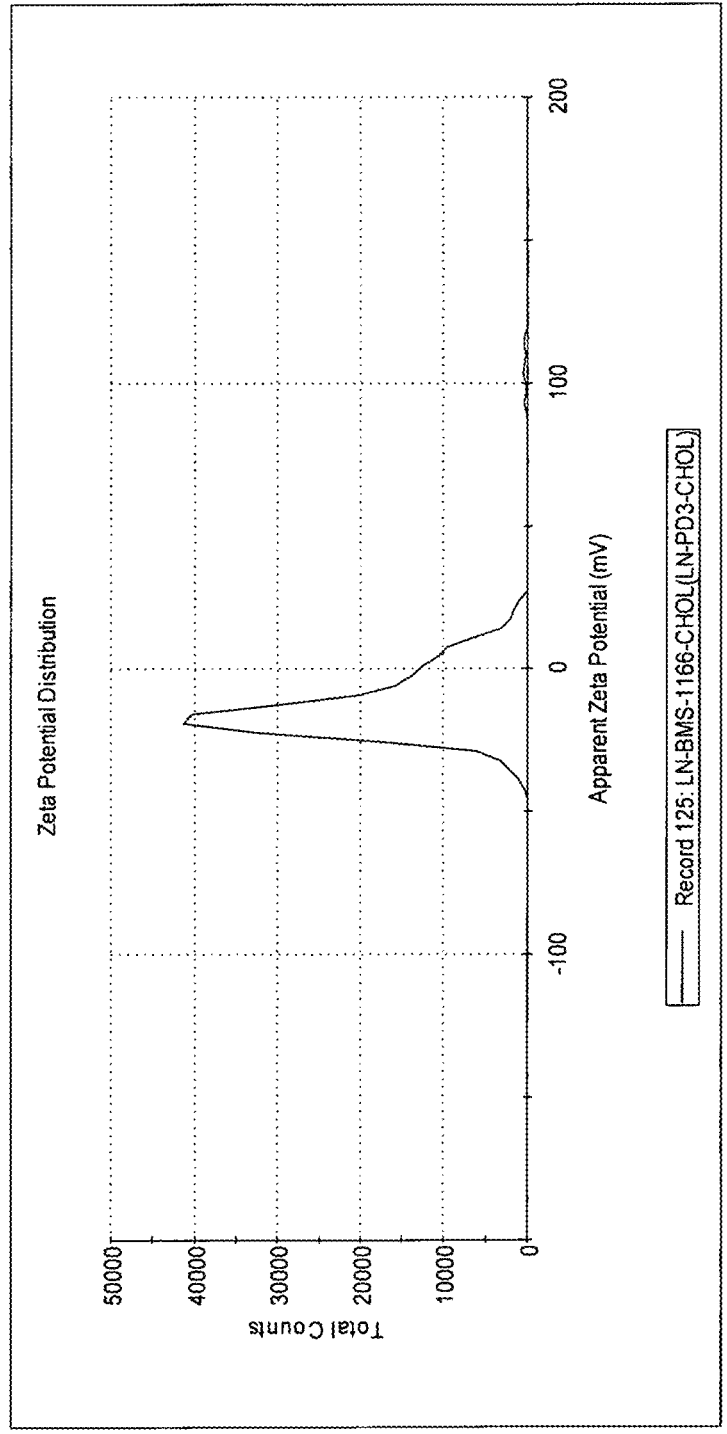
Figure 16. Characterization of LNP-PD3 Liposome (Zeta Potential)

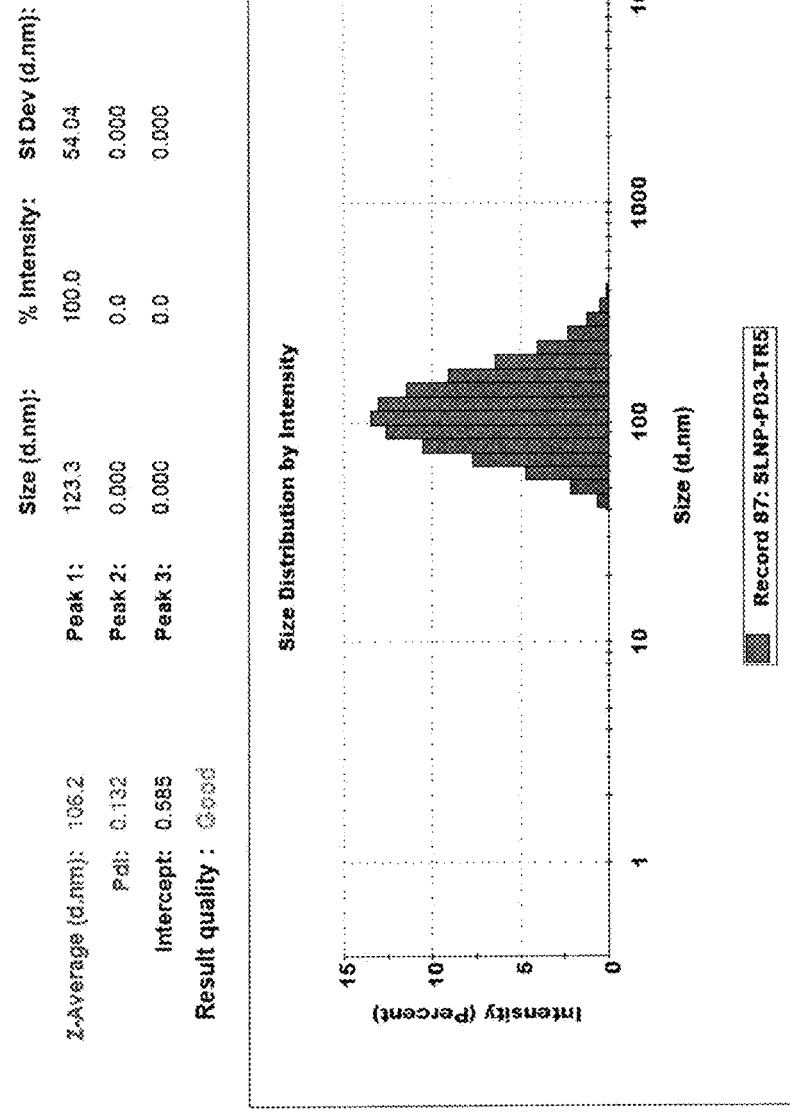
Figure 17. Characterization of SLNP-PD3-TR5 Solid-Lipid Nanoparticle

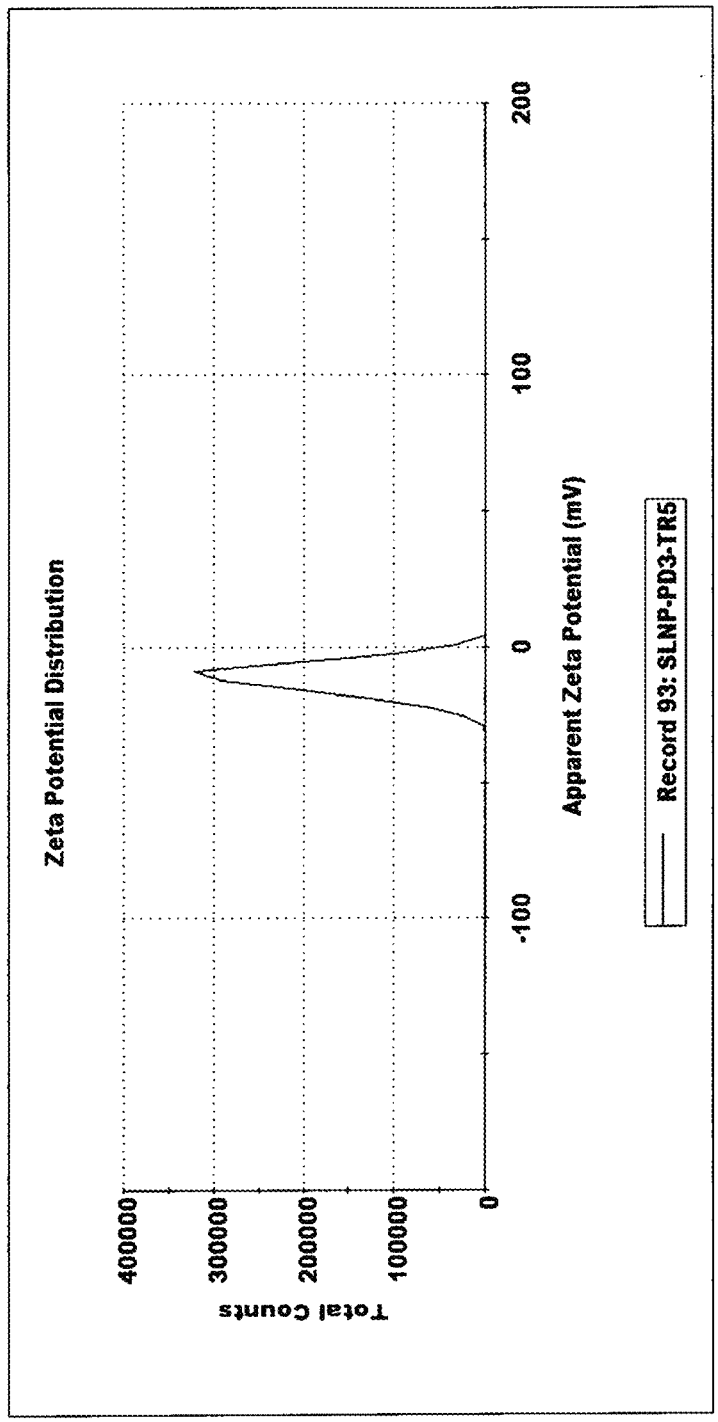
Figure 18. Characterization of SLNP-PD3-TR5 Solid-Lipid Nanoparticle (Zeta Potential)

Figure 19. Characterization of SLNP-PD3-AR5-Dox Solid-Lipid Nanoparticle
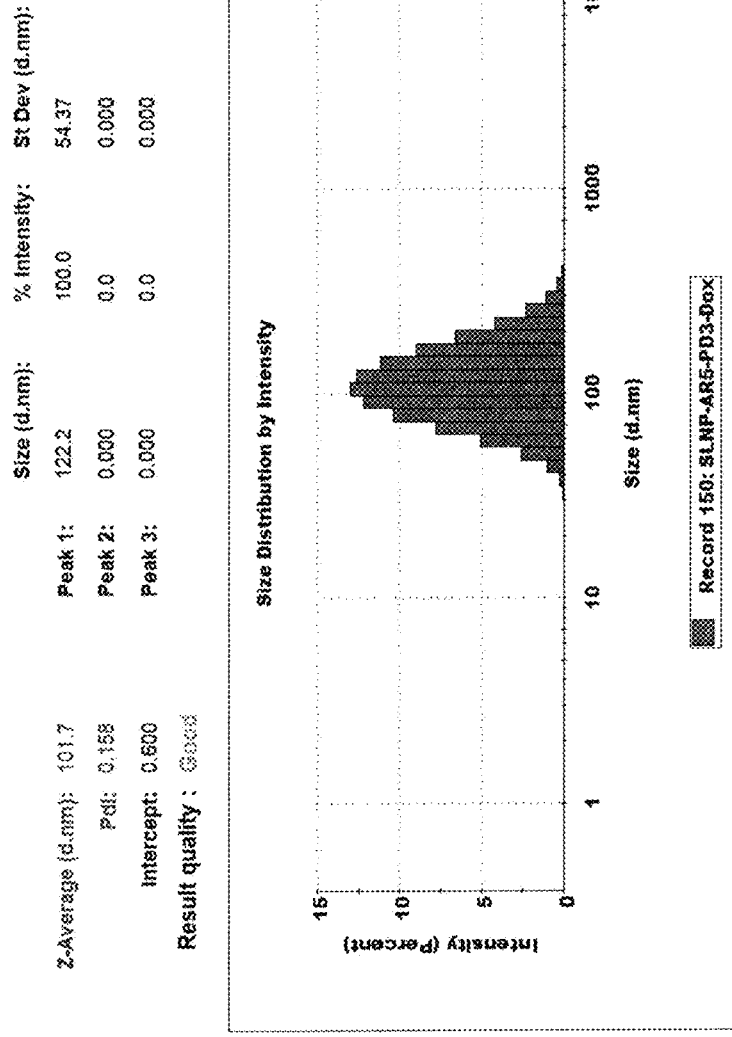

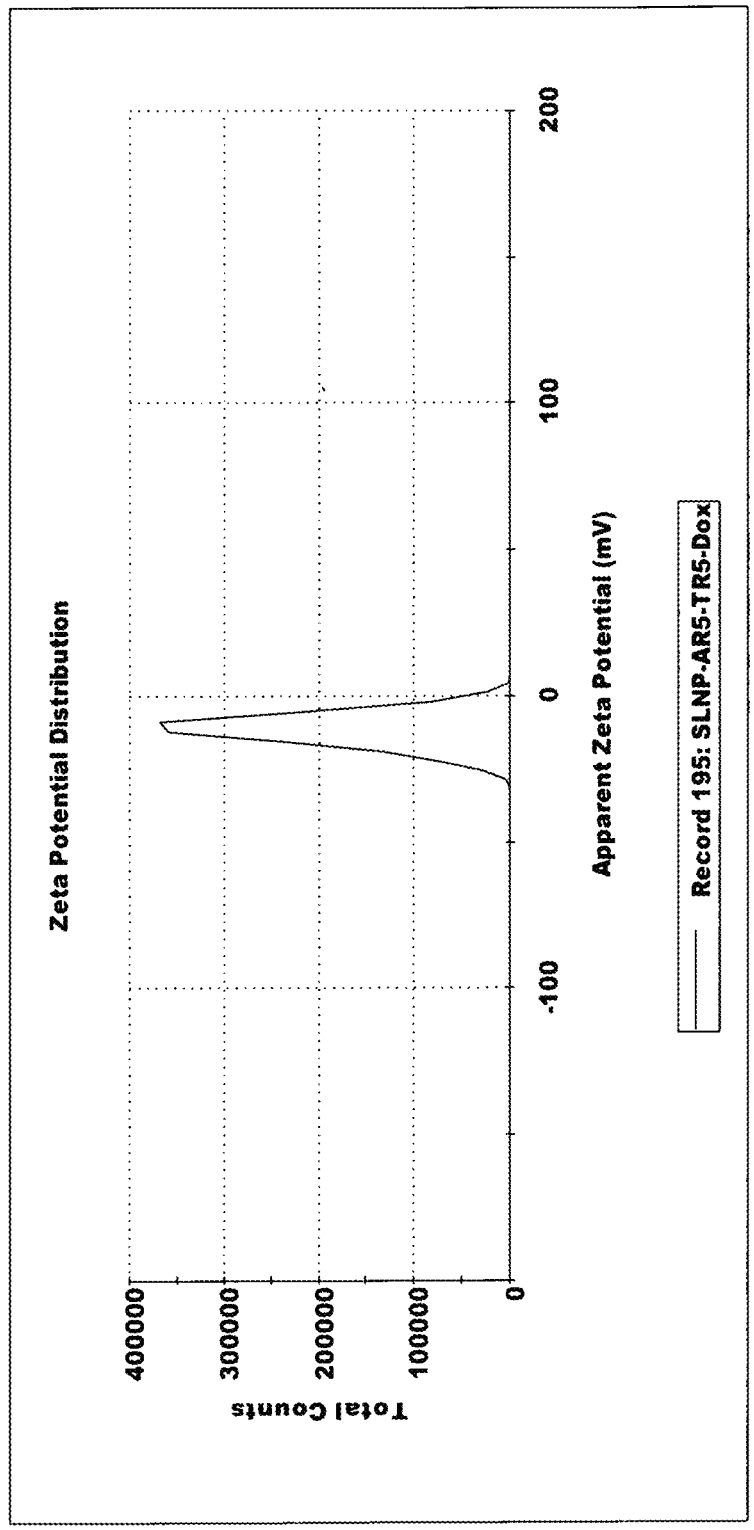
Figure 20. Characterization of SLNP-PD3-AR5-Dox Solid-Lipid Nanoparticle (Zeta Potential)

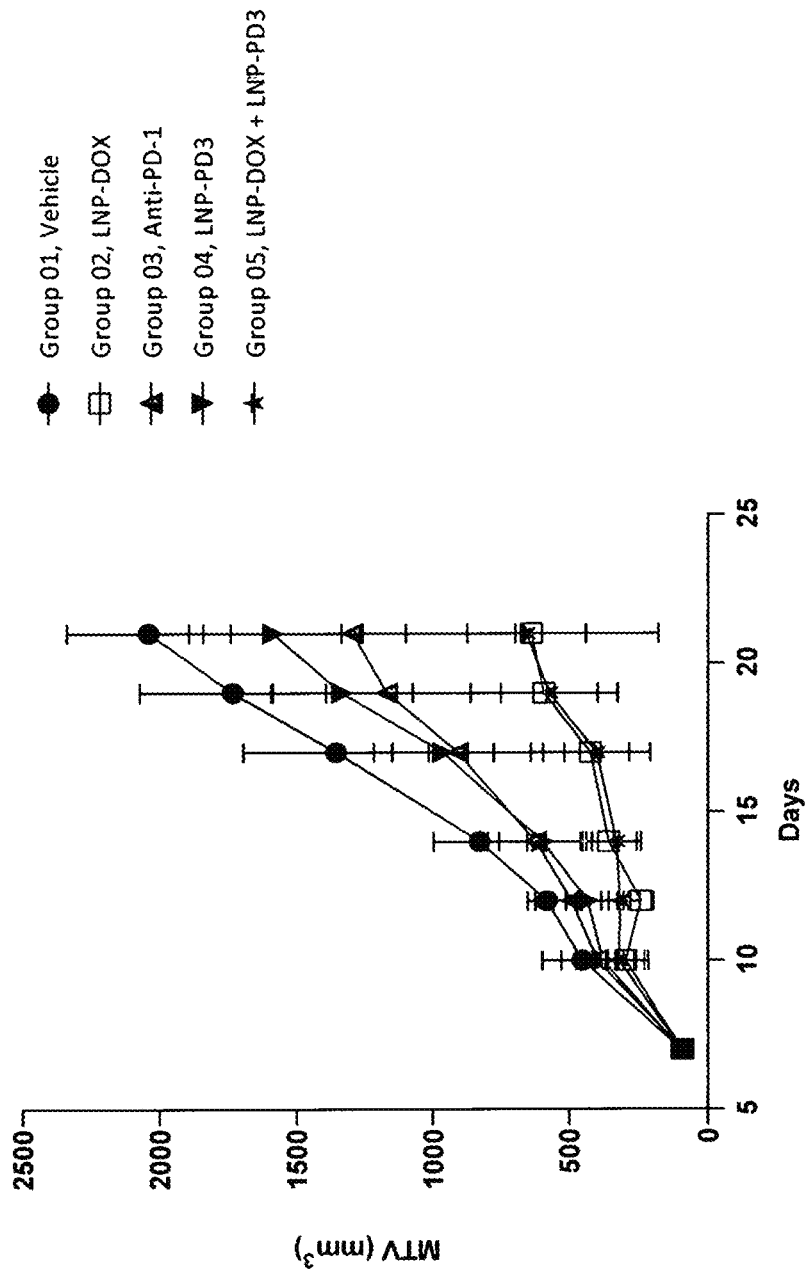
Figure 21. Tumor Inhibition of LNP-PD3 In Multiple Combination(s) Using EMT6 Cells *In Vivo*

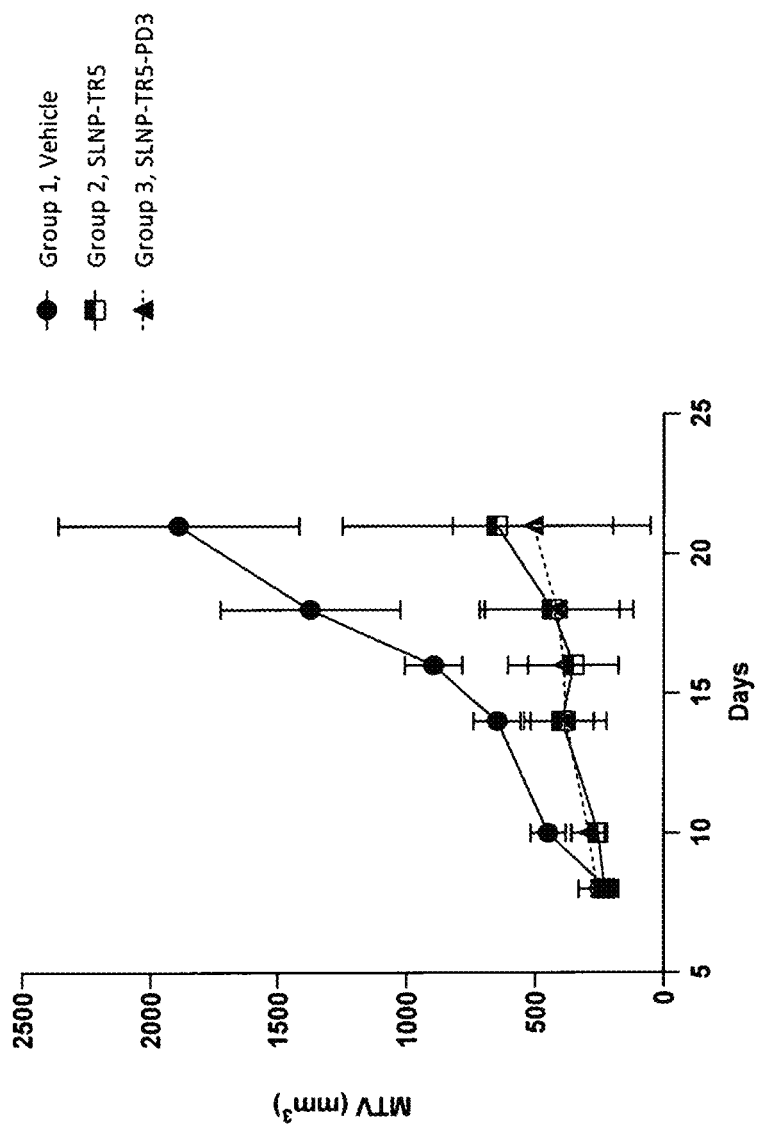
Figure 22. Tumor Inhibition of SLNP-PD3-TR5 Using EMT6 Cells *In Vivo*

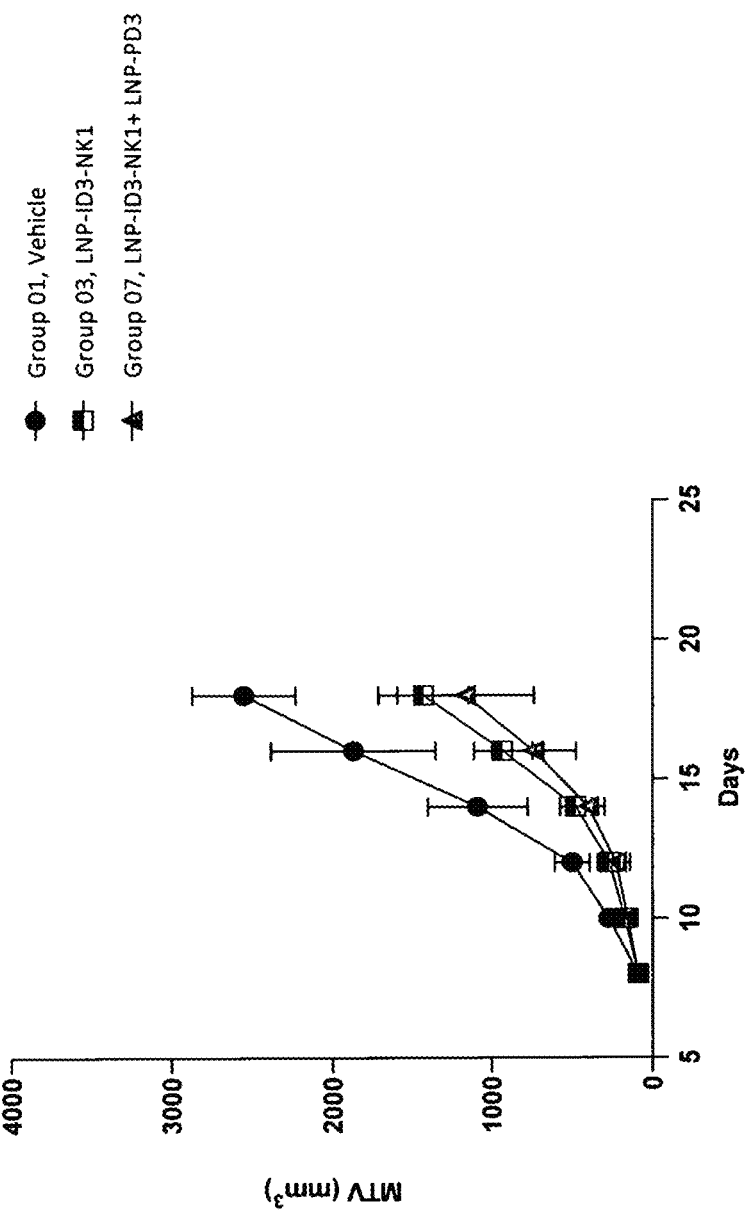
Figure 23. Tumor Inhibition of LNP-PD3 In Combination with LNP-ID3-NK1 Using B16F10 Cells *In Vivo*

FORMULATED AND/OR CO-FORMULATED LIPOSOME COMPOSITIONS CONTAINING PD-1 ANTAGONIST PRODRUGS USEFUL IN THE TREATMENT OF CANCER AND METHODS THEREOF

CROSS-REFERENCE TO RELATED APPLICATIONS

This application claims priority to U.S. Provisional Patent Application No. 63/204,101 filed 11 Sep. 2020, the contents of which are fully incorporated by reference herein.

STATEMENT OF RIGHTS TO INVENTIONS MADE UNDER FEDERALLY SPONSORED RESEARCH

Not applicable.

FIELD OF THE INVENTION

The invention described herein relates to prodrug compositions that inhibit Programmed Cell Death 1 (PD-1) receptor after release of the active inhibitor from the prodrug and nano-formulations comprising such prodrugs. Specifically, the invention relates to prodrug compositions which are formulated within a nanocarrier (e.g., a liposome) and used as a vehicle for cancer therapy in humans. The invention also relates to co-formulations of such prodrugs with other immune-modulating agents or prodrugs. The invention further relates to the treatment of cancers and other immunological disorders and diseases.

BACKGROUND OF THE INVENTION

Cancer is the second leading cause of death next to coronary disease worldwide. Millions of people die from cancer every year and in the United States alone cancer kills well over a half-million people annually, with 1,688,780 new cancer cases diagnosed in 2017 (American Cancer Society). While deaths from heart disease have been declining significantly, those resulting from cancer generally are on the rise. In the early part of the next century, cancer is predicted to become the leading cause of death unless medical developments change the current trend.

Several cancers stand out as having high rates of mortality. In particular, carcinomas of the lung (18.4% of all cancer deaths), breast (6.6% of all cancer deaths), colorectal (9.2% of all cancer deaths), liver (8.2% of all cancer deaths), and stomach (8.2% of all cancer deaths) represent major causes of cancer death for both sexes in all ages worldwide (GLOBOCAN 2018). These and virtually all other carcinomas share a common lethal feature in that they metastasis to sites distant from the primary tumor and with very few exceptions, metastatic disease fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients also experience physical debilitations following treatment. Furthermore, many cancer patients experience a recurrence of their disease.

Although cancer therapy has improved over the past decades and survival rates have increased, the heterogeneity of cancer still demands new therapeutic strategies utilizing a plurality of treatment modalities. This is especially true in treating solid tumors at anatomical crucial sites (e.g., glioblastoma, squamous carcinoma of the head and neck and lung adenocarcinoma) which are sometimes limited to standard radiotherapy and/or chemotherapy. Nonetheless, detrimental effects of these therapies are chemo- and radio resistance, which promote loco-regional recurrences, distant metastases and second primary tumors, in addition to severe side-effects that reduce the patients' quality of life.

Programmed cell death protein 1, also known as PD-1 and CD279, is a cell surface receptor that belongs to the immunoglobulin superfamily and is expressed on T cells and pro-B cells. PD-1 binds two ligands, PD-L1 and PD-L2. PD-1 has a role in regulating the immune system's response to the cells of the human body by down-regulating the immune system and promoting self-tolerance by suppressing T cell inflammatory activity. This prevents autoimmune diseases, but it can also prevent the immune system from killing cancer cells. PD-1 is an immune checkpoint and guards against autoimmunity through two mechanisms. First, it promotes apoptosis (programmed cell death) of antigen-specific T-cells in lymph nodes. Second, it reduces apoptosis in regulatory T cells (anti-inflammatory, suppressive T cells).

PD-1 inhibitors which are a new class of drugs that block PD-1, activate the immune system to attack tumors and are used to treat certain types of cancer.

Additionally, a prodrug is a medication or compound that, after administration, is metabolized (i.e., converted within the body) into a pharmacologically active drug. Instead of administering a drug directly, a corresponding prodrug is used instead to improve how a medicine is absorbed, distributed, metabolized, and/or excreted. Prodrugs are often designed to improve bioavailability when a drug itself is poorly absorbed from the gastrointestinal tract, for example. A prodrug may be used to improve how selectively the drug interacts with cells or processes that are not its intended target. This reduces adverse or unintended effects of a drug, especially important in treatments like chemotherapy, which can have severe unintended and undesirable side effects. Prodrugs can thus be viewed as drugs containing specialized non-toxic protective groups used in a transient manner to alter or to eliminate undesirable properties in the parent molecule.

Finally, a nanocarrier is a nanomaterial being used as a transport for another substance, such as a drug. There are many different types of nanocarriers. For example, nanocarriers include polymer conjugates, polymeric nanoparticles, lipid-based carriers, and dendrimers to name a few. Different types of nanomaterial(s) being used in nanocarriers allows for hydrophobic and hydrophilic drugs to be delivered throughout the body. Since the human body contains mostly water, the ability to deliver hydrophobic drugs effectively in humans is a major therapeutic benefit of nanocarriers. Nanocarriers show promise in the drug delivery process because they can deliver drugs to site-specific targets, allowing drugs to be delivered in certain organs or cells but not in others. Site specificity is a major therapeutic benefit since it prevents drugs from being delivered to the wrong places. Additionally, nanocarriers show specific promise for use in chemotherapy because they can help decrease the adverse, broader-scale toxicity of chemotherapy on healthy, fast-growing cells around the body. Since chemotherapy drugs can be extremely toxic to human cells, it is important that they are delivered to the tumor without being released into other parts of the body.

From the aforementioned, it will be readily apparent to those skilled in the art that a new treatment paradigm is needed in the treatment of cancers and other immunological diseases. By using novel prodrugs in conjunction with modern nanocarrier modalities, a new disease treatment can be achieved with the overall goal of more effective treatment(s), reduced side effects, and greater therapeutic utility in the treatment of cancers, especially the treatment of cancers in solid tumors.

Given the current deficiencies associated with cancer treatment, it is an object of the present invention to provide new and improved methods of treating cancer(s), immunological disorders, and other diseases utilizing prodrugs encapsulated within a nanocarrier.

SUMMARY OF THE INVENTION

The invention provides for PD-1 inhibitor prodrug ("PD-1 Prodrug") compositions comprising a PD-1 inhibitor agent, a lipid, and a biologically cleavable linker. In certain embodiments, nanocarriers comprising PD-1 Prodrug are formulated for use as a delivery modality to treat human diseases such as cancer, including solid tumor cancers as well as other immunological disorders. In certain embodiments, the nanocarriers comprise a lipid-bilayer capable of being incorporated into a drug delivery vehicle (i.e., a liposome). In a further embodiment, the liposome comprises 1,2-Dipalmitoyl-sn-glycero-3-phosphoglycerol, sodium salt (DPPG). In a further embodiment, a liposome of the invention comprises a lipoprotein. In a further preferred embodiment, the liposome of the invention comprises cholesterol.

In a further embodiment, the invention comprises methods of delivering a PD-1 inhibitor to a tumor comprising (i) synthesizing a PD-1 prodrug; (ii) formulating a PD-1 prodrug of the invention in a nanocarrier of the invention; and (iii) administering the nanocarrier to a patient.

In another embodiment, the invention comprises methods of delivering a PD-1 inhibitor with one or more additional immune modulating agent to a tumor comprising (i) synthesizing a PD-1 prodrug; (ii) co-formulating a PD-1 prodrug of the invention in a nanocarrier with one or more additional immune modulating agents of the invention; and (iii) administering the nanocarrier to a patient.

In another embodiment, the immune modulating agents comprise immunogenic-cell death inducing chemotherapeutics, toll receptor agonists, STING agonists, IDO inhibitors, CD1D agonists, TGFβ inhibitors, CTLA4 inhibitors, and/or prodrugs thereof.

In another embodiment, the present disclosure teaches methods of synthesizing PD-1 prodrugs.

In another embodiment, the present disclosure teaches methods of formulating a PD3 Prodrug.

In another embodiment, the present disclosure teaches methods of formulating PD-1 prodrugs within nanocarriers, including but not limited to liposomes.

In another embodiment, the present disclosure teaches methods of formulating PD3 Prodrug within nanocarriers, including but not limited to liposomes.

In another embodiment, the present disclosure teaches methods of treating cancer(s), immunological disorders and other diseases in humans using nanocarriers of the present disclosure.

BRIEF DESCRIPTION OF THE FIGURES

FIG. 1. Chemical Synthesis for Protected PD3-Prodrug.
FIG. 2. Chemical Synthesis for Protected PD3-Prodrug, continued.
FIG. 3. Chemical Synthesis for Protected PD3-Prodrug, continued.
FIG. 4. Chemical Synthesis for Protected PD6-Prodrug.
FIG. 5. Chemical Synthesis for Protected PD6-Prodrug, continued.
FIG. 6. Chemical Synthesis for Protected PD6-Prodrug, continued.
FIG. 7. Chemical Synthesis for Protected PD6-Prodrug, continued.
FIG. 8. PD-1 Inhibitor Prodrug Synthesis Schema with Carboxylic Acid Functionality.
FIG. 9. PD-1 Inhibitor Prodrug Synthesis Schema with Alcohol Functionality.
FIG. 10. PD-1 Inhibitor Prodrug Synthesis Schema with Secondary Amine, Amide, or Aniline Functionality.
FIG. 11. Chemical Synthesis for Protected PD3-Prodrug Comprising Cholesterol.
FIG. 12. Chemical Synthesis for Protected PD3-Prodrug Comprising Cholesterol, continued.
FIG. 13. Chemical Synthesis for Protected PD3-Prodrug Comprising Cholesterol, continued.
FIG. 14. Chemical Synthesis for Protected PD3-Prodrug Comprising Cholesterol, continued.
FIG. 15. Characterization of LNP-PD3 Liposome.
FIG. 16. Characterization of LNP-PD3 Liposome (Zeta Potential).
FIG. 17. Characterization of SLNP-PD3-TR5 Solid-Lipid Nanoparticle.
FIG. 18. Characterization of SLNP-PD3-TR5 Solid-Lipid Nanoparticle (Zeta Potential).
FIG. 19. Characterization of SLNP-PD3-AR5-Dox Solid-Lipid Nanoparticle.
FIG. 20. Characterization of SLNP-PD3-AR5-Dox Solid-Lipid Nanoparticle (Zeta Potential).
FIG. 21. Tumor Inhibition of LNP-PD3 In Multiple Combination(s) Using EMT6 Cells In Vivo.
FIG. 22. Tumor Inhibition of SLNP-PD3-TR5 Using EMT6 Cells In Vivo.
FIG. 23. Tumor Inhibition of LNP-PD3 In Combination with LNP-ID3-NK1 Using B16F10 Cells In Vivo.

DETAILED DESCRIPTION OF THE INVENTION

Outline of Sections
I.) Definitions
II.) Prodrugs
III.) Chemical Compounds
IV.) Lipids
V.) Linkage Unit(s) ("LU")
VI.) Nanocarriers
VII.) Liposomes
VIII.) Pharmaceutical Formulation
IX.) Combination Therapy
X.) Methods of Delivering Nanocarriers Comprising PD-1 Prodrugs to a Cell Expressing PD-1-L1/L2
XI.) Methods of Treating Cancer(s) and Other Immunological Disorder(s)
XII.) KITS/Articles of Manufacture I.) Definitions Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art.

When a trade name is used herein, reference to the trade name also refers to the product formulation, the generic drug, and the active pharmaceutical ingredient(s) of the trade name product, unless otherwise indicated by context.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub combinations of A, B, C, and D.

Numerical ranges recited herein by endpoints include all numbers and fractions subsumed within that range (e.g., 1 to 5 includes, but is not limited to, 1, 1.5, 2, 2.75, 3, 3.90, 4, and 5).

As used herein, the phrase "consisting essentially of" limits the scope of a claim to the specified materials or steps, plus those that do not materially affect the basic and novel characteristic(s) of the claimed subject matter.

The terms "advanced cancer", "locally advanced cancer", "advanced disease" and "locally advanced disease" mean cancers that have extended through the relevant tissue capsule and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease and these patients have substantially less favorable outcomes compared to patients having clinically localized (organ-confined) cancer.

As used herein the term "alkyl" can refer to $C_1$-$C_{20}$ inclusive, linear (i.e., "straight-chain"), branched, or cyclic, saturated or at least partially and in some cases unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl, or propyl, is attached to a linear alkyl chain. "Lower alkyl" refers to an alkyl group having 1 to about 8 carbon atoms (i.e., a $C_1$-$C_8$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_1$-$C_8$ straight-chain alkyls. In other embodiments, "alkyl" refers, in particular, to $Ci_{-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered aromatic and heteroaromatic rings. The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc.) in the backbone of a ring structure. Nitrogen-containing heteroaryl moieties include, but are not limited to, pyridine, imidazole, benzimidazole, pyrazole, pyrazine, triazine, pyrimidine, and the like.

The terms "anticancer drug", "chemotherapeutic", and "anticancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). In some embodiments, the term "chemotherapeutic" as used herein refers to a non-PS molecule that is used to treat cancer and/or that has cytotoxic ability. More traditional or conventional chemotherapeutic agents can be described by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine).

"Aralkyl" refers to an alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched, or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—($CH_2$)3-); cyclohexylene (—$C_6H_{10}$—); —CH=CH—CH=CH—; —CH=CH—$CH_2$—; —($CH_2$)$_q$—N(R)—($CH_2$)—, wherein each of q is an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (-0-$CH_2$-0-); and ethylenedioxyl (-0-($CH_2$)$_2$-0-). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "amino" refers to the group —N(R)$_2$ wherein each R is independently H, alkyl, substituted alkyl, aryl, substituted aryl, aralkyl, or substituted aralkyl. The terms "aminoalkyl" and "alkylamino" can refer to the group —N(R)$_2$ wherein each R is H, alkyl or substituted alkyl, and wherein at least one R is alkyl or substituted alkyl. "Arylamine" and "aminoaryl" refer to the group —N(R)$_2$ wherein each R is H, aryl, or substituted aryl, and wherein at least one R is aryl or substituted aryl, e.g., aniline (i.e., —$NHC_6H_5$).

"Bulk" (a.k.a. Drug Substance) means the drug substance or the drug product which has not been filled into final containers for distribution. Final formulated bulk generally refers to drug product which is formulated and being stored or held prior to filling. Drug substance may be stored or held as "bulk" or "concentrated bulk" prior to formulation into drug product.

The terms "carboxylate" and "carboxylic acid" can refer to the groups —C(=O)O$^-$ and —C(=O)OH, respectively. The term "carboxyl" can also refer to the —C(=O)OH group.

The terms "conjugate" and "conjugated" as used herein can refer to the attachment (e.g., the covalent attachment) of two or more components (e.g., chemical compounds, polymers, biomolecule, particles, etc.) to one another. In some embodiments, a conjugate can comprise monovalent moieties derived from two different chemical compounds covalently linked via a bivalent linker moiety (e.g., an optionally substituted alkylene or arylene). In some embodiments, the linker can contain one or more biodegradable bond, such that one or more bonds in the linker can be broken when the prodrug is exposed to a particular physiological environment or enzyme (for example, esterases).

The term "compound" refers to and encompasses the chemical compound (e.g. a prodrug) itself as well as, whether explicitly stated or not, and unless the context makes clear that the following are to be excluded: amorphous and crystalline forms of the compound, including polymorphic forms, where these forms may be part of a mixture or in isolation; free acid and free base forms of the compound, which are typically the forms shown in the structures provided herein; isomers of the compound, which refers to optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers; isotopes of the compound, including deuterium- and tritium-containing compounds, and including compounds containing radioisotopes, including therapeutically- and diagnostically-effective radioisotopes; multimeric forms of the compound, including dimeric, trimeric, etc. forms; salts of the compound, preferably pharmaceutically acceptable salts, including acid addition salts and base addition salts, including salts having organic counterions and inorganic counterions, and including zwitterionic forms, where if a compound is associated with two or more counterions, the two or more counterions may be the same or different; and solvates of the compound, including hemisolvates, monosolvates, disolvates, etc., including organic solvates and inorganic solvates, said inorganic solvates including hydrates; where if a compound is associated with two or more solvent molecules, the two or more solvent molecules may be the same or different. In some instances, reference made herein to a compound of the invention will include an explicit reference to one or of the above forms, e.g., salts and/or solvates; however, this reference is for emphasis only, and is not to be construed as excluding other of the above forms as identified above.

"Drug product" means a final formulation that contains an active drug ingredient (i.e., liposomes containing PD-1 inhibitor prodrugs) generally, but not necessarily, in association with inactive ingredients. The term also includes a finished dosage form that does not contain an active ingredient but is intended to be used as a placebo.

The term "disulfide" can refer to the —S—S— group.

The term "empty vesicle" means an unloaded lipid vesicle by itself.

The term "ester" as used herein means a chemical compound derived from acid (organic or inorganic) in which at least one —OH hydroxyl group is replaced by an —O-alkyl (alkoxy) or O-Aryl (aryloxy) group.

The term "esterase" as used herein is a hydrolase enzyme that splits esters into an acid and an alcohol.

"Excipient" means an inactive substance used as a carrier for the active ingredients in a drug such as vaccines. Excipients are also sometimes used to bulk up formulations with very potent active ingredients, to allow for convenient and accurate dosage. Examples of excipients include but are not limited to, antiadherents, binders, coatings, disintegrants, fillers, diluents, flavors, colors, lubricants, and preservatives.

The terms "halo", "halide", or "halogen" as used herein refer to fluoro, chloro, bromo, and iodo groups.

The terms "hydroxyl" and "hydroxy" refer to the —OH group.

The terms "inhibit" or "inhibition of" as used herein means to reduce by a measurable amount, or to prevent entirely.

The terms "individual" or "patient," as used in the context of this disclosure can be used interchangeably.

As used herein, the term "ligand" refers generally to a species, such as a molecule or ion, which interacts, e.g., binds, in some way with another species. See Martell, A. E., and Hancock, R. P., Metal Complexes in Aqueous Solutions, Plenum: New York (1996), which is incorporated herein by reference in its entirety.

The term "lipid" as used herein refers to a class of naturally occurring (organic) compounds that are insoluble in polar solvents. In the context of the disclosure, a lipid refers to conventional lipids, phospholipids, cholesterol, chemically functionalized lipids for attachment of PEG and ligands, etc.

The term "lipid bilayer" or "LB" refers to any double layer of oriented amphipathic lipid molecules in which the hydrocarbon tails face inward to form a continuous nonpolar phase.

The term(s) "liposome" or "lipid vesicle" or "vesicle" are used interchangeably to refer to an aqueous compartment enclosed by a lipid bilayer, as being conventionally defined (see, Stryer (1981) Biochemistry, 2d Edition, W. H. Freeman & Co., p. 213).

The term "mammal" refers to any organism classified as a mammal, including mice, rats, rabbits, dogs, cats, cows, horses, and humans. In one embodiment of the invention, the mammal is a mouse. In another embodiment of the invention, the mammal is a human.

The terms "mercapto" or "thiol" refer to the —SH group.

The terms "metastatic cancer" and "metastatic disease" mean cancers that have spread to regional lymph nodes or to distant sites and are meant to include stage D disease under the AUA system and stage TxNxM+ under the TNM system.

The terms "nanocarrier", "nanoparticle, and "nanoparticle drug carrier" are used interchangeably and refer to a nanostructure having an aqueous, solid, or polymeric interior core. In certain embodiments the nanocarrier comprises a lipid bilayer encasing (or surrounding or enveloping) the porous particle core. In certain embodiments the nanocarrier is a liposome, lipid nanoparticle ("LNP") or a solid-lipid nanoparticle ("SLNP").

The terms "nanoscale particle," "nanomaterial," "nanocarrier", and "nanoparticle" refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is between about 20 nm and about 250 nm (e.g., about 20, 30, 40, 50, 60, 70, 80, 90, 100, 110, 120, 130, 140, 150, 160, 170, 180, 190, 200, 210, 220, 230, 240, or 250 nm).

The term "nanovesicle" refers to a "lipid vesicle" having a diameter (or population of vesicles having a mean diameter) ranging from about 20 nm, or from about 30 nm, or from about 40 nm, or from about 50 nm up to about 500 nm, or up to about 400 nm, or up to about 300 nm, or up to about 200 nm, or up to about 150 nm, or up to about 100 nm, or up to about 80 nm. In certain embodiments a nanovesicle has a diameter ranging from about 40 nm up to about 80 nm, or from about 50 nm up to about 70 nm.

"Pharmaceutically acceptable" refers to a non-toxic, inert, and/or composition that is physiologically compatible with humans or other mammals.

"Pharmaceutical formulation" means the process in which different chemical substances are combined to a pure drug substance to produce a final drug product.

The term "phosphonate" refers to the —P(═O)(OR)$_2$ group, wherein each R can be independently H, alkyl, aralkyl, aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "phosphate" refers to the —OP(═O)(OR')$_2$ group, where R' is H or a negative charge. The term "prodrug" means a medication or compound that, after administration, is metabolized into a pharmacologically active drug. For the purposes of this disclosure, a prodrug of the invention comprises three (3) components: (i) a drug moiety; (ii) a lipid moiety; and (iii) a linkage unit ("LU").

The term "PD1 prodrug" means a prodrug of the inventions wherein the drug moiety comprises a PD1 inhibitor.

The term "pyrolipid" refers to a conjugate of a lipid and a porphyrin, porphyrin derivative, or porphyrin analog. In some embodiments, the pyrolipid can comprise a lipid conjugate wherein a porphyrin or a derivative or analog thereof is covalently attached to a lipid side chain. See, for example U.S. Patent Application Publication No. 2014/0127763.

As used herein, the terms "specific", "specifically binds" and "binds specifically" refer to the selective binding of nanocarrier of the invention to the target PD-1/L-1/2.

The term "supported lipid bilayer" means a lipid bilayer enclosing a porous particle core. This definition as set forth in the disclosure is denoted because the lipid bilayer is located on the surface and supported by a porous particle core. In certain embodiments, the lipid bilayer can have a thickness ranging from about 6 nm to about 7 nm which includes a 3-4 nm thickness of the hydrophobic core, plus the hydrated hydrophilic head group layers (each about 0.9 nm) plus two partially hydrated regions of about 0.3 nm each. In various embodiments, the lipid bilayer surrounding the liposome comprises a continuous bilayer or substantially continuous bilayer that effectively envelopes and seals the PD1 inhibitor.

The term "thioalkyl" can refer to the group —SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

The term "therapeutically effective amount" refers to the amount of active prodrug, nano-encapsulated prodrug, or pharmaceutical agent that elicits the biological or medicinal response in a tissue, system, animal, individual or human.

The term "unsupported lipid bilayer" means an uncoated lipid bilayer in a lipid vesicle or liposome.

II.) Prodrugs

As shown in the present disclosure and for the purposes of this invention, a suitable prodrug is formed by conjugating a drug moiety of the invention (See, section entitled Drug Moieties) to a lipid moiety of the invention (See, section entitled Lipids) via an LU (See, section entitled Linkage Units) of the present disclosure. For the purposes of this disclosure, formation of a PD-1 prodrug can utilize three (3) strategies. (See, for example, FIG. 8, FIG. 9, and FIG. 10).

Accordingly, in some embodiments, the prodrug is a drug-lipid moiety comprising a PD-1 inhibitor of the disclosure.

In one embodiment, the prodrug comprises the following chemical structure denoted Formula I:

FORMULA I

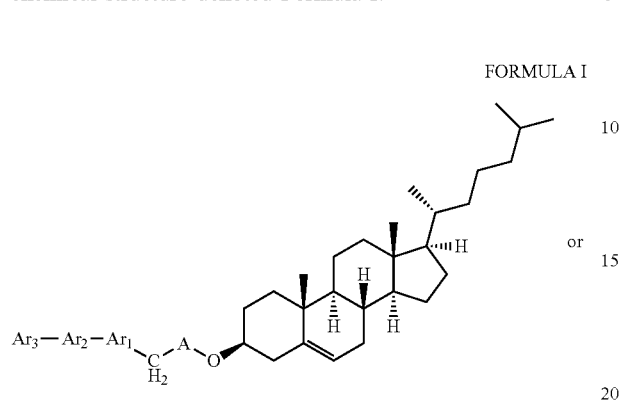

In one embodiment, the prodrug comprises the following chemical structure denoted Formula II:

FORMULA II

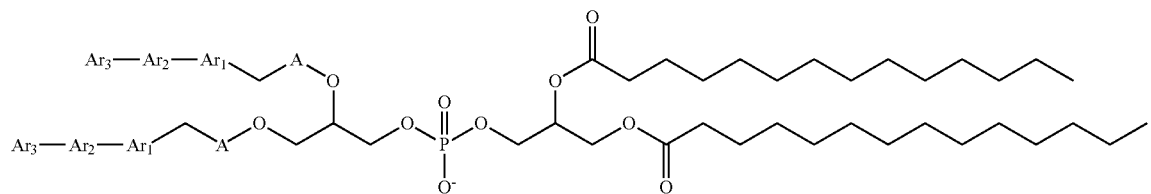

Wherein, in exemplary embodiments of FORMULA I and FORMULA II:

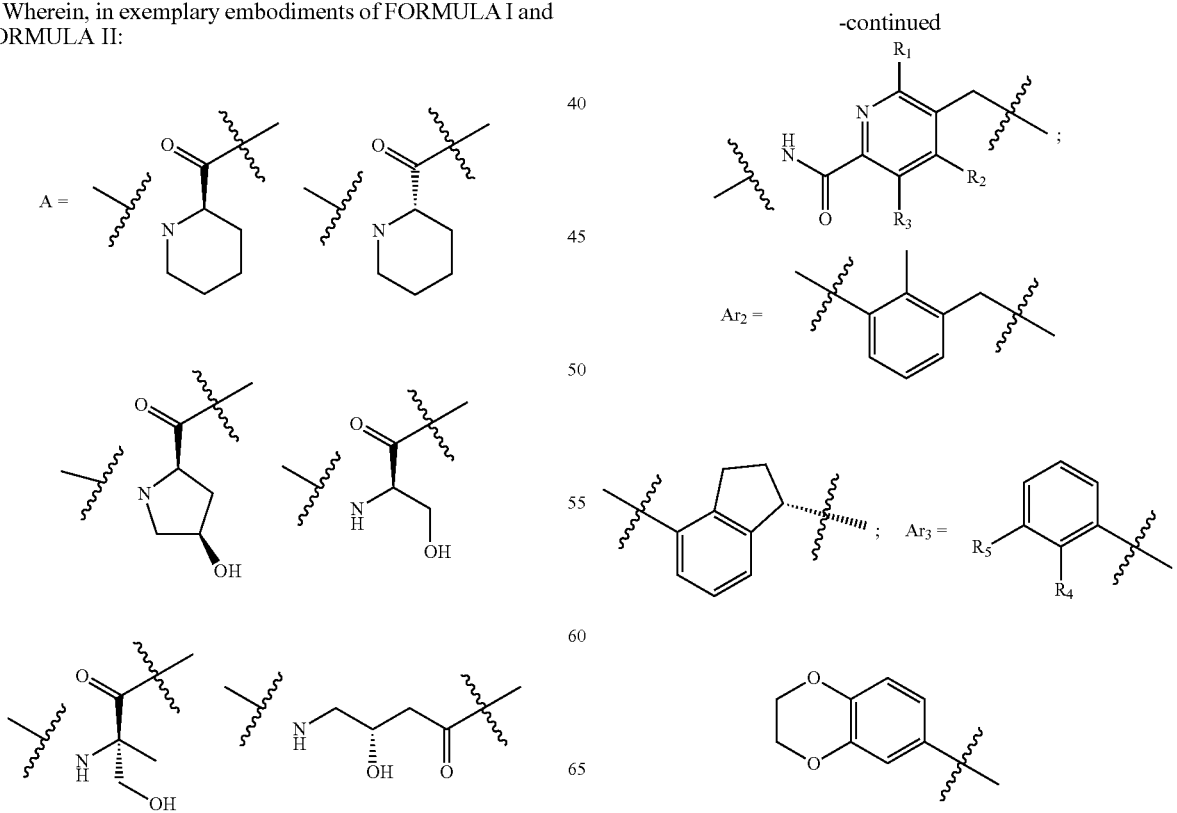

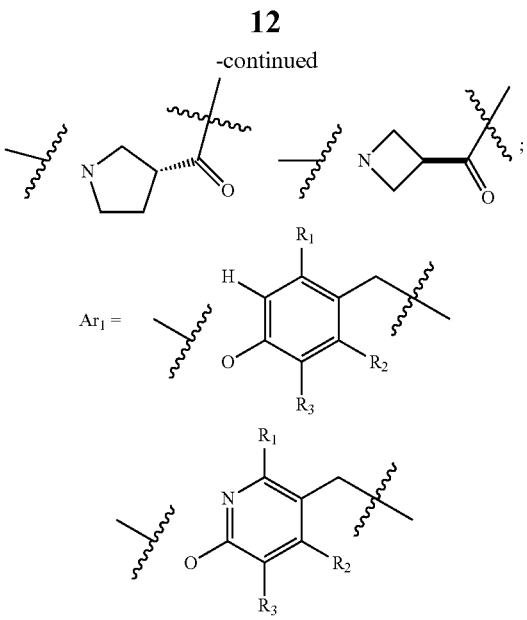

$R_1$ = H, OMe, $R_2$ = H, $R_3$ is H, Br, Cl;
$R_4$ is H, Cha, CL; and
$R_5$ is H, Thus, in embodiment, the prodrug is a drug-lipid moiety comprising a PD-1 inhibitor of FORMULA I.

Thus, in embodiment, the prodrug is a drug-lipid moiety comprising a PD-1 inhibitor of FORMULA II.

In embodiment, the prodrug is a drug-lipid moiety comprising a PD-1 inhibitor set forth in FIG. 8.

In embodiment, the prodrug is a drug-lipid moiety comprising a PD-1 inhibitor set forth in FIG. 9.

In embodiment, the prodrug is a drug-lipid moiety comprising a PD-1 inhibitor set forth in FIG. 10.

In a further embodiment, the PD-1 prodrug is a drug-lipid moiety comprising a lipid of the disclosure.

In a further embodiment, the PD-1 prodrug is a drug-lipid moiety comprising a LU of the disclosure.

In a further embodiment, the prodrug is a drug-lipid moiety comprising a PD-1 inhibitor of the invention, wherein the PD-1 comprises any one of the chemical compositions PD1-PD7.

In a further embodiment, the prodrug is a drug-lipid moiety comprising a PD-1 inhibitor of the invention, wherein the PD-1 inhibitor comprises any one of the chemical compositions PD1-PD7 and further comprises cholesterol.

In a further embodiment, the prodrug is a drug-lipid moiety comprising a PD-1 inhibitor of the invention, wherein the PD-1 inhibitor comprises any one of the chemical compositions PD1-PD7 and further comprises DPPG.

In a further embodiment, the prodrug is a drug-lipid moiety comprising a PD-1 inhibitor of the invention, wherein the PD-1 inhibitor comprises PD3 and further comprises cholesterol.

In a further embodiment, the prodrug is a drug-lipid moiety comprising a PD-1 inhibitor of the invention, wherein the PD-1 inhibitor comprises PD3 and further comprises cholesterol having the following chemical structure:

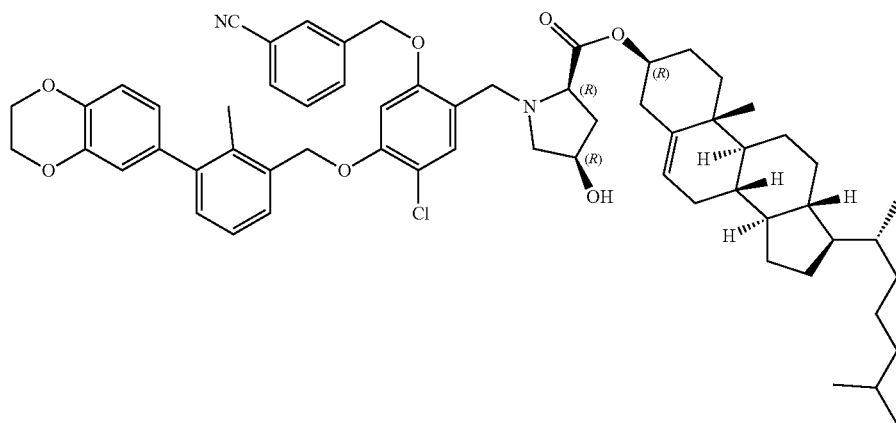

In a further embodiment, the prodrug is a drug-lipid moiety comprising a PD-1 inhibitor of the invention, wherein the PD-1 inhibitor comprises PD6 and further comprises cholesterol.

In a further embodiment, the prodrug is a drug-lipid moiety comprising a PD-1 inhibitor of the invention, wherein the PD-1 inhibitor comprises PD3 and further comprises DPPG.

In a further embodiment, the prodrug is a drug-lipid moiety comprising a PD-1 inhibitor of the invention, wherein the PD-1 inhibitor comprises PD6 and further comprises DPPG.

In a further embodiment, the prodrug is a drug-lipid moiety comprising a PD-1 inhibitor of the invention, wherein the PD-1 inhibitor comprises PD3 and further comprises cholesterol and whereby the LU is an esterase.

In a further embodiment, the prodrug is a drug-lipid moiety comprising a PD-1 inhibitor of the invention, wherein the PD-1 inhibitor comprises PD6 and further comprises cholesterol and whereby the LU is an ester.

In a further embodiment, the prodrug is a drug-lipid moiety comprising an PD-1 inhibitor of the invention, wherein the PD-1 inhibitor comprises PD1 and further comprises a lipid of the disclosure having the following chemical formula:

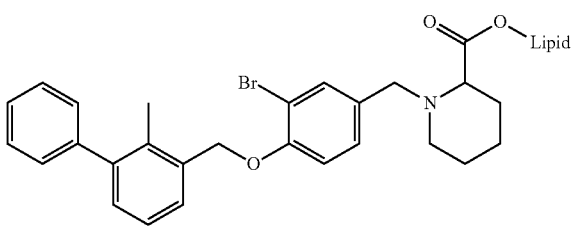

In a further embodiment, the prodrug is a drug-lipid moiety comprising an PD-1 inhibitor of the invention, wherein the PD-1 inhibitor comprises PD2 and further comprises a lipid of the disclosure having the following chemical formula:

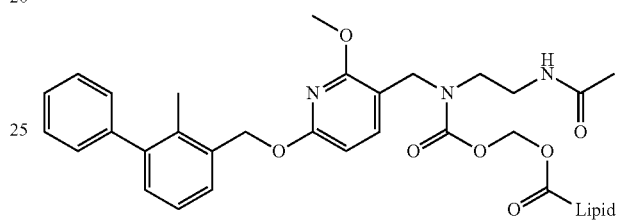

In a further embodiment, the prodrug is a drug-lipid moiety comprising an PD-1 inhibitor of the invention, wherein the PD-1 inhibitor comprises PD3 and further comprises a lipid of the disclosure having the following chemical formula:

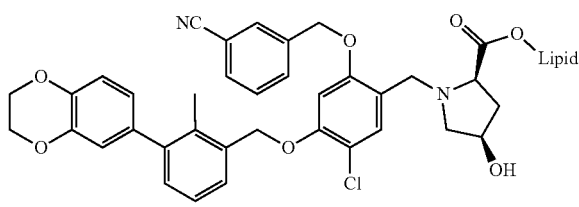

In a further embodiment, the prodrug is a drug-lipid moiety comprising an PD-1 inhibitor of the invention, wherein the PD-1 inhibitor comprises. PD4 and further comprises a lipid of the disclosure having the following chemical formula:

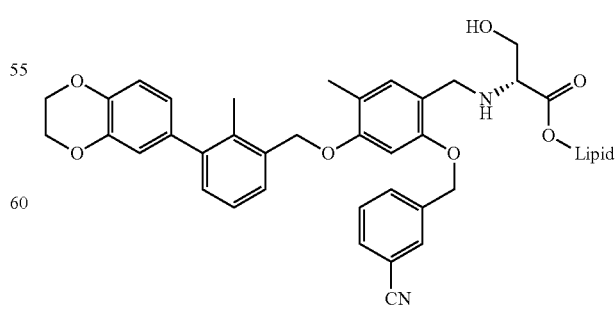

In a further embodiment, the prodrug is a drug-lipid moiety comprising an PD-1 inhibitor of the invention, wherein the PD-1 inhibitor comprises PD5 and further comprises a lipid of the disclosure having the following chemical formula:

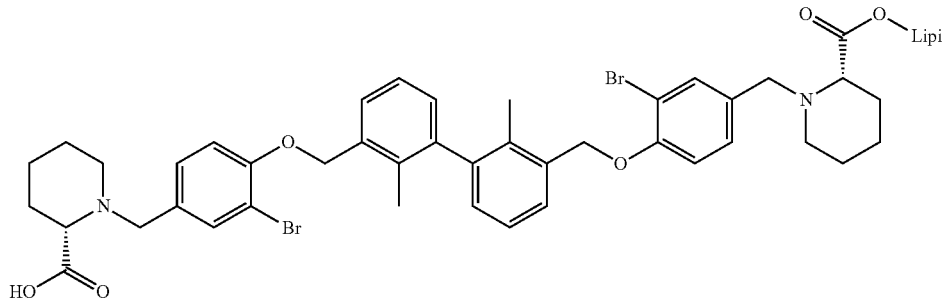

In a further embodiment, the prodrug is a drug-lipid moiety comprising an PD-1 inhibitor of the invention, wherein the PD-1 inhibitor comprises PD6 and further comprises a lipid of the disclosure having the following chemical formula:

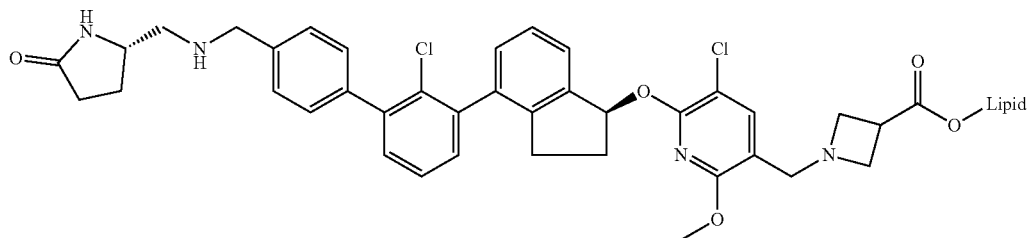

In a further embodiment, the prodrug is a drug-lipid moiety comprising an PD-1 inhibitor of the invention, wherein the PD-1 inhibitor comprises PD7 and further comprises a lipid of the disclosure having the following chemical formula:

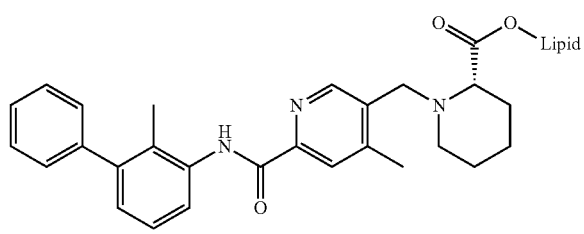

In additional embodiments of the disclosure the subject matter provides a PD-1 inhibitor prodrug comprising a lipid-conjugated therapeutic agent parent drug. In some embodiments, the prodrug comprises: (a) a monovalent drug moiety, (b) a monovalent lipid moiety, and (c) a bivalent linker moiety comprising a linkage unit that will degrade in vivo, such as a disulfide bond, wherein the monovalent drug moiety and the monovalent lipid moiety are linked (e.g., covalently linked) through the linker. The monovalent drug moiety and the monovalent lipid moieties can be monovalent derivatives of a chemical compound and a lipid, respectively. For instance, the monovalent derivative can be a deprotonated derivative of a chemical compound or lipid that comprises a hydroxyl, thiol, amino, or carboxylic acid group.

In further embodiments of the disclosure the subject matter provides a PD-1 inhibitor prodrug comprising a lipid-conjugated therapeutic agent parent drug. In some embodiments, the prodrug comprises: (a) a bivalent drug moiety, (b) a bivalent lipid moiety, and (c) a bivalent linker moiety comprising a linkage that will degrade in vivo, wherein the bivalent drug moiety and the bivalent lipid moiety are linked (e.g., covalently linked) through the linker.

The bivalent drug moiety and the bivalent lipid moieties can be bivalent derivatives of a chemical compound and a lipid, respectively. For instance, the bivalent derivative can be a deprotonated derivative of a chemical compound or lipid that comprises a hydroxyl, thiol, amino, or carboxylic acid group.

One of ordinary skill in the art will appreciate and be enabled to make variations and modifications to the disclosed embodiment without altering the function and purpose of the invention disclosed herein. Such variations and modifications are intended within the scope of the present disclosure.

III.) Drug Moieties

Another aspect of the invention provides for novel PD-1 prodrug compounds with the following formula(s) denoted PD1-PD7.

One of skill in the art will appreciate that a compound is useful as a PD-1 inhibitor (e.g., inhibits PD-1/L1 and/or L2). By way of brief background, immune checkpoints are known to contribute to tumor progression by enhancing cancer's ability to evade the immune system and metastasize. One of the most extensively studied immune checkpoints related to cancer is PD-1 and its ligands PD-L1 and PD-L2. This protein receptor, which is encoded by the Programmed Cell Death 1 gene on chromosome 2 and is a member of the CD28 superfamily, delivers inhibitory signals to adjacent cells upon interaction with its ligand. This checkpoint is critical in the regulation of T-cell activity, but PD-1 is only present on T-cells once they are activated. See, AGATA, et. al., Int. Immunol. (1996); vol. 8: pp. 765-772. PD-1, upon binding its ligands PD-1 (B7-H1) and PD-2 (B7-DC), helps exert immunoregulatory effects on T-cells by downregulating T-cell activity. Thus, PD-1 is a critical negative regulator of immunity that serves to identify and preserve "self" tissue. See, SMITH, et. al., Am. J. Transl. Res. (2019); 11(2): pp. 529-541.

Based on the foregoing, the present disclosure describes a class of PD-1 inhibitors.

In one embodiment, a drug moiety of the disclosure comprises a compound with the following chemical structure (denoted PD1):

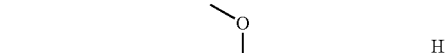

PD1

In a further embodiment, a drug moiety of the disclosure comprises a compound with the following chemical structure (denoted PD2):

PD2

In a further embodiment, a drug moiety of the disclosure comprises a compound with the following chemical structure (denoted PD3):

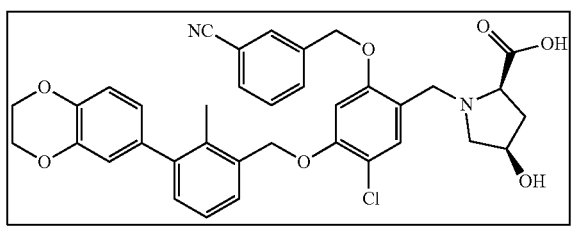 [SMILES: Cc1c(COc2cc(OCc3cccc(C#N)c3)c(CN3C[C@H](O)C[C@@H]3C(=O)O)cc2Cl)cccc1-c1ccc2c(c1)OCCO2]

In another embodiment, a drug moiety of the disclosure comprises a compound with the following chemical structure (denoted PD4):

PD4

In yet a further embodiment, a drug moiety of the disclosure comprises a compound with the following chemical structure (denoted PD5):

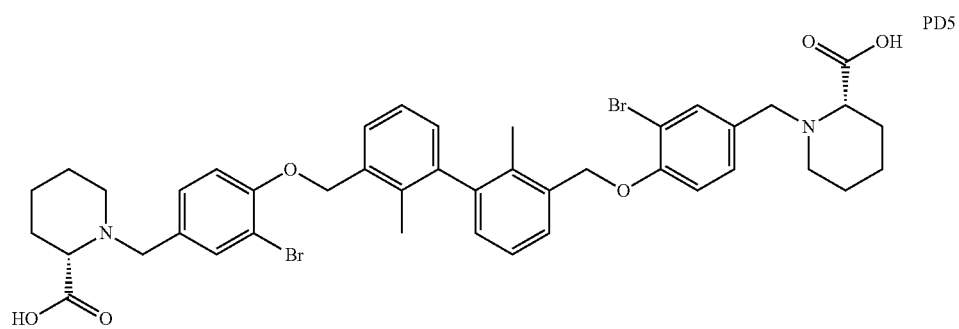 [SMILES: Cc1c(COc2ccc(CN3CCCC[C@H]3C(=O)O)cc2Br)cccc1-c1cccc(COc2ccc(CN3CCCC[C@H]3C(=O)O)cc2Br)c1C]

PD5

In a further embodiment, a drug moiety of the disclosure comprises a compound with the following chemical structure (denoted PD6):

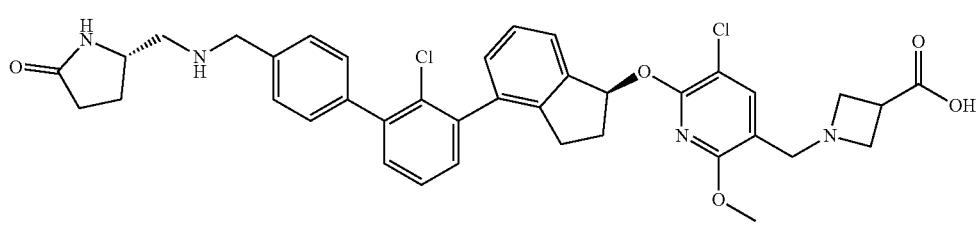

PD6

In a further embodiment, a drug moiety of the disclosure comprises a compound with the following chemical structure (denoted PD7):

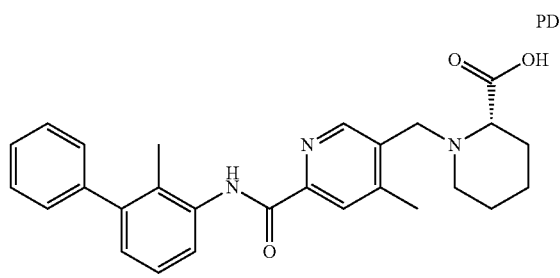

PD7

One of ordinary skill in the art will appreciate and be enabled to make variations and modifications to the disclosed embodiment without altering the function and purpose of the invention disclosed herein. Such variations and modifications are intended within the scope of the present disclosure.

IV.) Lipids

Generally speaking, and for the purposes of this disclosure, the term "lipid" is used in its broadest sense and comprises several sub-categories of lipids, including but not limited to, phospholipids I fatty acids. As it is appreciated by one of skill in the art, a phospholipid represents a class of lipids that are a major component of all cell membranes. Phospholipids can form lipid bilayers because of their amphiphilic characteristic. The structure of the phospholipid molecule generally consists of two hydrophobic fatty acid "tails" and a hydrophilic "head" consisting of a phosphate group that can be modified with simple organic molecules such as choline, ethanolamine, or serine. These two components are usually joined together by a glycerol molecule.

A representative list of phospholipids/fatty acid(s) of the invention are set forth in Table III.

By way of brief background, at the most fundamental level, the properties of a liposome depend upon the subtle physicochemical interactions among the various lipid species in its composition. Individual lipids can be combined to form a myriad of superstructures including bilayers, and bilayer properties can be tuned to modulate drug release and membrane stability. In a simplified bilayer model acyl chain length dictates bilayer thickness and phase transition temperature (Tm), acyl chain saturation controls bilayer fluidity, and headgroup interactions impact inter- and intra-lipid molecular forces. Liposome behavior can be adjusted by incorporating synthetic lipids such as lipid prodrugs, fusogenic lipids and functionalizable lipids into the bilayer. See, KOHLI, et. al., J. Control Release, 0: pp. 274-287 (Sep. 28, 2014).

In one embodiment of the present disclosure, a PD-1 prodrug comprises a monovalent lipid moiety.

In one embodiment, a PD-1 prodrug comprises a bivalent lipid moiety.

In one embodiment, the lipid comprises a cholesterol with the following chemical structure:

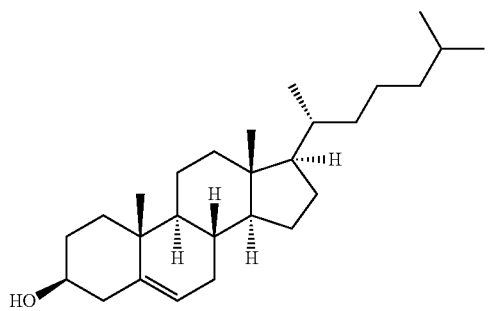

In one embodiment, the lipid comprises a DPPG with the following chemical structure:

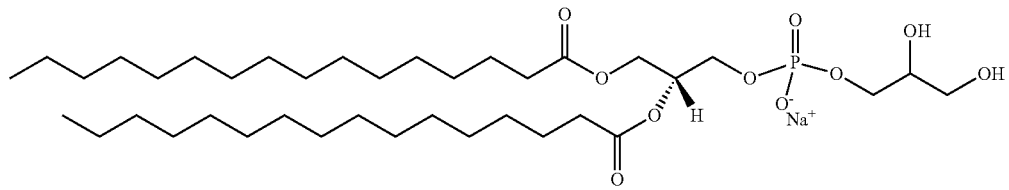 [SMILES: CCCCCCCCCCCCCCCC(=O)OC[C@H](COP(=O)([O-])OCC(O)CO)OC(=O)CCCCCCCCCCCCCCC ; [Na+]]

In one embodiment, the lipid comprises a DMPG with the following chemical structure:

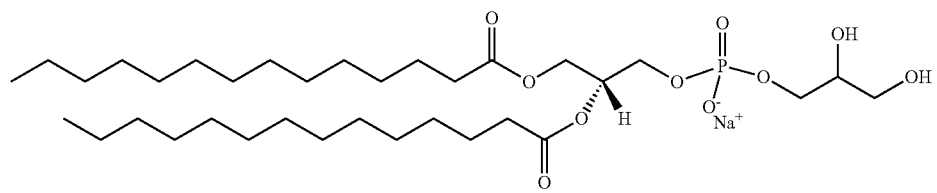 [SMILES: CCCCCCCCCCCCCC(=O)OC[C@H](COP(=O)([O-])OCC(O)CO)OC(=O)CCCCCCCCCCCCC ; [Na+]]

10

In one embodiment, the lipid comprises a Lyso PC with the following chemical structure:

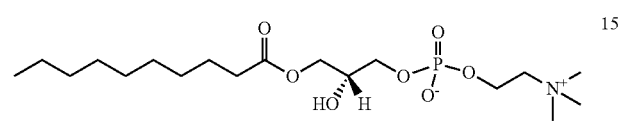

15

In one embodiment, the lipid comprises a (Δ9-Cis) PG with the following chemical structure:

20

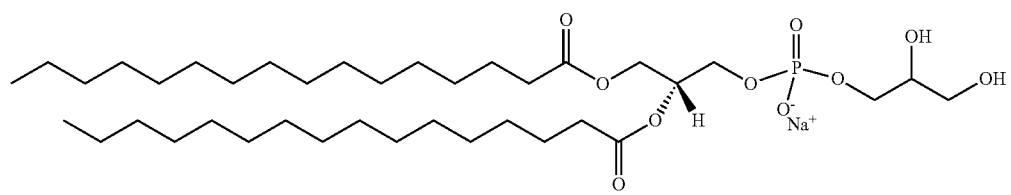 [SMILES: CCCCCCCCCCCCCCCC(=O)OC[C@H](COP(=O)([O-])OCC(O)CO)OC(=O)CCCCCCCCCCCCCCC ; [Na+]]

In one embodiment, the lipid comprises a Soy Lyso PC with the following chemical structure:

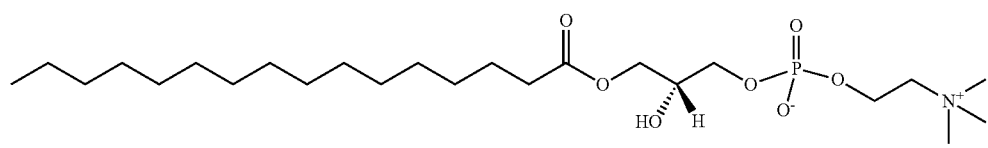 [SMILES: CCCCCCCCCCCCCCCC(=O)OC[C@@H](O)COP(=O)([O-])OCC[N+](C)(C)C]

In one embodiment, the lipid comprises a PG with the following chemical structure:

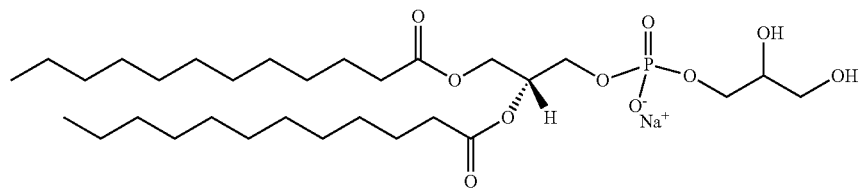 [SMILES: CCCCCCCCCCCC(=O)OC[C@H](COP(=O)([O-])OCC(O)CO)OC(=O)CCCCCCCCCCC ; [Na+]]

65

In one embodiment, the lipid comprises a C16 PEG2000 Ceramde with the following chemical structure:

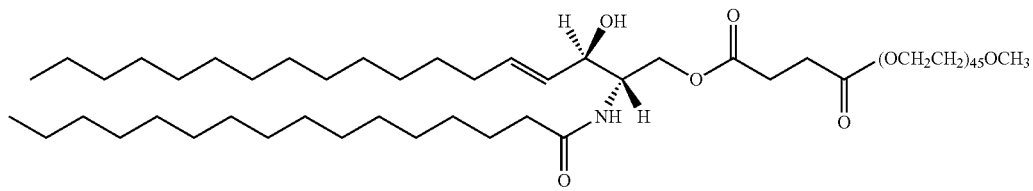

In one embodiment, the lipid comprises a cholesterol hemisuccinate ("CHEMS") with the following chemical structure:

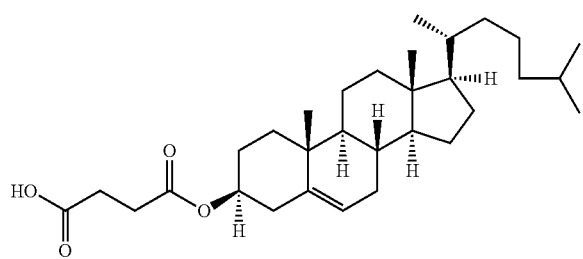

By way of reference, a complete list of the chemical formulas and abbreviation(s) of the lipids disclosed herein is set forth in Table I.

In an additional embodiment, the lipid comprises a phospholipid/fatty acid disclosed herein and set forth in Table III.

In a further embodiment, the lipid comprises Stearic Acid.

In addition, the PD-1 prodrugs and/or liposome(s) of the disclosure may comprise one or more helper lipids which are also referred to herein as "helper lipid components". The helper lipid components are preferably selected from the group comprising phospholipids and steroids. Phospholipids are preferably di- and monoester of the phosphoric acid. Preferred members of the phospholipids are phosphoglycerides and sphingolipids. Steroids, as used herein, are naturally occurring and synthetic compounds based on the partially hydrogenated cyclopenta[a]phenanthrene. Preferably, the steroids contain 21 to 30 C atoms. A particularly preferred steroid is cholesterol.

It is to be noted that although not wishing to be bound by any theory, due to the particular mol percentages of the helper lipid(s) contained in the lipid compositions according to the present invention, which helper lipid can be either a PEG-free helper lipid or in particular a PEG-containing helper lipid, surprising effects can be realized, more particularly if the content of any of this kind of helper lipid is contained within the concentration range specified herein.

In a further aspect of the present invention, lipid compositions which are preferably present as lipoplexes or liposomes, preferably show a neutral or overall anionic charge. The anionic lipid is preferably any neutral or anionic lipid described herein. The lipid composition comprises in a preferred embodiment any helper lipid or helper lipid combination as well as any PD-1 inhibitor as described herein (for example, PD3). In a further embodiment the composition according to the present invention containing nucleic acid(s) forms lipoplexes. In a preferred embodiment the term lipoplexes as used herein refers to a composition composed of neutral or anionic lipid, neutral helper lipid and PD-1 inhibitor of the invention. For reference into the usage of helper lipids in the art, see, by way of example, U.S. Patent Application Publication 2011/0178164; OJEDA, et. al., Int. J. of Pharmaceutics (March 2016); DABKOWSKA, et. al., J. R. Soc. Interface 9, pp. 548-561 (2012); and MOCHIZUKI, et. al., Biochimica et. Biophysica Acta, 1828, pp. 412-418 (2013).

In a preferred embodiment, the helper lipids of the invention comprise the helper lipids set forth in Table II.

In one embodiment, a PD-1 prodrug comprises a lipid of the invention, wherein the lipid is cholesterol and wherein the drug moiety is PD1.

In one embodiment, a PD-1 prodrug comprises a lipid of the invention, wherein the lipid is cholesterol and wherein the drug moiety is PD2.

In one embodiment, a PD-1 prodrug comprises a lipid of the invention, wherein the lipid is cholesterol and wherein the drug moiety is PD3.

In one embodiment, a PD-1 prodrug comprises a lipid of the invention, wherein the lipid is cholesterol and wherein the drug moiety is PD4.

In one embodiment, a PD-1 prodrug comprises a lipid of the invention, wherein the lipid is cholesterol and wherein the drug moiety is PD5.

In one embodiment, a PD-1 prodrug comprises a lipid of the invention, wherein the lipid is cholesterol and wherein the drug moiety is PD6.

In one embodiment, a PD-1 prodrug comprises a lipid of the invention, wherein the lipid is cholesterol and wherein the drug moiety is PD7. In one embodiment, a PD-1 prodrug comprises a lipid of the invention, wherein the lipid is cholesterol and wherein the drug moiety is PD3 and wherein the PD Prodrug has the following chemical structure:

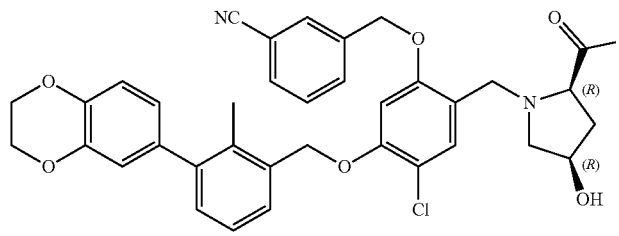
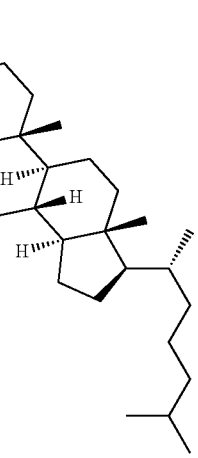

In one embodiment, a PD-1 prodrug comprises a lipid of the invention, wherein the lipid is cholesterol and wherein the drug moiety is any one of PD1-P7, further comprising a LU and wherein the LU is an ester.

In one embodiment, a PD-1 prodrug comprises a lipid of the invention, wherein the lipid is cholesterol and wherein the drug moiety is any one of PD1-P7, further comprising a LU and wherein the LU is an ester, further comprising a helper lipid component, wherein the helper lipid component comprises a helper lipid of Table II.

In one embodiment, a PD-1 prodrug comprises a lipid of the invention, wherein the lipid is DPPG and wherein the drug moiety is PD1.

In one embodiment, a PD-1 prodrug comprises a lipid of the invention, wherein the lipid is DPPG and wherein the drug moiety is PD2.

In one embodiment, a PD-1 prodrug comprises a lipid of the invention, wherein the lipid is DPPG and wherein the drug moiety is PD3.

In one embodiment, a PD-1 prodrug comprises a lipid of the invention, wherein the lipid is DPPG and wherein the drug moiety is PD4.

In one embodiment, a PD-1 prodrug comprises a lipid of the invention, wherein the lipid is DPPG and wherein the drug moiety is PD5.

In one embodiment, a PD-1 prodrug comprises a lipid of the invention, wherein the lipid is DPPG and wherein the drug moiety is PD6.

In one embodiment, a PD-1 prodrug comprises a lipid of the invention, wherein the lipid is DPPG and wherein the drug moiety is PD7.

In one embodiment, a PD-1 prodrug comprises a lipid of the invention, wherein the lipid is DPPG and wherein the drug moiety is any one of PD1-PD7 and wherein the DPPG is monovalent or bivalent (i.e., each Prodrug comprises a lipid and either 1 or 2 drug molecules).

In one embodiment, a PD-1 prodrug comprises a lipid of the invention, wherein the lipid is DPPG and wherein the drug moiety is any one of PD1-P7, further comprising a LU and wherein the LU is an ester.

In one embodiment, a PD-1 prodrug comprises a lipid of the invention, wherein the lipid is DPPG and wherein the chemical composition is any one of PD1-P7, further comprising a LU and wherein the LU is an ester, further comprising a helper lipid component, wherein the helper lipid component comprises a helper lipid of Table II.

One of ordinary skill in the art will appreciate and be enabled to make variations and modifications to the disclosed embodiment without altering the function and purpose of the invention disclosed herein. Such variations and modifications are intended within the scope of the present disclosure.

V.) Linkage Unit(s) ("LU")

In some embodiments, the presently disclosed subject matter provides prodrugs comprising drug-lipid conjugates that include biodegradable linkages, such as esters, thioesters, and other linkers known in the art.

Exemplary embodiments of ester chemistry are set forth herein:

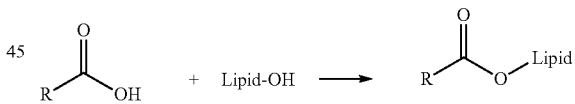

In some embodiments, the prodrug is a drug-lipid conjugate, whereby the drug-lipid conjugate is cleaved by an esterase.

In one embodiment, a prodrug of the invention comprises a LU via a secondary amine, amide, or aniline using the following schema:

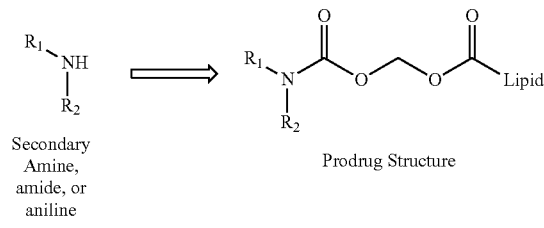

Secondary Amine, amide, or aniline

Prodrug Structure

An exemplary synthesis is as follows:

Synthesis

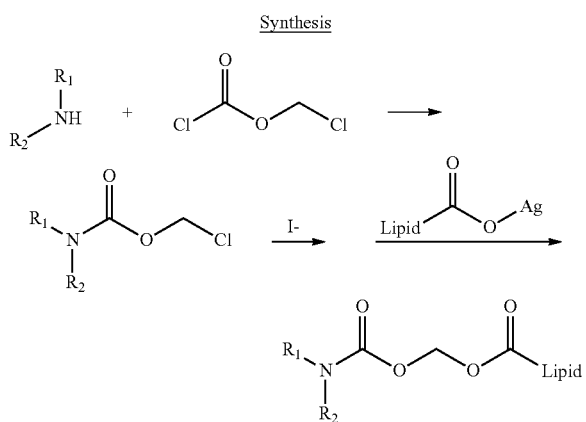

Cleavage of the prodrug structure comprising a secondary amine, amide, or aniline is obtained via esterase hydrolysis of the secondary amine, amide, or aniline prodrug under the following exemplary synthesis:

Esterase Hydrolysis of Secondary Predrug

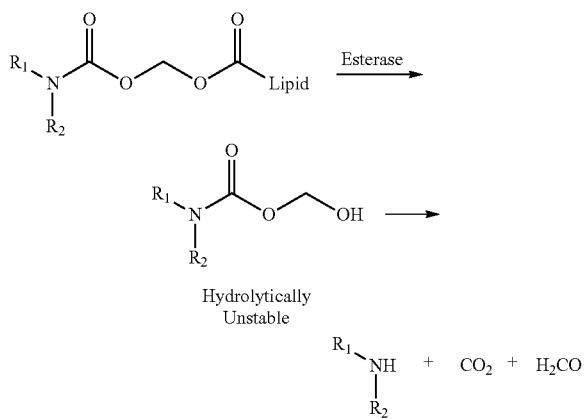

Wherein:

$R_1$—NH—$R_2$ can be any molecule with a secondary amine, amide, or aniline.

In one embodiment, the secondary amide nitrogen of the PD3 drug moiety is conjugated to cholesterol via a hydromethylcarbamate linker.

One of ordinary skill in the art will appreciate and be enabled to make variations and modifications to the disclosed embodiment without altering the function and purpose of the invention disclosed herein. Such variations and modifications are intended within the scope of the present disclosure.

VI.) Nanocarrier(s)

Generally speaking, and for the purposes of this disclosure nanocarrier(s) are within the scope of the invention. A nanocarrier is nanomaterial being used as a transport module for another substance, such as a drug. Commonly used nanocarriers include micelles, polymers, carbon-based materials, liposomes, and other substances. Because of their small size, nanocarriers can deliver drugs to otherwise inaccessible sites around the body. Nanocarriers can include polymer conjugates, polymeric nanoparticles, lipid-based carriers, dendrimers, carbon nanotubes, and gold nanoparticles. Lipid-based carriers include liposomes, solid-lipid nanoparticles, and micelles. In certain embodiments the nanocarrier is a liposome, lipid nanoparticle ("LNP") or a solid-lipid nanoparticle ("SLNP").

In addition, nanocarriers are useful in the drug delivery process because they can deliver drugs to site-specific targets, allowing drugs to be delivered in certain organs or cells but not in others. Site-specificity poses a major therapeutic benefit since it prevents drugs from being delivered to the wrong places. In addition. nanocarriers show promise for use in chemotherapy because they can help decrease the adverse, broader-scale toxicity of chemotherapy on healthy, fast-growing cells around the body. Since chemotherapy drugs can be extremely toxic to human cells, it is important that they are delivered to the tumor without being released into other parts of the body.

Generally speaking, there are four (4) methods in which nanocarriers can deliver drugs and they include passive targeting, active targeting, pH specificity, and temperature specificity.

Passive targeting refers to a nanocarrier's ability to travel down a tumor's vascular system, become trapped, and accumulate in the tumor. This accumulation is caused by the enhanced permeability and retention effect. The leaky vasculature of a tumor is the network of blood vessels that form in a tumor, which contain many small pores. These pores allow nanocarriers in, but also contain many bends that allow the nanocarriers to become trapped. As more nanocarriers become trapped, the drug accumulates at the tumor site. This accumulation causes large doses of the drug to be delivered directly to the tumor site.

Active targeting involves the incorporation of targeting modules such as ligands or antibodies on the surface of nanocarriers that are specific to certain types of cells around the body. Generally, nanocarriers have a high surface-area to volume ratio allowing for multiple ligands to be incorporated on their surfaces.

Additionally, certain nanocarriers will only release the drugs they contain in specific pH ranges. pH specificity also allows nanocarriers to deliver drugs directly to a tumor site. This is due to the fact that tumors are generally more acidic than normal human cells, with a pH around 6.8. Normal tissue has a pH of around 7.4. Thus, nanocarriers that only release drugs at certain pH ranges can therefore be used to release the drug only within acidic tumor environments. High acidic environments cause the drug to be released due to the acidic environment degrading the structure of the nanocarrier. Generally, these nanocarriers will not release drugs in neutral or basic environments, effectively targeting the acidic environments of tumors while leaving normal body cells untouched. This pH sensitivity can also be induced in micelle systems by adding copolymer chains to micelles that have been determined to act in a pH independent manor. See, W U, et. al., Biomaterials, 34(4): 1213-1222 (2012). These micelle-polymer complexes also help to prevent cancer cells from developing multi-drug resistance. The low pH environment triggers a quick release of the micelle polymers, causing a majority of the drug to be released at once, rather than gradually like other drug treatments.

Additionally, some nanocarriers have also been shown to deliver drugs more effectively at certain temperatures. Since tumor temperatures are generally higher than temperatures throughout the rest of the body, around 40° C., this temperature gradient helps act as safeguard for tumor-specific site delivery. See, REZAEI, et. al., Polymer, 53(16): 3485-3497 (2012).

As disclosed herein, lipid-based nanocarriers, such as liposomes are within the scope of this invention. Lipid-based nanoparticles (LBNPs or LNPs) such as liposomes, solid-lipid nanoparticles (SLNPs) and nanostructured lipid carriers (NLC) can transport hydrophobic and hydrophilic molecules, display very low or no toxicity, and increase the time of drug action by means of a prolonged half-life and a controlled release of the drug. Lipid nanoparticles can include chemical modifications to avoid the detection by the immune system (gangliosides or polyethylene glycol (PEG)) or to improve the solubility of the drug. In addition, they can be prepared in formulations sensitive to the pH in order to promote drug release in an acid environment and can also be associated with small molecules or antibodies that recognize tumor cells or their receptors (such as folic acid (FoA)). Nanodrugs can also be used in combination with other therapeutic strategies to improve the response of patients. See, GARCIA-PINEL, et. al., Nanomaterials 9(639) (2019).

In various embodiments silicasome drug carriers described herein comprise a porous silica (or other material) nanoparticle (e.g., a silica body having a surface and defining a plurality of pores that are suitable to receive molecules therein) coated with a lipid bilayer. The fact that the nanoparticle is referred to as a silica nanoparticle does not preclude materials other than silica from also being incorporated within the silica nanoparticle. In some embodiments, the silica nanoparticle may be substantially spherical with a plurality of pore openings through the surface providing access to the pores. However, in various embodiments the silica nanoparticle can have shapes other than substantially spherical shapes. Thus, for example, in certain embodiments the silica nanoparticle can be substantially ovoid, rod-shaped, a substantially regular polygon, an irregular polygon, and the like.

Generally, the silica nanoparticle comprises a silica body that defines an outer surface between the pore openings, as well as side walls within the pores. The pores can extend through the silica body to another pore opening, or a pore can extend only partially through the silica body such that that it has a bottom surface of defined by the silica body.

In some embodiments, the silica body is mesoporous. In other embodiments, the silica body is microporous. As used herein, "mesoporous" means having pores with a diameter between about 2 nm and about 50 nm, while "microporous" means having pores with a diameter smaller than about 2 nm. In general, the pores may be of any size, but in typical embodiments are large enough to contain one or more therapeutic compounds therein. In such embodiments, the pores allow small molecules, for example, therapeutic compounds such as anticancer compounds to adhere or bind to the inside surface of the pores, and to be released from the silica body when used for therapeutic purposes. In some embodiments, the pores are substantially cylindrical.

In certain embodiments the nanoparticles comprise pores having pore diameters between about 1 nm and about 10 nm in diameter or between about 2 nm and about 8 nm. In certain embodiments the nanoparticles comprise pores having pore diameters between about 1 nm and about 6 nm, or between about 2 nm and about 5 nm. Other embodiments include particles having pore diameters less than 2.5 nm.

In other embodiments, the pore diameters are between 1.5 and 2.5 nm. Silica nanoparticles having other pore sizes may be prepared, for example, by using different surfactants or swelling agents during the preparation of the silica nanoparticles. In various embodiments the nanoparticles can include particles as large (e.g., average or median diameter (or another characteristic dimension) as about 1000 nm. However, in various embodiments the nanoparticles are typically less than 500 nm or less than about 300 nm as, in general, particles larger than 300 nm may be less effective in entering living cells or blood vessel fenestrations. In certain embodiments the nanoparticles range in size from about 40 nm, or from about 50 nm, or from about 60 nm up to about 100 nm, or up to about 90 nm, or up to about 80 nm, or up to about 70 nm. In certain embodiments the nanoparticles range in size from about 60 nm to about 70 nm. Some embodiments include nanoparticles having an average maximum dimension between about 50 nm and about 1000 nm. Other embodiments include nanoparticles having an average maximum dimension between about 50 nm and about 500 nm. Other embodiments include nanoparticles having an average maximum dimension between about 50 nm and about 200 nm.

In some embodiments, the average maximum dimension is greater than about 20 nm, greater than about 30 nm, greater than 40 nm, or greater than about 50 nm. Other embodiments include nanoparticles having an average maximum dimension less than about 500 nm, less than about 300 nm, less than about 200 nm, less than about 100 nm or less than about 75 nm. As used herein, the size of the nanoparticle refers to the average or median size of the primary particles, as measured by transmission electron microscopy (TEM) or similar visualization techniques known in the art. Further examples of mesoporous silica nanoparticles include, but are not limited to, MCM-41, MCM-48, and SBA-15. See, KATIYARE, et. al., J. Chromotog. 1122(1-2): 13-20 (2006).

Methods of making porous silica nanoparticles are well known to those of skill in the art. In certain embodiments mesoporous silica nanoparticle are synthesized by reacting tetraethyl orthosilicate (TEOS) with a template made of micellar rods. The result is a collection of nano-sized spheres or rods that are filled with a regular arrangement of pores. The template can then be removed by washing with a solvent adjusted to the proper pH (See, e.g., TREWYN et al. (2007) Chem. Eng. J. 137(1): 23-29).

In certain embodiments mesoporous particles can also be synthesized using a simple sol-gel method (See, e.g., NANDIYANTO, et al. (2009) Microporous and Mesoporous Mat. 120(3): 447-453). In certain embodiments tetraethyl orthosilicate can also be used with an additional polymer monomer as a template. In certain embodiments 3-mercaptopropyl)trimethoxysilane (MPTMS) is used instead of TEOS.

In certain embodiments the mesoporous silica nanoparticles are cores are synthesized by a modification of the sol/gel procedure described by MENG et. al. (2015) ACS Nemo, 9(4): 3540-3557.

While the methods described herein have been demonstrated with respect to porous silica nanoparticles (e.g., mesoporous silica), it will be recognized by those skilled in the art that similar methods can be used with other porous nanoparticles. Numerous other mesoporous materials that can be used in drug delivery nanoparticles are known to those of skill in the art. For example, in certain embodiments mesoporous carbon nanoparticles could be utilized.

Mesoporous carbon nanoparticles are well known to those of skill in the art (See, e.g., HUANG et. al. (2016) Carbon, 101: 135-142; ZHU et. al. (2014) Asian J. Pharm. Sci., 9(2): 82-91; and the like).

Similarly, in certain embodiments, mesoporous polymeric particles can be utilized. The syntheses of highly ordered mesoporous polymers and carbon frameworks from organic-organic assembly of triblock copolymers with soluble, low-molecular-weight phenolic resin precursors (resols) by an evaporation induced self-assembly strategy have been reported by MENG, et. al. (2006) Chem. Mat. 6(18): 4447-4464.

The nanoparticles described herein are illustrative and non-limiting. Using the teachings provided herein numerous other lipid bilayer coated nanoparticles will be available to one of skill in the art.

In one embodiment, the invention teaches a nanocarrier comprising a PD-1 inhibitor.

In one embodiment, the invention teaches nanocarriers which comprise PD-1 Prodrugs.

In one embodiment, the invention teaches a nanocarrier comprising a liposome, wherein the lipid comprises cholesterol.

In one embodiment, the invention teaches a nanocarrier comprising a liposome, wherein the lipid comprises DPPG.

In one embodiment, the invention teaches a nanocarrier comprising a liposome, wherein the lipid comprises cholesterol and whereby the liposome further comprises a PD-1 Prodrug.

In one embodiment, the invention teaches a nanocarrier comprising a liposome, wherein the lipid comprises cholesterol and whereby the liposome further comprises PD1.

In one embodiment, the invention teaches a nanocarrier comprising a liposome, wherein the lipid comprises cholesterol and whereby the liposome further comprises PD2.

In one embodiment, the invention teaches a nanocarrier comprising a liposome, wherein the lipid comprises cholesterol and whereby the liposome further comprises PD3.

In one embodiment, the invention teaches a nanocarrier comprising a liposome, wherein the lipid comprises cholesterol and whereby the liposome further comprises PD3 (denoted LNP-PD3).

In one embodiment, the invention teaches a nanocarrier comprising a liposome, wherein the lipid comprises cholesterol and whereby the liposome further comprises PD4.

In one embodiment, the invention teaches a nanocarrier comprising a liposome, wherein the lipid comprises cholesterol and whereby the liposome further comprises PD5.

In one embodiment, the invention teaches a nanocarrier comprising a liposome, wherein the lipid comprises cholesterol and whereby the liposome further comprises PD6.

In one embodiment, the invention teaches a nanocarrier comprising a liposome, wherein the lipid comprises cholesterol and whereby the liposome further comprises PD7.

In one embodiment, the invention teaches a nanocarrier comprising a liposome, wherein the lipid comprises DPPG and whereby the liposome further comprises a PD-1 inhibitor.

In one embodiment, the invention teaches a nanocarrier comprising a liposome, wherein the lipid comprises DPPG and whereby the liposome further comprises PD1.

In one embodiment, the invention teaches a nanocarrier comprising a liposome, wherein the lipid comprises DPPG and whereby the liposome further comprises PD2.

In one embodiment, the invention teaches a nanocarrier comprising a liposome, wherein the lipid comprises DPPG and whereby the liposome further comprises PD3.

In one embodiment, the invention teaches a nanocarrier comprising a liposome, wherein the lipid comprises DPPG and whereby the liposome further comprises PD4.

In one embodiment, the invention teaches a nanocarrier comprising a liposome, wherein the lipid comprises DPPG and whereby the liposome further comprises PD5.

In one embodiment, the invention teaches a nanocarrier comprising a liposome, wherein the lipid comprises DPPG and whereby the liposome further comprises PD6.

In one embodiment, the invention teaches a nanocarrier comprising a liposome, wherein the lipid comprises DPPG and whereby the liposome further comprises PD7.

In one embodiment, the invention teaches a nanocarrier comprising a solid-lipid nanoparticle (SLNP) comprising a PD-1 inhibitor.

In one embodiment, the invention teaches a nanocarrier comprising a solid-lipid nanoparticle (SLNP) comprising a PD-1-Prodrug.

In one embodiment, the invention teaches a nanocarrier comprising a solid-lipid nanoparticle (SLNP), whereby the lipid is cholesterol and whereby the SLNP further comprises PD1.

In one embodiment, the invention teaches a nanocarrier comprising a solid-lipid nanoparticle (SLNP), whereby the lipid is cholesterol and whereby the SLNP further comprises PD2.

In one embodiment, the invention teaches a nanocarrier comprising a solid-lipid nanoparticle (SLNP), whereby the lipid is cholesterol and whereby the SLNP further comprises PD3.

In one embodiment, the invention teaches a nanocarrier comprising a solid-lipid nanoparticle ("SLNP"), wherein the solid-lipid nanoparticle comprises cholesterol and whereby the solid-lipid nanoparticle further comprises PD3 (denoted SLNP-PD3).

In a further embodiment, the invention teaches a nanocarrier comprising a solid-lipid nanoparticle ("SLNP"), wherein the solid-lipid nanoparticle comprises cholesterol and whereby the solid-lipid nanoparticle further comprises PD3 and whereby the SLNP is co-formulated with TR5 (denoted SLNP-PD3-TR5).

In a further embodiment, the invention teaches a nanocarrier comprising a solid-lipid nanoparticle ("SLNP"), wherein the solid-lipid nanoparticle comprises cholesterol and whereby the solid-lipid nanoparticle further comprises PD3 and whereby the SLNP is co-formulated with AR5 (denoted SLNP-PD3-AR5).

In a further embodiment, the invention teaches a nanocarrier comprising a solid-lipid nanoparticle ("SLNP"), wherein the solid-lipid nanoparticle comprises cholesterol and whereby the solid-lipid nanoparticle further comprises PD3 and whereby the SLNP is co-formulated with AR5 and further whereby the SLNP is co-formulated with doxorubicin (DOX) (denoted SLNP-PD3-AR5-DOX).

In one embodiment, the invention teaches a nanocarrier comprising a solid-lipid nanoparticle (SLNP), whereby the lipid is cholesterol and whereby the SLNP further comprises PD4.

In one embodiment, the invention teaches a nanocarrier comprising a solid-lipid nanoparticle (SLNP), whereby the lipid is cholesterol and whereby the SLNP further comprises PD5.

In one embodiment, the invention teaches a nanocarrier comprising a solid-lipid nanoparticle (SLNP), whereby the lipid is cholesterol and whereby the SLNP further comprises PD6.

In one embodiment, the invention teaches a nanocarrier comprising a solid-lipid nanoparticle (SLNP), whereby the lipid is cholesterol and whereby the SLNP further comprises PD7.

In one embodiment, the invention teaches a nanocarrier comprising a solid-lipid nanoparticle (SLNP), whereby the lipid is DPPG and whereby the SLNP further comprises PD1.

In one embodiment, the invention teaches a nanocarrier comprising a solid-lipid nanoparticle (SLNP), whereby the lipid is DPPG and whereby the SLNP further comprises PD2.

In one embodiment, the invention teaches a nanocarrier comprising a solid-lipid nanoparticle (SLNP), whereby the lipid is DPPG and whereby the SLNP further comprises PD3.

In one embodiment, the invention teaches a nanocarrier comprising a solid-lipid nanoparticle (SLNP), whereby the lipid is DPPG and whereby the SLNP further comprises PD4.

In one embodiment, the invention teaches a nanocarrier comprising a solid-lipid nanoparticle (SLNP), whereby the lipid is DPPG and whereby the SLNP further comprises PD5.

In one embodiment, the invention teaches a nanocarrier comprising a solid-lipid nanoparticle (SLNP), whereby the lipid is DPPG and whereby the SLNP further comprises PD6.

In one embodiment, the invention teaches a nanocarrier comprising a solid-lipid nanoparticle (SLNP), whereby the lipid is DPPG and whereby the SLNP further comprises PD7.

In a further preferred embodiment, the solid-lipid nanoparticle of the invention comprises a composition having the following ratio(s):

| Constituent of the SLNP | Amount (% w/w) |
| --- | --- |
| Lipid 1 (lipid-prodrug) | 1-95 |
| Lipid 2 (lipid-prodrug) | 0-40 |
| Helper lipids | 0-80 |
| DSPE-PEG2000 | 0-10 |
| Stabilizer(s) | 0.5-20 |

Whereby Lipid 1 comprises a PD-1-Prodrug, wherein the lipid moiety comprises cholesterol and whereby the helper lipids are the helper lipids set forth in Table II and whereby the stabilizers are selected from the group consisting of polyvinyl alcohol (e.g., Moliwol 488), poloxamers (e.g., Pluronic F127), Tween 80, PEG, cyclodextrin, and Kolliphor RH 40 and whereby Lipid 2 (lipid prodrug) comprises a lipid prodrug of the disclosure or a lipid prodrug selected from the group consisting of AR5, TR5 inhibitors (for examples ID3-STEA, ID3-CHEM, AR5-STEA, TR3-STEA, ID1-CHOL, etc.), MPLA, and Telratolimod.

In a further preferred embodiment, the solid-lipid nanoparticle of the invention comprises a composition having the following ratio(s):

| Constituent of the SLNP | Amount (% w/w) |
| --- | --- |
| Lipid 1 (lipid-prodrug) | 1-95 |
| Lipid 2 (lipid-prodrug) | 0-40 |
| Helper lipids | 0-80 |
| DSPE-PEG2000 | 0-10 |
| Stabilizer(s) | 0.5-20 |

Whereby Lipid 1 comprises a PD3-Prodrug, wherein the lipid moiety comprises cholesterol and whereby the helper lipids are the helper lipids set forth in Table II and whereby the stabilizers are selected from the group consisting of polyvinyl alcohol (e.g., Moliwol 488), poloxamers (e.g., Pluronic F127), Tween 80, PEG, cyclodextrin, and Kolliphor RH 40 and whereby Lipid 2 (lipid prodrug) comprises a lipid prodrug of the disclosure or a lipid prodrug selected from the group consisting of AR5, TR5 inhibitors (for examples ID3-STEA, ID3-CHEM, AR5-STEA, TR3-STEA, ID1-CHOL, etc.), MPLA, and Telratolimod.

One of ordinary skill in the art will appreciate and be enabled to make variations and modifications to the disclosed embodiment without altering the function and purpose of the invention disclosed herein. Such variations and modifications are intended within the scope of the present disclosure.

The scope of the disclosure teaches three (3) possible treatment modalities using the formulated prodrugs of the invention. See, PCT Patent Publication No. WO2018/213631.

The first treatment modality involves combination of an PD-1 prodrug in combination with another therapeutic (e.g., another formulated prodrug which inhibits PD-1/L1/L2, a chemotherapy agent (such as an ICD-inducing chemotherapy), etc.) into a single liposome that allows systemic (or local) biodistribution and drug delivery to tumor sites. The dual-delivery approach achieved synergistic enhancement of adaptive and innate immunity, leading to a significant improvement in animal survival. In certain embodiments the nanocarrier comprises a vesicle (i.e., a lipid bilayer enclosing a fluid).

A second treatment modality involves local delivery to a tumor or peri-tumoral region, of an agent that inhibits PD-1/L1/L2 in combination with a lipid (e.g., a liposome) that comprises an inhibitor of PD-1/L1/L2. It is demonstrated that such local delivery of a PD-1/L1/L2 inhibitor in combination with a PD-1 prodrug induces cytotoxic tumor killing, and tumor shrinkage at the local site. These adaptive immune responses are accompanied by boosting of the innate immune system, as reflected by CRT expression, as well as the activation of a DC population, particularly well-suited for generating cytotoxic T cell responses.

A third treatment modality involves vaccination utilizing dying cancer cells {e.g., KPC cells) in which inhibition of PD-1/L1/L2 is induced ex vivo. It is discovered that such vaccination can generate a systemic immune response that can interfere with tumor growth at a remote site as well as allowing adoptive transfer to non-immune animals. One of skill in the art will appreciate and be enabled to perform methods the treatment modalities provided herein.

VII.) Liposomes

In one aspect, the presently disclosed subject matter is based on an approach for providing a prodrug of the disclosure (See, section entitled Prodrugs) suitable for incorporation into a nanocarrier comprising lipid coating layers to provide enhanced delivery of the corresponding prodrugs and for providing combination therapies including the prodrugs. The advantages for using prodrugs of the invention include the facilitation of controlled formulation into an LNP of the disclosure (e.g., a liposome). This allows the prodrug to be maintained in an inactive form during systemic circulation, which allows the liposome to release the active agent after engulfment by a cell, for example within a tumor.

In certain embodiments one or more PD-1 Prodrugs (e.g., any one or more of the PD-1 Prodrugs inhibitors taught in Formula I, Formula 2, and/or PD1-PD7) (See, section entitled prodrugs) are formulated a lipid moiety that forms a vesicle (e.g., a liposome) structure in aqueous solution or that can form a component of a lipid bilayer comprising a liposome. The liposomes can be used directly, provided as components in a combined formulation (e.g., in combination with another drug moiety or therapeutic modality as disclosed herein).

In certain embodiments, the liposome that is formulated with the PD-1 Prodrug comprises a lipid, PHGP, vitamin E, cholesterol, and/or a fatty acid.

In one embodiment, the liposome comprises cholesterol.
In one embodiment, the liposome comprises DPPG.
In one embodiment, the liposome comprises DMPG.
In one embodiment, the liposome Lyso PC.
In one embodiment, the liposome (Δ9-Cis) PG.
In one embodiment, the liposome comprises Soy Lyso PC.
In one embodiment, the liposome comprises PG.
In one embodiment, the liposome comprises PA-PEG3-mannose.
In one embodiment, the liposome comprises C16 PEG2000 Ceramide.
In one embodiment, the liposome comprises MPLA.
In one embodiment, the liposome comprises CHEMS.
In one embodiment, the liposome comprises Stearic Acid.
In one embodiment, the liposome comprises a phospholipid set forth in Table III.
In one embodiment, the liposome comprises any one of PD1-PD7 and further comprises a DPPG and further comprises a LU wherein said LU is an ester.
In one embodiment, the liposome comprises any one of PD1-PD7 and further comprises cholesterol and further comprises a LU wherein said LU is an ester.
In one embodiment, the liposome comprises any one of PD1-PD7 and further comprises a DPPG and further comprises a LU wherein said LU is an ester and further comprises a helper lipid set forth in Table II.
In one embodiment, the liposome comprises any one of PD1-PD7 and further comprises a cholesterol and further comprises a LU wherein said LU is an ester and further comprises a helper lipid set forth in Table II.
In one embodiment, the liposome comprises PD3 and further comprises a DPPG and further comprises a LU wherein said LU is an ester and further comprises a helper lipid set forth in Table II.
In one embodiment, the liposome comprises PD3 and further comprises a cholesterol and further comprises a LU wherein said LU is an ester and further comprises a helper lipid set forth in Table II.
In one embodiment, the liposome comprises PD6 and further comprises a DPPG and further comprises a LU wherein said LU is an ester and further comprises a helper lipid set forth in Table II.
In one embodiment, the liposome comprises PD6 and further comprises a cholesterol and further comprises a LU wherein said LU is an ester and further comprises a helper lipid set forth in Table II.
In one embodiment, the liposome of the disclosure comprises a PD-1 Prodrug co-formulated with one or more additional immune modulating agents, whereby the immune modulating agents includes, but is not limited to, immunogenic-cell death inducing chemotherapeutics, toll receptor agonists, sting agonists, CTLA4 inhibitors, and/or prodrugs thereof.

In a preferred embodiment, the liposome comprises a PD-1 Prodrug co-formulated with an ICD-inducing Chemotherapeutic.

In a preferred embodiment, the liposome comprises a PD-1 Prodrug co-formulated with an ICD-inducing Chemotherapeutic selected from the list: doxorubicin (DOX), mitoxantrone (WO), Oxaliplatin (OXA), Cyclophosphamide (CP), Bortezomib, Carfilzimib, or Paclitaxel.

In a preferred embodiment, the liposome comprises a PD-1 Prodrug co-formulated with a Toll Receptor TLR agonist/Prodrug.

In a further preferred embodiment, the Toll Receptor TLR agonist/Prodrug is selected from the group consisting of TR3, TR4, TR5, and TR6.

In a preferred embodiment, the liposome comprises a PD-1 Prodrug co-formulated with Toll Receptor (TLR) agonist/Prodrug selected from the list: Resiquimod (R848), Gardiquimod, 852A, DSR 6434, Telratolimod, CU-T12-9, monophosphoryl Lipid A (MPLA), 3D(6-acyl)-PHAD®, or 3D-PHAD®.

In a preferred embodiment, the liposome comprises a PD-1 Prodrug co-formulated with an ID0-1 inhibitor/Prodrug.

In a preferred embodiment, the liposome comprises a PD-1 Prodrug co-formulated with an IDO-1 inhibitor/Prodrug, selected from the list: D-1-Methyl Tryptophan (D-1-MT), L-1-Methyl Tryptophan (L-1-MT), Epacadostat, Linrodostat, or Navoximod.

In a preferred embodiment, the liposome comprises a PD-1 Prodrug co-formulated with doxorubicin (DOX).

In a preferred embodiment, the liposome comprises a PD-1 Prodrug co-formulated with mitoxantrone (MTO).

In a preferred embodiment, the liposome comprises a PD-1 Prodrug co-formulated with doxorubicin (DOX) and an IDO prodrug.

In a preferred embodiment, the liposome comprises a PD-1 Prodrug co-formulated with mitoxantrone (MTO) and an IDO prodrug.

In a preferred embodiment, the liposome comprises a PD-1 Prodrug co-formulated with doxorubicin (DOX) and a TLR agonist/prodrug.

In a preferred embodiment, the liposome comprises a PD-1 Prodrug co-formulated with mitoxantrone (MTO) and a TLR agonist/prodrug.

In a preferred embodiment, the liposome comprises a PD-1 Prodrug co-formulated with doxorubicin (DOX) and an IDO prodrug and a TLR agonist/prodrug.

In a preferred embodiment, the liposome comprises a PD-1 prodrug co-formulated with mitoxantrone (MTO) and an IDO prodrug and a TLR agonist/prodrug.

In a preferred embodiment, the liposome comprises a PD-1 Prodrug co-formulated with a TGFβ antagonist/prodrug.

In a preferred embodiment, the liposome comprises a PD-1 Prodrug co-formulated with a A2aR antagonist/prodrug.

In a further preferred embodiment, the A2aR antagonist/Prodrug further comprises AR5.

In a preferred embodiment, the liposome comprises a PD-1 Prodrug co-formulated with a TLR agonist/prodrug and an IDO prodrug.

In a preferred embodiment, the liposome comprises PD3 co-formulated with doxorubicin (DOX).

In a preferred embodiment, the liposome comprises PD3 co-formulated with mitoxantrone (MTO).

In a preferred embodiment, the liposome comprises PD6 co-formulated with doxorubicin (DOX).

In a preferred embodiment, the liposome comprises PD6 co-formulated with mitoxantrone (MTO).

In a preferred embodiment, the liposome comprises PD3 co-formulated with doxorubicin (DOX) and/or and IDO prodrug and/or a TLR agonist/prodrug.

In a preferred embodiment, the liposome comprises PD3 co-formulated with mitoxantrone (MTO) and/or and IDO prodrug and/or a TLR agonist/prodrug.

In a preferred embodiment, the liposome comprises PD6 co-formulated with doxorubicin (DOX) and/or and IDO prodrug and/or a TLR agonist/prodrug.

In a preferred embodiment, the liposome comprises PD6 co-formulated with mitoxantrone (MTO) and/or and IDO prodrug and/or a TLR agonist/prodrug.

In another preferred embodiment, the liposome comprises a solid-lipid nanoparticle (SLNP) comprising a liposome which comprises a PD-1 Prodrug.

One of skill in the art will appreciate and understand that solubility is one of most common problems faced by the artisan in the drug development process. Chemical conjugation of a drug/anti-cancer agents via lipid molecules (i.e., lipid-based prodrugs) provides a platform to solve the problem of formulating the drugs in an aqueous suspension. The major advantages of delivering drug(s) with lipid conjugation (lipid-based prodrugs) lies on its ability to improve pharmacokinetics/half-life and targeted delivery.

With suitable selection of lipid molecules, lipid-based prodrug(s) can be integrated/formulated in a liposomal formulation using techniques known in the art, which has many more advantages over conventional drug delivery system. (KOHLI, et. al., J. Control Release, 0: pp 274-287 (Sep. 28, 2014); and GARCIA-PINEL, et. al., Nanomaterials 9:638 (2019). The advantage of combining lipid-prodrug with liposomes is twofold: (i) liposomes containing lipid-prodrug not only increase the solubility of the drug/prodrug itself, but (ii) also have the ability to encapsulate multiple drugs (both hydrophilic and lipophilic) (see, section entitled nanocarriers).

For the purposes of this disclosure, the major advantage of liposome formulations are as follows:
  i) biocompatibility/biodegradability and no general toxicity of the liposome's formulations;
  ii) flexibility and manipulation of size and surface charge depending on the required purpose. Liposome formulation(s), for the purposes of this disclosure, can have a size range of 40-150 nm in diameter and a surface charge in the range of −40 to +40 mV; and
  iii) Liposomes of the invention have either a single or multiple lipid-prodrugs as the constituent lipid portion of the liposome(s). Additionally, multiple drugs (e.g., that work in different mechanism of action) and with different solubility profile (hydrophilic or lipophilic) can be formulated (either in the lipid bilayers or in the hydrophilic core) in these liposomes.

As one of ordinary skill in the art will appreciate, all methods of making liposomes involve four (4) basic stages:
  (i) Drying down lipids from organic solvent;
  (ii) Dispersing the lipid in aqueous solution;
  (iii) Purifying the resultant liposome; and
  (iv) Analyzing the final product.

See, AKBARZADEH, et. al., Nanoscale Research Letters, 8:102 (2013).

Another aspect of the invention discloses liposomal encapsulation technology (LET) which is a delivery technique used to transmit drugs. LET is a method of generating sub-microscopic foams called liposomes, which encapsulate numerous materials. These 'liposomes' form a barrier around their contents, which is resistant to enzymes in the mouth and stomach, alkaline solutions, digestive juices, bile salts, and intestinal flora that are generated in the human body, as well as free radicals. The contents of the liposomes are, therefore, protected from oxidation and degradation. This protective phospholipid shield or barrier remains undamaged until the contents of the liposome are delivered to the exact target gland, organ, or system where the contents will be utilized (See, section entitled nanocarriers).

In one embodiment, liposome(s) of the disclosure are synthesized using a plurality of different ratios of PD-1 Prodrugs, lipids, and/or lipid-prodrugs. As disclosed herein, the PD-1 Prodrugs may comprise helper lipids as disclosed herein (See, for example Table II).

In one embodiment, liposome(s) of the disclosure are synthesized using a plurality of different ratios of PD-1 Prodrugs, lipids, and/or lipid-prodrugs. As disclosed herein, the PD-1 Prodrugs may further comprise DSPE-PEGs.

In a preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Lipid 2 (lipid-prodrug) | 0-60 |
| Helper lipids | 0-50 |
| DSPEG-PEG 2000 | 2-5 |

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 0-50 |
| DSPEG-PEG 2000 | 2-5 |

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 0-50 |
| DSPEG-PEG 2000 | 2-5 |

Whereby Lipid 1 comprises PD3 and cholesterol.

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 0-50 |
| DSPEG-PEG 2000 | 2-5 |

Whereby Lipid 1 comprises PD6 and cholesterol.

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 0-50 |
| DSPEG-PEG 2000 | 2-5 |

Whereby Lipid 1 comprises PD3 and DPPG.

In a further preferred embodiment, the liposomes of the invention comprise a composition having the following ratio(s):

| Constituent of the Liposome | Amount (% w/w) |
|---|---|
| Lipid 1 (lipid-prodrug) | 5-60 |
| Helper lipids | 0-50 |
| DSPEG-PEG 2000 | 2-5 |

Whereby Lipid 1 comprises PD6 and DPPG.

One of ordinary skill in the art will appreciate and be enabled to make variations and modifications to the disclosed embodiment without altering the function and purpose of the invention disclosed herein. Such variations and modifications are intended within the scope of the present disclosure.

VIII.) Pharmaceutical Formulation

As used herein, the term "drug" is synonymous with "pharmaceutical". In certain embodiments, the liposome of the disclosure is fabricated to an encapsulated dosage form to and given to a patient for the treatment of disease.

Generally speaking, pharmaceutical formulation is the process in which different chemical substances are combined to a pure drug substance to produce a final drug product. Formulation studies involve developing a preparation of the drug which is both stable and acceptable to the patient. For orally taken drugs, this usually involves incorporating the drug into a tablet or a capsule. It is important to appreciate that a dosage form contains a variety of other substances apart from the drug itself, and studies have to be carried out to ensure that the drug is compatible with these other substances.

An excipient is an inactive substance used as a carrier for the active ingredients of a drug product, in this case a liposome comprising a PD-1 Prodrug. In addition, excipients can be used to aid the process by which a drug product is manufactured. The active substance is then dissolved or mixed with an excipient. Excipients are also sometimes used to bulk up formulations with very potent active ingredients, to allow for convenient and accurate dosage. Once the active ingredient has been purified, it cannot stay in purified form for very long. In many cases it will denature, fall out of solution, or stick to the sides of the container.

To stabilize the active ingredient, excipients are added to ensure that the active ingredient stays active and is stable for a long enough period of time that the shelf-life of the product makes it competitive with other products and safe for the end-user. Examples of excipients include but are not limited to, anti-adherents, binders, coatings, disintegrants, fillers, diluents, flavors, colors, lubricants, and preservatives. The final formulation comprises and active ingredient and excipients which are then enclosed in the pharmaceutical dosage form.

Pre-formulation involves the characterization of a drug's physical, chemical, and mechanical properties in order to choose what other ingredients should be used in the preparation. Formulation studies then consider such factors as stability, particle size, polymorphism, pH, and solubility, as all of these can influence bioavailability and hence the activity of a drug. The drug must be combined with inactive additives by a method which ensures that the quantity of drug present is consistent in each dosage unit (e.g., each vial). The dosage should have a uniform appearance.

It is unlikely that these studies will be complete by the time clinical trials commence. This means that simple preparations are developed initially for use in phase I clinical trials. These typically consist of vials, hand-filled capsules containing a small amount of the drug and a diluent. Proof of the long-term stability of these formulations is not required, as they will be used (tested) in a matter of days. However, long-term stability is critical in supply chain management since the time the final formulation is packaged until it reaches the patient can be several months or years. Consideration has to be given to what is called the drug load (i.e., the ratio of the active drug to the total contents of the dose). A low drug load may cause homogeneity problems. A high drug load may pose flow problems or require large capsules if the compound has a low bulk density. By the time phase III clinical trials are reached, the formulation of the drug should have been developed to be close to the preparation that will ultimately be used in the market.

A knowledge of stability is essential by this stage, and conditions must have been developed to ensure that the drug is stable in the preparation. If the drug proves unstable, it will invalidate the results from clinical trials since it would be impossible to know what the administered dose actually was. Stability studies are carried out to test whether temperature, humidity, oxidation, or photolysis (ultraviolet light or visible light) have any effect, and the preparation is analyzed to see if any degradation products have been formed. It is also important to check whether there are any unwanted interactions between the preparation and the container. If a plastic container is used, tests are carried out to see whether any of the ingredients become adsorbed on to the plastic, and whether any plasticizers, lubricants, pigments, or stabilizers leach out of the plastic into the preparation. Even the adhesives for the container label need to be tested, to ensure they do not leach through the plastic container into the preparation. The way a drug is formulated can avoid some of the problems associated with oral administration. Drugs are normally taken orally as tablets or capsules. The drug (active substance) itself needs to be soluble in aqueous solution at a controlled rate. Such factors as particle size and crystal form can significantly affect dissolution. Fast dissolution is not always ideal. For example, slow dissolution rates can prolong the duration of action or avoid initial high plasma levels.

In some embodiments, the nanocarrier (e.g., a liposome comprising a PD-1 Prodrug) and/or the liposome comprising a PD-1 Prodrug and co-formulated with an immune modulating agent or other combination(s) as disclosed herein are administered alone or in a mixture with a physiologically acceptable carrier (such as physiological saline or phosphate buffer) selected in accordance with the route of administration and standard pharmaceutical practice. For example, when used as an injectable, the nanocarriers can be formulated as a sterile suspension, dispersion, or emulsion with a pharmaceutically acceptable carrier. In certain embodiments normal saline can be employed as the pharmaceutically acceptable carrier. Other suitable carriers include, e.g., water, buffered water, 0.4% saline, 0.3% glycine, 5% glucose and the like, including glycoproteins for enhanced stability, such as albumin, lipoprotein, globulin, etc. In compositions comprising saline or other salt-containing carriers, the carrier is preferably added following nanocarrier formation. Thus, after the nanocarrier is formed and loaded with suitable drug(s), the nanocarrier can be diluted into pharmaceutically acceptable carriers such as normal saline. Similarly, the PD-1 Prodrug liposomes can be introduced into carriers that facilitate suspension of the nanomaterials (e.g., emulsions, dilutions, etc.).

The pharmaceutical compositions may be sterilized by conventional, well-known sterilization techniques. The resulting aqueous solutions, suspensions, dispersions, emulsions, etc., may be packaged for use or filtered under aseptic conditions. In certain embodiments the drug delivery nanocarriers (e.g., LB-coated nanoparticles) are lyophilized, the lyophilized preparation being combined with a sterile aqueous solution prior to administration. The compositions may also contain pharmaceutically acceptable auxiliary substances as required to approximate physiological conditions, such as pH-adjusting and buffering agents, tonicity adjusting agents and the like, for example, sodium acetate, sodium lactate, sodium chloride, potassium chloride, calcium chloride, etc.

Additionally, in certain embodiments, the pharmaceutical formulation may include lipid-protective agents that protect lipids against free-radical and lipid-peroxidative damage on storage. Lipophilic free-radical quenchers, such as alpha-tocopherol and water-soluble iron-specific chelators, such as ferrioxamine, are suitable and contemplated herein. The concentration of nanocarrier (e.g., liposome comprising PD-1 Prodrugs) in the pharmaceutical formulations can vary widely, e.g., from less than approximately 0.05%, usually at least approximately 2 to 5% to as much as 10 to 50%, or to 40%, or to 30% by weight and are selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, nanocarriers composed of irritating lipids may be diluted to low concentrations to lessen inflammation at the site of administration. The amount of nanocarriers administered will depend upon the particular drug used, the disease state being treated and the judgment of the clinician but will generally be between approximately 0.01 and approximately 50 mg per kilogram of body weight, preferably between approximately 0.1 and approximately 5 mg per kg of body weight.

One of skill in the art will appreciate that exact dosages will vary depending upon such factors as the particular PD-1 Prodrugs and any co-formulated immune modulating agents and the desirable medical effect, as well as patient factors such as age, sex, general condition, and the like. Those of skill in the art can readily take these factors into account and use them to establish effective therapeutic concentrations without resort to undue experimentation.

For administration to humans (or to non-human mammals) in the curative, remissive, retardive, or prophylactic treatment of diseases described herein the prescribing physician will ultimately determine the appropriate dosage of the drug for a given human (or non-human) subject, and this can be expected to vary according to the age, weight, and response of the individual as well as the nature and severity of the patient's disease. In certain embodiments the dosage of the drug provided by the nanocarrier(s) can be approximately equal to that employed for the free drug. However as noted above, the nanocarriers described herein can significantly reduce the toxicity of the drug(s) administered thereby and significantly increase a therapeutic window. Accordingly, in some cases dosages in excess of those prescribed for the free drug(s) will be utilized.

One of ordinary skill in the art will appreciate and be enabled to make variations and modifications to the disclosed embodiment without altering the function and purpose of the invention disclosed herein. Such variations and modifications are intended within the scope of the present disclosure.

IX.) Combination Therapy

As the skilled artisan will appreciate and understand, cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

Thus, the liposomes or SLNPs comprising PD-1 Prodrugs of the present disclosure can be used in combination with one or more other enzyme/protein/receptor inhibitors or one or more therapies for the treatment of diseases, such as cancer or infections. Examples of diseases and indications treatable with combination therapies include those set forth in the present disclosure. Examples of cancers include, but are not limited to, solid tumors and liquid tumors, such as blood cancers. Examples of infections include viral infections, bacterial infections, fungus infections or parasite infections.

For example, the liposomes or SLNPs comprising PD-1 Prodrugs of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, PI3K (alpha, beta, gamma, delta), CSFIR, KIT, FLK-II, KDR/FLK-1, FLK-4, flt-1, FGFR1, FGFR2, FGFR3, FGFR4, c-Met, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In further embodiments, the liposomes or SLNPs comprising PD-1 Prodrugs of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, or BMS-986205), an LSD1 inhibitor (e.g., INCB59872 and INCB60003), a TDO inhibitor, a PI3K-delta inhibitor (e.g., INCB50797 and INCB50465), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), a poly ADP ribose polymerase (PARP) inhibitor such as rucaparib, olaparib, niraparib, veliparib, or talazoparib, an arginase inhibitor (INCB01158), TGFβ inhibitor, a CTLA-4 antagonists, a A2aR inhibitor, and an adenosine receptor antagonist or combinations thereof.

Additionally, the liposomes or SLNPs comprising PD-1 Prodrugs of the present disclosure can further be used in combination with other methods of treating cancers, for example by chemotherapy, irradiation therapy, tumor-targeted therapy, adjuvant therapy, immunotherapy, or surgery.

Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like.

The liposomes or SLNPs comprising PD-1 Prodrugs can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Other anti-cancer agent(s) include antibody therapeutics such as trastuzumab (Herceptin), antibodies to costimulatory molecules such as CTLA-4 (e.g., ipilimumab), 4-1BB (e.g., urelumab, utomilumab), antibodies to PD-1 and PD-L1/L2, or antibodies to cytokines (IL-10, TGF-.beta., etc.).

Examples of antibodies to PD-1 and/or PD-L1/L2 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

In addition, liposomes or SLNPs comprising PD-1 Prodrugs of the present disclosure can be used in combination with one or more immune checkpoint inhibitors for the treatment of diseases, such as cancer or infections. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2.

In some embodiments, the immune checkpoint molecule is a stimulatory checkpoint molecule selected from CD27, CD28, CD40, ICOS, OX40, GITR and CD137. In further embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In further embodiments, the liposomes or SLNPs comprising PD-1 Prodrugs provided herein can be used in combination with one or more agents selected from KIR inhibitors, TIGIT inhibitors, LAIR1 inhibitors, CD160 inhibitors, 2B4 inhibitors and TGFR beta inhibitors.

X.) Methods of Delivering Liposomes Nanocarriers PD-1 Prodrugs to a Cell Expressing PD-1-L/L2

As it is known in the art, a wide variety of compositions and methods for using prodrugs and/or nanocarriers to kill tumor cells are known in the art. In the context of cancers, typical methods entail administering to a mammal having a tumor, a biologically effective amount of a PD-1 Prodrug of the disclosure, and/or a nanocarrier of the disclosure comprising a PD-1 Prodrug.

A typical embodiment is a method of delivering a therapeutic agent to a cell expressing PD-1-L1/L2, comprising forming a PD-1 Prodrug by conjugating a drug moiety of the disclosure with a lipid of the disclosure via a Linkage Unit, and exposing the cell to the PD-1 Prodrug.

In one embodiment, the PD-1 Prodrug comprises a drug moiety of Formula I and a cholesterol conjugated via a LU comprising an ester.

In one embodiment, the PD-1 Prodrug comprises a drug moiety of Formula II and a cholesterol conjugated via a LU comprising an ester.

In one embodiment, the PD-1 Prodrug comprises a drug moiety of Formula I and DPPG conjugated via a LU comprising an ester.

In one embodiment, the PD-1 Prodrug comprises a drug moiety of Formula II and DPPG conjugated via a LU comprising an ester.

In one embodiment, the PD-1 prodrug comprises PD1, and a cholesterol conjugated via a LU comprising an ester.

In one embodiment, the PD-1 prodrug comprises PD2, and a cholesterol conjugated via a LU comprising an ester.

In one embodiment, the PD-1 prodrug comprises PD3, and a cholesterol conjugated via a LU comprising an ester.

In one embodiment, the PD-1 prodrug comprises PD4, and a cholesterol conjugated via a LU comprising an ester.

In one embodiment, the PD-1 prodrug comprises PD5, and a cholesterol conjugated via a LU comprising an ester.

In one embodiment, the PD-1 prodrug comprises PD6, and a cholesterol conjugated via a LU comprising an ester.

In one embodiment, the PD-1 prodrug comprises PD7, and a cholesterol conjugated via a LU comprising an ester.

In one embodiment, the PD-1 prodrug comprises PD1 and DPPG conjugated via a LU comprising an ester.

In one embodiment, the PD-1 prodrug comprises PD2 and DPPG conjugated via a LU comprising an ester.

In one embodiment, the PD-1 prodrug comprises PD3 and DPPG conjugated via a LU comprising an ester.

In one embodiment, the PD-1 prodrug comprises PD4 and DPPG conjugated via a LU comprising an ester.

In one embodiment, the PD-1 prodrug comprises PD5 and DPPG conjugated via a LU comprising an ester.

In one embodiment, the PD-1 prodrug comprises PD6 and DPPG conjugated via a LU comprising an ester.

In one embodiment, the PD-1 prodrug comprises PD7 and DPPG conjugated via a LU comprising an ester.

Another illustrative embodiment is a method of treating an individual suspected of suffering from metastasized cancer, comprising a step of administering parenterally to said individual a pharmaceutical composition comprising a therapeutically effective amount of a PD-1 Prodrug produced by conjugating a drug moiety with a lipid of the disclosure via a Linkage Unit, and exposing the cell to the PD-1 Prodrug.

In one embodiment, the PD-1 prodrug comprises a drug moiety of Formula I and a cholesterol conjugated via a LU comprising an ester.

In one embodiment, the PD-1 Prodrug comprises a drug moiety of Formula II and a cholesterol conjugated via a LU comprising an ester.

In one embodiment, the PD-1 Prodrug comprises a drug moiety of Formula I and DPPG conjugated via a LU comprising an ester.

In one embodiment, the PD-1 Prodrug comprises a drug moiety of Formula II and DPPG conjugated via a LU comprising an ester.

In one embodiment, the PD-1 prodrug comprises PD1, and a cholesterol conjugated via a LU comprising an ester.

In one embodiment, the PD-1 prodrug comprises PD2, and a cholesterol conjugated via a LU comprising an ester.

In one embodiment, the PD-1 prodrug comprises PD3, and a cholesterol conjugated via a LU comprising an ester.

In one embodiment, the PD1 prodrug comprises PD4, and a cholesterol conjugated via a LU comprising an ester.

In one embodiment, the PD1 prodrug comprises PD5, and a cholesterol conjugated via a LU comprising an ester.

In one embodiment, the PD1 prodrug comprises PD6, and a cholesterol conjugated via a LU comprising an ester.

In one embodiment, the PD1 prodrug comprises PD7, and a cholesterol conjugated via a LU comprising an ester.

In one embodiment, the PD1 prodrug comprises PD1 and DPPG conjugated via a LU comprising an ester.

In one embodiment, the PD1 prodrug comprises PD2 and DPPG conjugated via a LU comprising an ester.

In one embodiment, the PD1 prodrug comprises PD3 and DPPG conjugated via a LU comprising an ester.

In one embodiment, the PD1 prodrug comprises PD4 and DPPG conjugated via a LU comprising an ester.

In one embodiment, the PD1 prodrug comprises PD5 and DPPG conjugated via a LU comprising an ester.

In one embodiment, the PD1 prodrug comprises PD6 and DPPG conjugated via a LU comprising an ester.

In one embodiment, the PD1 prodrug comprises PD7 and DPPG conjugated via a LU comprising an ester.

PD-1 Prodrugs, SLNPs, liposomes, and co-formulated liposomes and/or SLNPs of the present disclosure inhibit the activity of PD-1-L1/L2 protein/protein interaction and, thus, are useful in treating diseases and disorders associated with activity of PD-1 and the diseases and disorders associated with PD-L1 and/or PD-L2 including its interaction with other proteins such as PD-1 and B7-1 (CD80). In further embodiments of the disclosure, the PD-1 Prodrugs, SLNPs, liposomes, nanocarriers, or pharmaceutically acceptable salts or stereoisomers thereof, are useful for therapeutic administration to enhance, stimulate and/or increase immunity in cancer, chronic infection, or sepsis, including enhancement of response to vaccination.

In further embodiments, the present disclosure provides a method for inhibiting the PD-1-L1/L2 protein/protein interaction. The method includes administering to an individual or a patient a PD-1 Prodrug, liposomes, SLNPs, and/or of any of the formulas (Formula I or Formula II) as described herein (e.g., PD1-PD7), or of a PD-1 Prodrug, liposomes, SLNP, and nano-encapsulated PD-1 inhibitor prodrugs as recited in any of the claims and described herein, or a pharmaceutically acceptable salt or a stereoisomer thereof. The PD-1 Prodrug, liposomes, SLNP, and nano-encapsulated PD-1 inhibitor prodrugs of the present disclosure can be used alone, in combination with other agents or therapies or as an adjuvant or neoadjuvant for the treatment of diseases or disorders, including cancer and other diseases. For the uses and methods described herein, any of the PD-1 Prodrugs, liposomes, SLNP, and nano-encapsulated PD-1 Prodrugs of the disclosure, including any of the embodiments thereof, may be used.

In addition, The PD-1 Prodrugs, liposomes, SLNP, and nano-encapsulated PD-1 inhibitor prodrugs of the present disclosure inhibit the PD-1/L1/L2 protein/protein interaction, resulting in a PD-1 pathway blockade. As is known in the art, the blockade of PD-1 can enhances the immune response to cancerous cells and infectious diseases in mammals, including humans.

In further embodiments, the present disclosure provides treatment of an individual or a patient in vivo using PD-1 Prodrugs, liposomes, SLNPs, and nano-encapsulated PD-1 inhibitor prodrug or a salt or stereoisomer thereof such that growth of cancerous tumors is inhibited.

PD-1 Prodrugs, liposomes, SLNPs, and nano-encapsulated PD-1 inhibitor prodrugs, or of any of the formulas (Formula I or Formula II) as described herein (e.g., PD1-PD7), or PD-1 prodrugs, liposomes, SLNPs, and nano-encapsulated PD-1 inhibitor prodrugs as recited in any of the claims and described herein, or a salt or stereoisomer thereof, can be used to inhibit the growth of cancerous tumors.

In the alternative, PD-1 Prodrugs, liposomes, SLNPs, and nano-encapsulated PD-1 Prodrugs of the disclosure, or of any of the formulas (Formula I or Formula II) as described herein, or a compound as recited in any of the claims and described herein (e.g., PD1-PD7), or a salt or stereoisomer thereof, can be used in conjunction with other agents or standard cancer treatments, as described in this disclosure.

In a further embodiment, the present disclosure provides a method for inhibiting growth of tumor cells in vitro. The method includes contacting the tumor cells in vitro with PD-1 Prodrugs, liposomes, SLNPs, and nano-encapsulated PD-1 inhibitor prodrugs of the disclosure, or of any of the formulas (Formula I or Formula II) as described herein (e.g., PD1-PD7), or of a PD-1 Prodrug, SLNPs, liposomes, and nano-encapsulated PD-1 inhibitor prodrugs as recited in any of the claims and described herein, or of a salt or stereoisomer thereof.

In a further embodiment, the present disclosure provides a method for inhibiting growth of tumor cells in a patient. The method includes contacting the tumor cells with PD-1 Prodrugs, liposomes, SLNPs, and nano-encapsulated PD-1 inhibitor prodrugs of the disclosure, or of any of the formulas (Formula I or Formula II) as described herein (e.g., PD1-PD7), or of a PD-1 prodrug, liposomes, SLNPs, and nano-encapsulated PD-1 inhibitor prodrugs as recited in any of the claims and described herein, or of a salt or stereoisomer thereof.

XI.) Methods of Treating Cancer(s) and Other Immunological Disorder(s)

Another embodiment of the present disclosure is a method for treating cancer. The method comprises administering to a patient, a therapeutically effective amount of a liposome comprising a PD-1 Prodrug (i.e., PD1-PD7) herein, a compound as recited in any of the claims and described herein, or a salt thereof. Examples of cancers include those whose growth may be inhibited using PD-1 inhibitors of the disclosure and PD-1 Prodrugs of the disclosure and cancers typically responsive to immunotherapy.

In some embodiments, the present disclosure provides a method of enhancing, stimulating and/or increasing the immune response in a patient. The method includes administering to the patient a therapeutically effective amount of a PD-1 Prodrug and/or a liposome or SLNP comprising the same (i.e., PD1-PD7), a compound or composition as recited in any of the claims and described herein, or a salt thereof.

Non-limiting examples of cancers that are treatable using the liposomes comprising PD-1 Prodrugs, liposomes, SLNPs, and/or co-formulated liposomes or SLNPs of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers, especially metastatic cancers that express PD-1-L1/L2.

In some embodiments, cancers treatable with liposomes, SLNPs, or PD-1 Prodrugs of the present disclosure include melanoma (e.g., metastatic malignant melanoma), renal cancer (e.g. clear cell carcinoma), prostate cancer (e.g. hormone refractory prostate adenocarcinoma), breast cancer, colon cancer, lung cancer (e.g. non-small cell lung cancer and small cell lung cancer), squamous cell head and neck cancer, urothelial cancer (e.g. bladder) and cancers with high microsatellite instability (MSI$^{high}$). Additionally, the disclosure includes refractory or recurrent malignancies whose growth may be inhibited using the liposomes, SLNPs, or PD-1 Prodrugs or co-formulated liposomes or SLNPs of the disclosure.

In additional embodiments, cancers that are treatable using the formulated and/or co-formulated liposomes or SLNPs or PD-1 Prodrugs of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In further embodiments, cancers that are treatable using the formulated and/or co-formulated liposomes or SLNPs or PD-1 Prodrugs of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal carcinoma, salivary gland cancer, sinus cancer, spinal cancer, tongue cancer, tubular carcinoma, urethral cancer, and ureteral cancer.

In addition, in some embodiments, the formulated and/or co-formulated liposomes, SLNPs, or PD-1 Prodrugs of the present disclosure can be used to treat sickle cell disease and sickle cell anemia.

Furthermore, in some embodiments, diseases and indications that are treatable using the formulated and/or co-formulated liposomes, SLNPs, or PD-1 Prodrugs of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors.

Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Additionally, PD-1 pathway blockade with formulated and/or co-formulated liposomes, SLNPs, or PD-1 Prodrugs of the present disclosure can also be used for treating infections such as viral, bacteria, fungus, and parasite infections.

The present disclosure provides a method for treating infections such as viral infections. The method includes administering to a patient, a therapeutically effective amount of a formulated and/or co-formulated liposomes, SLNPs, or PD-1 Prodrugs or any of the formulas (Formula I or Formula II) as described herein (i.e., PD-1-PD7) as recited in any of the claims and described herein, a salt thereof.

Examples of viruses causing infections treatable by methods of the present disclosure include, but are not limited to, human immunodeficiency virus, human papillomavirus, influenza, hepatitis A, B, C or D viruses, adenovirus, poxvirus, herpes simplex viruses, human cytomegalovirus, severe acute respiratory syndrome virus, Ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

In addition, the present disclosure provides a method for treating bacterial infections. The method includes administering to a patient, a therapeutically effective amount of a formulated and/or co-formulated liposomes, SLNPs, or PD-1 Prodrugs, or any of the formulas (Formula I or Formula II) as described herein (i.e., PD-1-PD7) as recited in any of the claims and described herein, or a salt thereof.

Examples of pathogenic bacteria causing infections treatable by methods of the disclosure, include but are not limited to, chlamydia, rickettsia bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

In addition, the present disclosure provides a method for treating fungus infections. The method includes administering to a patient, a therapeutically effective amount of a formulated and/or co-formulated liposomes, SLNPS, or PD-1 Prodrugs, or any of the formulas (Formula I or Formula II) as described herein (i.e., PD-1-PD7) as recited in any of the claims and described herein, or a salt thereof.

Examples of pathogenic fungi causing infections treatable by methods of the disclosure, include, but are not limited to, *Candida* (*albicans, krusei, glabrata, tropicalis*, etc.), *Cryptococcus neoformans, Aspergillus* (*fumigatus, Niger*, etc.), Genus *Mucorales* (*Mucor, absidia, rhizophus*), *Sporothrix schenkii, Blastomyces dermatitidis, Paracoccidioides brasiliensis, Coccidioides immitis* and *Histoplasma capsulatum*.

Additionally, the present disclosure provides a method for treating parasite infections. The method includes administering to a patient, a therapeutically effective amount of a formulated and/or co-formulated liposomes or SLNPs or PD-1 Prodrugs, or any of the formulas (Formula I or Formula II) as described herein (i.e., PD-1-PD7) as recited in any of the claims and described herein, or a salt thereof.

Examples of pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

In a further set of embodiments that are within the scope of this disclosure, the formulated and/or co-formulated liposomes, SLNPs, or PD-1 Prodrugs, or any of the formulas (Formula I or Formula II) as described herein (i.e., PD-1-PD7) are useful in preventing or reducing the risk of developing any of the diseases referred to in this disclosure; e.g., preventing or reducing the risk of developing a disease, condition or disorder in an individual who may be predisposed to the disease, condition or disorder but does not yet experience or display the pathology or symptomatology of the disease.

In one embodiment, the methods described herein comprise LNP-PD3 and/or a therapeutically effective amount of LNP-PD3.

In one embodiment, the methods described herein comprise SLNP-PD3 and/or a therapeutically effective amount of SLNP-PD3.

In one embodiment, the methods described herein comprise SLNP-PD3-TR5 and/or a therapeutically effective amount of SLNP-PD3-TR5.

In one embodiment, the methods described herein comprise SLNP-PD3-AR5 and/or a therapeutically effective amount of SLNP-PD3-AR5.

In one embodiment, the methods described herein comprise SLNP-PD3-AR5-DOX and/or a therapeutically effective amount of SLNP-PD3-AR5-DOX.

XII.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a formulated and/or co-formulated liposome or SLNP that is or can be detectably labeled and/or is loaded with a PD-1 Prodrug of the disclosure. Kits can comprise a container comprising a drug unit. The kit can include all or part of the formulated and/or co-formulated liposomes, SLNPs, and/or PD-1 Prodrug.

The kit of the invention will typically comprise the container described above, and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer or other immunological disorder.

The terms "kit" and "article of manufacture" can be used as synonyms.

In another embodiment of the invention, an article(s) of manufacture containing compositions, such as formulated and/or co-formulated liposomes, SLNPs, and/or PD-1 Prodrugs are within the scope of this disclosure. The article of manufacture typically comprises at least one container and at least one label. Suitable containers include, for example, bottles, vials, syringes, and test tubes. The containers can be formed from a variety of materials such as glass, metal, or plastic. The container can hold formulated and/or co-formulated liposomes or SLNPs loaded with PD-1 Prodrugs.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be formulated and/or co-formulated liposomes or SLNPs loaded with a single PD-1 Prodrug and/or a combination of PD-1 Prodrugs as disclosed herein.

The article of manufacture can further comprise a second container comprising a pharmaceutically acceptable buffer, such as phosphate-buffered saline, Ringers solution and/or dextrose solution. It can further include other materials desirable from a commercial and user standpoint, including other buffers, diluents, filters, stirrers, needles, syringes, and/or package inserts with indications and/or instructions for use.

In one embodiment, the kit or article of manufacture comprises LNP-PD3 and/or a therapeutically effective amount of LNP-PD3.

In one embodiment, the kit or article of manufacture comprises SLNP-PD3 and/or a therapeutically effective amount of SLNP-PD3.

In one embodiment, the kit or article of manufacture comprises SLNP-PD3-TR5 and/or a therapeutically effective amount of SLNP-PD3-TR5.

In one embodiment, the kit or article of manufacture comprises SLNP-PD3-AR5 and/or a therapeutically effective amount of SLNP-PD3-AR5.

In one embodiment, the kit or article of manufacture comprises SLNP-PD3-AR5-DOX and/or a therapeutically effective amount of SLNP-PD3-AR5-DOX.

EXEMPLARY EMBODIMENTS

1) A PD-1 Prodrug composition comprising,
   (i) a drug moiety;
   (ii) a lipid moiety; and
   (iii) a linkage unit ("LU"),
   whereby the drug moiety comprises a PD-1 antagonist and whereby the LU conjugates the drug moiety with the lipid moiety.
2) The PD-1 Prodrug of claim 1, further comprising the chemical structure set forth in FORMULA I.
3) The PD-1 Prodrug of claim 1, further comprising the chemical structure set forth in FORMULA II.
4) The PD-1 Prodrug of claim 1, wherein the drug moiety comprises the chemical structure set forth as PD1.
5) The PD-1 Prodrug of claim 1, wherein the drug moiety comprises the chemical structure set forth as PD2.
6) The PD-1 Prodrug of claim 1, wherein the drug moiety comprises the chemical structure set forth as PD3.
7) The PD-1 Prodrug of claim 1, wherein the drug moiety comprises the chemical structure set forth as PD4.
8) The PD-1 Prodrug of claim 1, wherein the drug moiety comprises the chemical structure set forth as PD5.
9) The PD-1 Prodrug of claim 1, wherein the drug moiety comprises the chemical structure set forth as PD6.
10) The PD-1 Prodrug of claim 1, wherein the drug moiety comprises the chemical structure set forth as PD7.

11) The PD-1 Prodrug of claim 1, wherein the LU is an ester.
12) The PD-1 Prodrug of claim 1, wherein the LU is a thioester.
13) The PD-1 Prodrug of claim 1, wherein the lipid moiety comprises a lipid set forth in Table I.
14) The PD-1 Prodrug of claim 1, wherein the lipid moiety comprises a lipid set forth in Table III.
15) The PD-1 Prodrug of claim 1, wherein the lipid moiety comprises cholesterol.
16) The PD-1 Prodrug of claim 1, wherein the lipid moiety comprises DPPG.
17) The PD-1 Prodrug of claim 1, further comprising a helper lipid, wherein the helper lipid is set forth in Table II.
18) The PD-1 Prodrug of claim 1, wherein the drug moiety comprises the chemical structure set forth as PD3 and wherein the lipid moiety comprises cholesterol and wherein the compound has the following chemical structure:

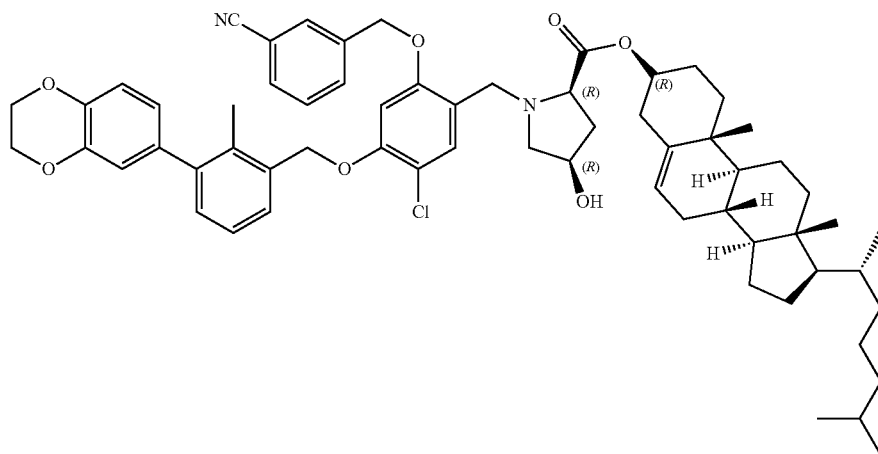

19) A PD-1 Prodrug composition comprising,
    (i) a drug moiety, whereby the drug moiety comprises PD1;
    (ii) a lipid moiety, whereby the lipid moiety comprises cholesterol; and
    (iii) LU, whereby the LU comprises an ester.
20) A PD-1 Prodrug composition comprising,
    (i) a drug moiety, whereby the drug moiety comprises PD2;
    (ii) a lipid moiety, whereby the lipid moiety comprises cholesterol; and
    (iii) LU, whereby the LU comprises an ester.
21) A PD-1 Prodrug composition comprising,
    (i) a drug moiety, whereby the drug moiety comprises PD3;
    (ii) a lipid moiety, whereby the lipid moiety comprises cholesterol; and
    (iii) a LU, whereby the LU comprises an ester.
22) A PD-1 Prodrug composition comprising,
    (i) a drug moiety, whereby the drug moiety comprises PD4;
    (ii) a lipid moiety, whereby the lipid moiety comprises cholesterol; and
    (iii) a LU, whereby the LU comprises an ester.

23) A PD-1 Prodrug composition comprising,
    (i) a drug moiety, whereby the drug moiety comprises PD5;
    (ii) a lipid moiety, whereby the lipid moiety comprises cholesterol; and
    (iii) a LU, whereby the LU comprises an ester.
24) A PD-1 Prodrug composition comprising,
    (i) a drug moiety, whereby the drug moiety comprises PD6;
    (ii) a lipid moiety, whereby the lipid moiety comprises cholesterol; and
    (iii) a LU, whereby the LU comprises an ester.
25) A PD-1 Prodrug composition comprising,
    (i) a drug moiety, whereby the drug moiety comprises PD7;
    (ii) a lipid moiety, whereby the lipid moiety comprises cholesterol; and
    (iii) a LU, whereby the LU comprises an ester.
26) A PD-1 Prodrug composition comprising,
    (i) a drug moiety, whereby the drug moiety comprises PD1;
    (ii) a lipid moiety, whereby the lipid moiety comprises DPPG; and
    (iii) a LU, whereby the LU comprises an ester.
27) A PD-1 Prodrug composition comprising,
    (i) a drug moiety, whereby the drug moiety comprises PD2;
    (ii) a lipid moiety, whereby the lipid moiety comprises DPPG; and
    (iii) a LU, whereby the LU comprises an ester.
28) A PD-1 Prodrug composition comprising,
    (i) a drug moiety, whereby the drug moiety comprises PD3;
    (ii) a lipid moiety, whereby the lipid moiety comprises DPPG; and
    (iii) a LU, whereby the LU comprises an ester.
29) A PD-1 Prodrug composition comprising,
    (i) a drug moiety, whereby the drug moiety comprises PD4;
    (ii) a lipid moiety, whereby the lipid moiety comprises DPPG; and
    (iii) a LU, whereby the LU comprises an ester.
30) A PD-1 Prodrug composition comprising,
    (i) a drug moiety, whereby the drug moiety comprises PD5;
    (ii) a lipid moiety, whereby the lipid moiety comprises DPPG; and
    (iii) a LU, whereby the LU comprises an ester.

31) A PD-1 Prodrug composition comprising,
(i) a drug moiety, whereby the drug moiety comprises PD6;
(ii) a lipid moiety, whereby the lipid moiety comprises DPPG; and
(iii) a LU, whereby the LU comprises an ester.

32) A PD-1 Prodrug composition comprising,
(i) a drug moiety, whereby the drug moiety comprises PD7;
(ii) a lipid moiety, whereby the lipid moiety comprises DPPG; and
(iii) a LU, whereby the LU comprises an ester.

33) A nanocarrier comprising, a PD-1 Prodrug whereby the liposome releases an active PD-1 inhibitor after hydrolysis of a LU.

34) The nanocarrier of claim 33, wherein the LU is an ester.

35) The nanocarrier of claim 33, further comprising a helper lipid, whereby the helper lipid is set forth in Table II.

36) The nanocarrier of claim 33, wherein the PD-1 Prodrug comprises PD1.

37) The nanocarrier of claim 33, wherein the PD-1 Prodrug comprises PD2.

38) The nanocarrier of claim 33, wherein the PD-1 Prodrug comprises PD3.

39) The nanocarrier of claim 33, wherein the PD-1 Prodrug comprises PD4.

40) The nanocarrier of claim 33, wherein the PD-1 Prodrug comprises PD5.

41) The nanocarrier of claim 33, wherein the PD-1 Prodrug comprises PD6.

42) The nanocarrier of claim 33, wherein the PD-1 Prodrug comprises PD7.

43) The nanocarrier of claim 33, wherein the PD-1 Prodrug comprises PD3.

44) The nanocarrier of claim 33, wherein the nanocarrier is a liposome.

45) The liposome of claim 44, wherein the PD-1 Prodrug comprises PD3 and is denoted LNP-PD3.

46) The nanocarrier of claim 33, whereby the nanocarrier is further co-formulated with an immune modulating agent, wherein the immune modulating agent is selected from the group consisting of immunogenic-cell death inducing chemotherapeutics, toll-receptor agonists, STING agonists, CTLA-4 inhibitors and/or prodrugs thereof.

47) The nanocarrier of claim 33, whereby the nanocarrier is further co-formulated with an ICD-inducing chemotherapeutic, wherein the ICD-inducing chemotherapeutic is selected from the group consisting of DOX, MTO, OXA, CP, Bortezomib, Carfilzimib, or Paclitaxel.

48) The liposome of claim 44, further comprising DOX.

49) The liposome of claim 44, further comprising MTO.

50) The liposome of claim 45, further comprising DOX.

51) The liposome of claim 45, further comprising MTO.

52) A kit comprising a liposome of any one of claims 33-51.

53) The nanocarrier of claim 33, wherein the nanocarrier is a solid-lipid nanoparticle (SLNP).

54) The SLNP of claim 53, wherein the PD-1 Prodrug comprises PD3 and is denoted SLNP-PD3.

55) The SLNP of claim 53, whereby the SLNP is further co-formulated with one or more immune modulating agent or a lipid-prodrug thereof, wherein the immune modulating agent is selected from the group consisting of immunogenic-cell death inducing chemotherapeutics, toll-receptor agonists, STING agonists, CTLA-4 inhibitors, IDO inhibitors, TGFβ inhibitors, CD1D agonists and/or prodrugs thereof.

56) The SLNP of claim 53, whereby the SLNP is further co-formulated with an ICD-inducing chemotherapeutic, wherein the ICD-inducing chemotherapeutic is selected from the group consisting of DOX, MTO, OXA, CP, Bortezomib, Carfilzimib, or Paclitaxel.

57) The SLNP of claim 54, further comprising DOX.

58) The SLNP of claim 54, further comprising MTO.

59) The SLNP of claim 54, whereby the liposome is further co-formulated with a toll-receptor agonist or a lipid-prodrug thereof, wherein the toll-receptor agonist is selected from the group consisting of Resiquimod (R848), Gardiquimod, 852A, DSR 6434, Telratolimod, CU-T12-9, monophosphoryl Lipid A (MPLA), 3D(6-acyl)-PHAD®, SMU127, Pam3CSK4, or 3D-PHAD®.

60) A solid lipid nanoparticle (SLNP) comprising the PD3 Prodrug of claim 54.

61) The SLNP of claim 54 co-formulated with DOX.

62) The SLNP of claim 54 co-formulated with TR5.

63) The liposome of claim 45 co-formulated with DOX.

64) The liposome of claim 45 co-formulated with NK1+.

65) A method of treating a subject suffering or diagnosed with cancer comprising,
(i) administering to a subject in need of such treatment an effective amount of a nanocarrier, wherein the nanocarrier comprises a PD-1 Prodrug; and
(ii) a pharmaceutically acceptable salt thereof.

66) The method of claim 65, wherein the PD-1 Prodrug comprises PD1.

67) The method of claim 65, wherein the PD-1 Prodrug comprises PD2.

68) The method of claim 65, wherein the PD-1 Prodrug comprises PD3.

69) The method of claim 65, wherein the PD-1 Prodrug comprises PD4.

70) The method of claim 65, wherein the PD-1 Prodrug comprises PD5.

71) The method of claim 65, wherein the PD-1 Prodrug comprises PD6.

72) The method of claim 65, wherein the PD-1 Prodrug comprises PD7.

73) The method of claim 65, wherein the nanocarrier comprises PD1 further co-formulated with and ICD-inducing chemotherapeutic.

74) The method of claim 65, wherein the nanocarrier comprises PD2 further co-formulated with and ICD-inducing chemotherapeutic.

75) The method of claim 65, wherein the nanocarrier comprises PD3 further co-formulated with and ICD-inducing chemotherapeutic.

76) The method of claim 65, wherein the nanocarrier comprises PD4 further co-formulated with and ICD-inducing chemotherapeutic.

77) The method of claim 65, wherein the nanocarrier comprises PD5 further co-formulated with and ICD-inducing chemotherapeutic.

78) The method of claim 65, wherein the nanocarrier comprises PD6 further co-formulated with and ICD-inducing chemotherapeutic.

79) The method of claim 65, wherein the nanocarrier comprises PD7 further co-formulated with and ICD-inducing chemotherapeutic.

80) The method of claim 65, wherein the nanocarrier comprises PD1 further co-formulated with an immune modulating agent.

81) The method of claim 65, wherein the nanocarrier comprises PD2 further co-formulated with an immune modulating agent.

82) The method of claim 65, wherein the nanocarrier comprises PD3 further co-formulated with an immune modulating agent.

83) The method of claim 65, wherein the nanocarrier comprises PD4 further co-formulated with an immune modulating agent.

84) The method of claim 65, wherein the nanocarrier comprises PD5 further co-formulated with an immune modulating agent.

85) The method of claim 65, wherein the nanocarrier comprises PD6 further co-formulated with an immune modulating agent.

86) The method of claim 65, wherein the nanocarrier comprises PD7 further co-formulated with an immune modulating agent.

EXAMPLES

Various aspects of the invention are further described and illustrated by way of the several examples that follow, none of which is intended to limit the scope of the invention.

Example 1: Chemical Synthesis of Protected PD3 Prodrug Comprising Cholesterol

Chemical synthesis of a protected PD3 prodrug comprising cholesterol is synthesized using the following protocol. First, Intermediate 1: (3-bromo-2-methylphenyl)methanol borane tetrahydrofuran complex is added to 3-bromo-2-methylbenzoic acid in tetrahydrofuran to yield 3-bromo-2-methylphenyl)methanol. Subsequently, Intermediate 2: (3-(2,3-dihydrobenzo[b][1,4]dioxin-6-yl)-2-methylphenyl)methanol (2,3-dihydrobenzo[b][1,4]dioxin-6-yl)boronic acid, (3-bromo-2-methylphenyl)methanol and chloro(2-dicyclohexylphosphino-2',4',6'-tri-i-propyl-1,1'-biphenyl)(2'-amino-1,1'-biphenyl-2-yl) palladium(II) (a.k.a. second generation XPhos precatalyst) is combined in Tetrahydrofuran and aqueous 0.5M potassium tribasic phosphate to yield (3-(2,3-dihydrobenzo[b][1,4]dioxin-6-yl)-2-methylphenyl)methanol. Then, Intermediate 3: 5-chloro-2,4-dihydroxybenzaldehyde 5-Chloro-2,4-dihydroxybenzaldehyde is prepared using the technique known in the art, see, VOGEL H. & GOELDNER M., et. al., *Angew. Chem. Int. Ed.* 2007, 46:19, pp. 3505-3508. Then, Intermediate 4: 5-chloro-4-((3-(2,3-dihydrobenzo[b][1,4]dioxin-(methylbenzyl)oxy)-2-hydroxybenzaldehydeDiisopropyl azodicarboxylate (0.532 mL, 2.68 mmol) in tetrahydrofuran (3 mL) is added dropwise to a cooled (0° C.) solution of 5-chloro-2,4-dihydroxybenzaldehyde treated with Diisopropyl azodicarboxylate, triphenylphosphine and (3-(2,3-dihydrobenzo[b][1,4]dioxin-6-yl)-2-methylphenyl)methanol to yield 5-chloro-4-((3-(2,3-dihydrobenzo[b][1,4]dioxin-(methylbenzyl)oxy)-2-hydroxybenzaldehyde. Then, Intermediate 5: 3-((4-chloro-5-((3-(2,3-dihydrobenzo[b][1,4]dioxin'methylbenzyl)oxy)-2-formylphenoxy)methyl)benzonitrile 5-Chloro-4-((3-(2,3-dihydrobenzo[b][1,4]dioxin-6-yl)-2-methylbenzyl)oxy)-2-hydroxybenzaldehyde is treated with cesium carbonate, then 3-cyanobenzyl bromide to yield 3-((4-chloro-5-((3-(2,3-dihydrobenzo[b][1,4]dioxin-'methylbenzyl)oxy)-2-formylphenoxy)methyl)benzonitrile. Then, Intermediate 6: 3-((4-chloro-5-((3-(2,3-dihydrobenzo[b][1,4]dioxin-6-yl)-2-methylbenzyl)oxy)-2-formylphenoxy)methyl)benzonitrile, and DTBSi protected Hydroxyproline is treated with sodium cyanoborohydride to yield Intermediate 6. Then, Intermediate 7: Intermediate 6 is treated with cholesterol and EDC to obtain the protected ester prodrug PD3. Finally, Intermediate 8: The silyl protecting group of Intermediate 7 is removed with TBAF to yield the final PD3 Prodrug. (FIGS. 1-3).

Example 2: Chemical Synthesis of Protected PD3 Prodrug Comprising DPPG

Chemical synthesis of a protected PD3 prodrug comprising DPPG is synthesized using the following protocol. First, Intermediate 1: (3-bromo-2-methylphenyl)methanol borane tetrahydrofuran complex is added to 3-bromo-2-methylbenzoic acid in tetrahydrofuran to yield 3-bromo-2-methylphenyl)methanol. Subsequently, Intermediate 2: (3-(2,3-dihydrobenzo[b][1,4]dioxin-6-yl)-2-methylphenyl)methanol (2,3-dihydrobenzo[b][1,4]dioxin-6-yl)boronic acid, (3-bromo-2-methylphenyl)methanol and chloro(2-dicyclohexylphosphino-2',4',6'-tri-i-propyl-1,1'-biphenyl)(2'-amino-1,1'-biphenyl-2-yl) palladium(II) (a.k.a. second generation XPhos precatalyst) is combined in Tetrahydrofuran and aqueous 0.5M potassium tribasic phosphate to yield (3-(2,3-dihydrobenzo[b][1,4]dioxin-6-yl)-2-methylphenyl)methanol. Then, Intermediate 3: 5-chloro-2,4-dihydroxybenzaldehyde 5-Chloro-2,4-dihydroxybenzaldehyde is prepared using the technique known in the art, see, VOGEL H. & GOELDNER M., et. al., *Angew. Chem. Int. Ed.* 2007, 46:19, pp. 3505-3508. Then, Intermediate 4: 5-chloro-4-((3-(2,3-dihydrobenzo[b][1,4]dioxin-(methylbenzyl)oxy)-2-hydroxybenzaldehydeDiisopropyl azodicarboxylate (0.532 mL, 2.68 mmol) in tetrahydrofuran (3 mL) is added dropwise to a cooled (0° C.) solution of 5-chloro-2,4-dihydroxybenzaldehyde treated with Diisopropyl azodicarboxylate, triphenylphosphine and (3-(2,3-dihydrobenzo[b][1,4]dioxin-6-yl)-2-methylphenyl)methanol to yield 5-chloro-4-((3-(2,3-dihydrobenzo[b][1,4]dioxin-(methylbenzyl)oxy)-2-hydroxybenzaldehyde. Then, Intermediate 5: 3-((4-chloro-5-((3-(2,3-dihydrobenzo[b][1,4]dioxin'methylbenzyl)oxy)-2-formylphenoxy)methyl)benzonitrile 5-Chloro-4-((3-(2,3-dihydrobenzo[b][1,4]dioxin-6-yl)-2-methylbenzyl)oxy)-2-hydroxybenzaldehyde is treated with cesium carbonate, then 3-cyanobenzyl bromide to yield 3-((4-chloro-5-((3-(2,3-dihydrobenzo[b][1,4]dioxin-'methylbenzyl)oxy)-2-formylphenoxy)methyl)benzonitrile. Then, Intermediate 6: 3-((4-chloro-5-((3-(2,3-dihydrobenzo[b][1,4]dioxin-6-yl)-2-methylbenzyl)oxy)-2-formylphenoxy)methyl)benzonitrile, and DTBSi protected Hydroxyproline is treated with sodium cyanoborohydride to yield Intermediate 6. Then, Intermediate 7: Intermediate 6 is treated with DPPG and EDC to obtain the protected ester prodrug PD3. Finally, Intermediate 8: The silyl protecting group of Intermediate 7 is removed with TBAF to yield the final PD3 Prodrug. (FIGS. 1-3).

Example 3: Chemical Synthesis of Protected PD6 Prodrug Comprising Cholesterol

Chemical synthesis of a protected PD6 prodrug comprising cholesterol is synthesized using the following protocol. First, Intermediate 1: 2,6-dichloro-3-carboxypyridine was treated with trimethylsilylethanol in THF followed by reduction with borane dimethylsulfide complex. Then, Intermediate 2: Intermediate 1 was treated with Dess-Martin Reagent. Then, Intermediate 3: 4-hydroxy-2,3-dihydro-1H-inden-2-one was treated with imidazole and tert-Butyldimethylsilyl chloride in DCM. Then, Intermediate 4: Intermediate 3 was treated with R(+)-2-methyl-CBS-oxaborolidine and borane dimethylsulfide in toluene. Then, Intermediate 5: Intermediate 4 was combined with Intermediate 2, palladium acetate, tBuXPHos, and cesium carbonate in toluene top. Then, Intermediate 6: Intermediate 5 was treated with TBAF in THF at −78° C. for 15 minutes followed by triflic anhydride, trimethylamine, and DMAP in DCM at room temperature. Then, Intermediate 7: Intermediate 6 was treated with B2Pin2, Pd-dppt and potassium acetate in dioxane. Then, Intermediate 8: Intermediate 7 was treated with 1,3-dibromo-2-chlorobenzene, Pd(dppt)Cl$_2$, and Potassium acetate. Then, Intermediate 9: Intermediate 8 was treated with Palau-CI and 20% TFA in DCM/DMF. Then, Intermediate 10: Intermediate 9 was treated with cesium fluoride in DMF at 60 C followed by methyl iodide and potassium carbonate. Then, Intermediate 11: Intermediate 10 was treated with 4,4,5,5-tetramethyl-2-(4-(4,4,5,5-tetramethyl-1,3-dioxolan-2-yl)phenyl)-1,3,2-dioxaborolane and palladium triphenylphosphine. Then, Intermediate 12: Intermediate 11 was treated with 3-azetidine carboxylic acid, potassium acetate, and triacetoxysodium borohydride. Then, Intermediate 13: The ketal in intermediate 12 was hydrolyzed to the aldehyde with HCl in dioxane, then the aldehyde was converted with s-aminomethylpyrrolidin-2-one, potassium acetate, and sodium triacetoxyborohydride. Then, Intermediate 14: Intermediate 13 was converted the BOC derivative by treatment with BOO anhydride, followed by EDC mediated esterification with cholesterol, then removal of the BOC group with HCl in dioxane to yield the final PD6 Prodrug. (FIGS. 4-7).

Example 4: Chemical Synthesis of Protected PD6 Prodrug Comprising DPPG

Chemical synthesis of a protected PD6 Prodrug comprising DPPG is synthesized using the following protocol. First, Intermediate 1: 2,6-dichloro-3-carboxypyridine was treated with trimethylsilylethanol in THF followed by reduction with borane dimethylsulfide complex. Then, Intermediate 2: Intermediate 1 was treated with Dess-Martin Reagent. Then, Intermediate 3: 4-hydroxy-2,3-dihydro-1H-inden-2-one was treated with imidazole and tert-Butyldimethylsilyl chloride in DCM. Then, Intermediate 4: Intermediate 3 was treated with R(+)-2-methyl-CBS-oxaborolidine and borane dimethylsulfide in toluene. Then, Intermediate 5: Intermediate 4 was combined with Intermediate 2, palladium acetate, tBuXPHos, and cesium carbonate in toluene top. Then, Intermediate 6: Intermediate 5 was treated with TBAF in THF at −78° C. for 15 minutes followed by triflic anhydride, trimethylamine, and DMAP in DCM at room temperature. Then, Intermediate 7: Intermediate 6 was treated with B2Pin2, Pd-dppt and potassium acetate in dioxane. Then, Intermediate 8: Intermediate 7 was treated with 1,3-dibromo-2-chlorobenzene, Pd(dppt)Cl$_2$, and Potassium acetate. Then, Intermediate 9: Intermediate 8 was treated with Palau-CI and 20% TFA in DCM/DMF. Then, Intermediate 10: Intermediate 9 was treated with cesium fluoride in DMF at 60 C followed by methyl iodide and potassium carbonate. Then, Intermediate 11: Intermediate 10 was treated with 4,4,5,5-tetramethyl-2-(4-(4,4,5,5-tetramethyl-1,3-dioxolan-2-yl)phenyl)-1,3,2-dioxaborolane and palladium triphenylphosphine. Then, Intermediate 12: Intermediate 11 was treated with 3-azetidine carboxylic acid, potassium acetate, and triacetoxysodium borohydride. Then, Intermediate 13: The ketal in intermediate 12 was hydrolyzed to the aldehyde with HCl in dioxane, then the aldehyde was converted with s-aminomethylpyrrolidin-2-one, potassium acetate, and sodium triacetoxyborohydride. Then, Intermediate 14: Intermediate 13 was converted the BOC derivative by treatment with BOC anhydride, followed by EDC mediated esterification with DPPG, then removal of the BOC group with HCl in dioxane to yield the final PD6 Prodrug. (FIGS. 4-7).

Example 5: Chemical Synthesis for Protective Group Intermediates En Route to Alternative PD3 Prodrug To synthesize the protective group intermediate for an alternative PD3 Prodrug comprising cholesterol, the following protocol was used. To a solution of compound 1 (100 g, 465 mmol, 1.00 eq) in THF (500 mL) was added BH$_3$.THF (1.00 M, 604 mL, 1.30 eq) dropwise at 10° C. over a period of two (2) hrs. After addition, the reaction mixture was stirred at 25° C. for twelve (12) hrs. The results were verified using thin layer chromatography (TLC) which showed that all compound 1 (Rt=0.5) was consumed and a new spot (R$_f$=0.9) was detected. Then, MeOH (500 mL) was added dropwise to the reaction mixture at 0° C. Then, the reaction mixture was stirred at 25° C. for twelve (12) hrs. and concentrated to give the crude compound 2. The crude compound 2 was dissolved in ethyl acetate (1.00 L) and was washed with 1 N HCl (1.00 L), brine (200 mL). The organic layer was dried over Na$_2$SO$_4$ and concentrated. The crude compound 2 was used for next synthesis step directly without further purification. The compound 2 (90.0 g, 447 mmol, 96.3% yield) was obtained as a white solid. The resulting compound is set forth in FIG. 11.

Then, to a solution of compound 2 (79.6 g, 442 mmol, 1.00 eq) and K$_3$PO$_4$ (1.82 M, 851 mL, 3.50 eq) in THF (500 mL) was added Pd(dppf)Cl$_2$ (9.72 g, 13.2 mmol, 0.03 eq) under N$_2$. The mixture was stirred at 25° C. for two (2) hrs. The results were verified by TLC which showed that all compound 2 (R$_f$=0.6) was consumed and a new spot (R$_f$=0.4) was detected. The mixture was poured into H$_2$O (500 mL) and extracted with ethyl acetate (400 mL*3). The combined organic layers were washed with brine (200 mL), dried over Na$_2$SO$_4$, and concentrated. The crude compound 4 was purified by column chromatography (SiO$_2$, petroleum ether/ethyl acetate=30/1 to 5/1) (R$_f$=0.4). The compound 4 (95.0 g, 365 mmol, 82.5% yield, 98.5% purity) was obtained as a light-yellow. The resulting compound is set forth in FIG. 11.

Example 6: Chemical Synthesis for Protective Group Intermediates En Route to Alternative PD3 Prodrug To synthesize the protective group intermediate for an alternative PD3 Prodrug comprising cholesterol, the following protocol was used. To a solution of compound 4 (61.0 g, 234 mmol, 1.00 eq), compound 5 (44.5 g, 257 mmol, 1.10 eq) and PPh$_3$ (67.6 g, 257 mmol, 1.10 eq) in THF (700 mL) was added dropwise DIAD (52.1 g, 257 mmol, 50.1 mL, 1.10 eq) in THF (335 mL) at −20° C. under N$_2$. The mixture was stirred at −10° C. for one (1) hr. Then, the mixture was stirred at 25° C. for 10 hrs. LCMS confirmed that all compound 4 was consumed and 31.0% desired MS (RT=1.148 mins) was detected. The mixture was filtered to get the cake and was washed with ethyl acetate (300 mL). The cake was concentrated to get the crude compound 6. The crude compound 6 was used in the subsequent step directly.

The compound 6 (40.0 g, 97.3 mmol, 41.5% yield) was obtained as a white solid. The resulting compound is set forth in FIG. 12.

Then, to a solution of compound 6 (20.0 g, 48.7 mmol, 1.00 eq) and $Cs_2CO_3$ (20.0 g, 61.3 mmol, 1.26 eq) in DMF (320 mL) was stirred at 25° C. for 0.5 hr. Then compound 7 (10.5 g, 53.6 mmol, 1.10 eq) was added to the solution and the mixture was stirred at 25° C. for twelve (12) hrs. TLC (petroleum ether/ethyl acetate=3/1) showed compound 6 ($R_f$=0.7) was consumed completely and a main spot ($R_f$=0.1) was detected. The mixture was poured into ice-water (1.00 L) and ethyl acetate (4.00 L). The organic phase was washed with brine (1.00 L*3), dried over $Na_2SO_4$, filtered, and concentrated to give the crude product. The crude product was purified by slurrying with ethyl acetate (200 mL) at 25° C. for sixteen (16) hrs. and filtered to collect the solid. The compound 8 (25.0 g, 47.5 mmol, 97.6% yield) was obtained as a white solid. The resulting compound is set forth in FIG. 12.

Example 7: Chemical Synthesis for Protective Group Intermediates En Route to Alternative PD3 Prodrug To synthesize the protective group intermediate for an alternative PD3 Prodrug comprising cholesterol, the following protocol was used. To a solution of compound 9_1 (50.0 g, 381 mmol, 1.00 eq) in ACN (500 mL) was added TBDMSCl (201 g, 1.33 mol, 164 mL, 3.50 eq) and DBU (218 g, 1.43 mol, 216 mL, 3.76 eq) at 0° C. The mixture was stirred at 25° C. for twenty-four (24) hrs. TLC (DCM/MeOH=5/1) showed compound 9_1 ($R_f$=0) was consumed completely, and a main spot ($R_f$=0.1) was detected. The mixture was concentrated to give the crude product. The crude product was poured into MeOH (200 mL), THF (100 mL), $H_2O$ (100 mL) and 2 N NaOH (150 mL). The mixture was stirred at 25° C. for sixteen (16) hrs. The mixture was filtered to collect the solid. The compound 9 (36.0 g, 147 mmol, 38.5% yield) was obtained as a white solid. The resulting compound is set forth in FIG. 13.

Then, to a solution of compound 8 (5.00 g, 9.51 mmol, 1.00 eq) in DMF (90.0 mL) was added compound 9 (3.50 g, 14.3 mmol, 1.50 eq), AcOH (571 mg, 9.51 mmol, 544 uL, 1.00 eq) and MeOH (22.5 mL). Then to the mixture was added $NaBH_3CN$ (1.49 g, 23.8 mmol, 2.50 eq). The mixture was stirred at 25° C. for 0.5 hr. LCMS showed compound 8 was consumed completely and the desired MS (RT=0.958 min) was detected. The mixture was poured into $H_2O$ (200 mL) and extracted with ethyl acetate (800 mL*3). Combined organics were washed with brine (800 mL), dried over $Na_2SO_4$, filtered, and concentrated to give the crude product. The crude product was purified by prep-HPLC (TFA condition). The compound 10 (4.00 g, 4.94 mmol, 52.0% yield, 93.3% purity) was obtained as a yellow solid. The resulting compound is set forth in FIG. 13.

Example 8: Chemical Synthesis of Alternative PD3 Prodrug Comprising Cholesterol

Chemical synthesis of a PD3 Prodrug comprising cholesterol is synthesized in the following manner. Briefly, a mixture of compound 10 (8.50 g, 11.3 mmol, 1.00 eq), compound 10_1 (8.70 g, 22.5 mmol, 5.88 mL, 2.00 eq), DMAP (2.06 g, 16.9 mmol, 1.50 eq) and DCC (3.48 g, 16.9 mmol, 3.41 mL, 1.50 eq) in DCM (160 mL) was stirred at 25° C. for sixteen (16) hrs. LCMS confirmed compound 10 was consumed completely and the desired MS (RT=1.275 mins) was detected. The mixture was concentrated to give the crude product. The crude product was purified by column chromatography ($Al_2O_3$, ethyl acetate/Petroleum ether=1/20 to 1/8) to give the product (petroleum ether/ethyl acetate=3/1, $R_f$=0.7). The compound 11 (3.60 g, 3.14 mmol, 27.9% yield, 98.1% purity) was obtained as a white solid. The resulting compound is set forth in FIG. 14.

Then, to a solution of compound 11 (3.70 g, 3.29 mmol, 1.00 eq) in THF (40.0 mL) was added TBAF (1.00 M, 6.58 mL, 2.00 eq). The mixture was stirred at 20° C. for two (2) hrs. LCMS showed compound 11 was consumed completely and the desired MS (RT=1.183 mins) was detected. The mixture was concentrated to give the crude product. The crude product was purified by column chromatography ($Al_2O_3$, ethyl acetate/petroleum ether=0/1 to 1/3) to give the product (petroleum ether/ethyl acetate=1/1, $R_f$=0.4). The resulting compound and synthesis is set forth in FIG. 14. The synthesis set forth in this example yields a PD3 Prodrug comprising cholesterol with the following chemical structure (set forth below as Target 1):

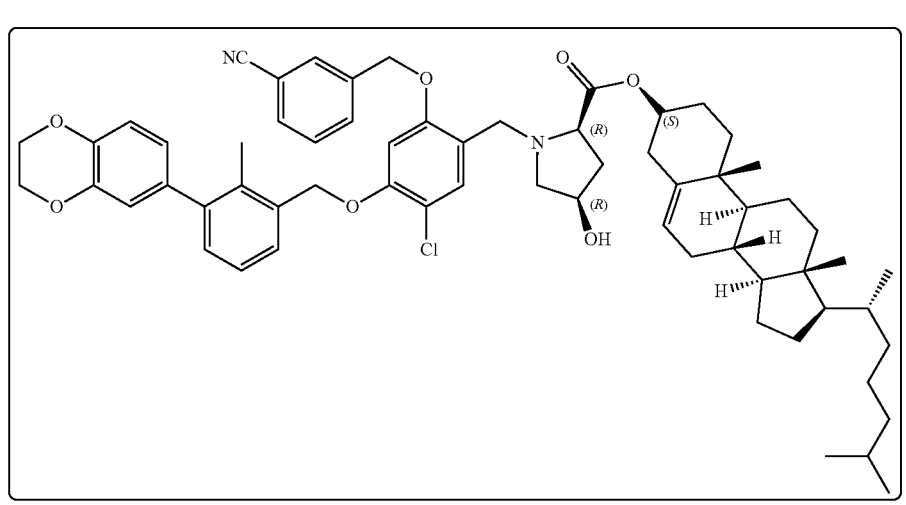

Target 1

Example 9: Synthesis and Characterization of LNP-TB4 Liposome

In another experiment, a liposome comprising the PD3 Prodrug (denoted LNP-PD3) was synthesized in the following manner. Briefly, In the first step, a lipid stock solution of HSPC, CHOl, and DSPE-PEG, was prepared in ethanol (20 mg/ml) separately. PD3 Prodrug (Target 1) stock solution was prepared in acetonitrile (20 mg/ml) as it was not soluble in ethanol. The of lipid mixture of HSPC, CHOL, PD3 Prodrug (Target 1), and DSPE-PEG was mixed together at a molar ratio of 51:24:21:5, was prepared mixing all the lipid stock solution in appropriate amount and then further diluting with ethanol (to get a lipid concentration of 10 mg/ml). This lipid mixture was preheated at 50 degrees Centigrade using the heating block attachment in the microfluidizer. Similarly, the aqueous phase containing 1 mM PBS buffer was also preheated at 50 degrees centigrade before passing through the microfluidics cartridge at the flow rate of 3:1 (aqueous: organic phase, lipid mixture). The solvent was removed using dialysis membrane of cut off 12 KDa size (Sigma Aldrich) against DI water for at least 24 hrs. The bulk dialysis water was changed at least 5 times during the period of 24 hrs. to maximize the removal of the solvent. After the removal of the solvent, the LNP-PD3 was concentrated according to the need using Amicon centrifugal filtration device (cut off size 10 KDa, at 3000 g).

Characterization of the LNP-PD3 liposome was determined using a Malvern Zetasizer (Malvern Instrumentation Co., Westborough, MA, USA). Briefly, two (2) ml of LNP-PD3 liposomes (concentration of the liposome was of 0.5-1 mg/ml) was placed in a 4-sided, clear, plastic cuvette and analyzed directly at 25° C. The results shown in FIG. 15 show the Zav size of the nanoparticles were approximately 81 nm with a PDI of approximately 0.218.

Additionally, Zeta potential of the LNP-PD3 liposomes in aqueous dispersion was determined using a Malvern zeta seizer Instrument (Malvern Instrumentation Co, Westborough, MA, USA). Briefly, approximately one (1) ml of the liposome (concentration approximately 2 mg/ml in 20 mM NaCl) was placed in a disposable capillary zeta potential cell available for the Zetasizer. The measurement was done at 25° C. The results show the Zeta potential determination of LNP-PD3 was approximately −10.2 mV (FIG. 16).

Example 10: Synthesis and Characterization of SLNP-PD3-TR5 Solid-Lipid Nanoparticle In another experiment, a solid-lipid nanoparticle (SLNP) comprising the PD3 Prodrug (denoted SLNP-PD3-TR5) was synthesized in the following manner. Briefly, SLNPs were prepared by a solvent diffusion method using different types of stabilizers. For example, Polyvinyl alcohol (e.g., Moliwol 488), poloxamers (e.g., Pluronic F-68, Pluronic F-127), Tween 80 & 20, Kolliphor RH40, etc. can be used as stabilizer(s). In the first step, a lipid stock solution of DSPC, CHOL, DSPE-PEG-COOH and a Toll-Like Receptor agonist (denoted TR5) was prepared in ethanol (20 mg/ml). Separately, PD3 Prodrug (Target 1) stock solution was prepared in DMSO (20 mg/ml). The lipid mixture of DSPC, CHOL, PD3 Prodrug, TR5, and DSPE-PEG-COOH was mixed together at a molar ratio of 25:38:26:6:5 (with a lipid concentration of 20 mg/ml). This lipid mixture was heated at 50 degree C. for few minutes. Similarly, the aqueous phase containing the appropriate stabilizer (e.g., 2-5% w/v Pluronic F127) was heated using a hot plate, with constant magnetic stirring (at 300-400 rpm). The lipid mixture was slowly mixed with this aqueous phase under constant magnetic stirring. Once the mixing was completed, the entire mixture was sonicated using a water sonicator bath for about five (5) minutes and then again kept back in the magnetic stirrer plate with constant stirring for about another one (1) hour. Finally, the solvent was removed using dialysis membrane of cut off 12 KDa size (Sigma Aldrich) against DI water for at least eight (8) hrs. Finally, the SLNP-PD3-TR5 was concentrated according to the need using Amicon centrifugal filtration device (cut off size 10 KDa, at 3000 g).

Characterization of the SLNP-PD3-TR5 was determined using a Malvern Zetasizer (Malvern Instrumentation Co., Westborough, MA, USA). Briefly, two (2) ml of SLNP-PD3-TR5 (concentration of the SLNP was of 0.5-1 mg/ml) was placed in a 4-sided, clear, plastic cuvette and analyzed directly at 25° C. The results shown in FIG. 17 show the Zav size of the nanoparticles were approximately 106 nm with a PDI of approximately 0.132.

Additionally, Zeta potential of the SLNP-PD3-TR5 solid-lipid nanoparticle in aqueous dispersion was determined using a Malvern zeta seizer Instrument (Malvern Instrumentation Co, Westborough, MA, USA). Briefly, approximately one (1) ml of the SLNP (concentration approximately 2 mg/ml in 20 mM NaCl) was placed in a disposable capillary zeta potential cell available for the Zetasizer. The measurement was done at 25° C. The results show the Zeta potential determination of SLNP-PD3-TR5 was approximately −11.2 mV (FIG. 18).

Example 11: Synthesis and Characterization of SLNP-PD3-AR5-DOX Solid-Lipid Nanoparticle In another experiment, a solid-lipid nanoparticle (SLNP) comprising the PD3 Prodrug encapsulating doxorubicin (denoted SLNP-PD3-AR5-DOX) was synthesized in the following manner. Briefly, SLNPs in this example, were prepared by a solvent diffusion method using Pluronic F-127 as a stabilizer. However, for example, Polyvinyl alcohol (e.g., Moliwol 488), poloxamers (e.g., Pluronic F-68), Tween 80 & 20, Kolliphor RH40, etc. can also be used as stabilizer(s). In the first step, lipid stock solution of DSPC, CHOL, DSPE-PEG-COOH was prepared in ethanol (20 mg/ml). Separately, stock solution of an AR5 Prodrug and PD3 Prodrug (Target 1) were prepared in DMSO (20 mg/ml). DSPC, CHOL, PD3 Prodrug, AR5 prodrug, and DSPE-PEG was mixed together at a molar ratio of 25:38:18:14:5 to obtain a lipid mixture with a lipid concentration of 20 mg/ml.

This lipid mixture was heated to 50 degree C. and subsequently, to this mixture 4.7 mg of Doxorubicin was added and dissolved by vertexing for about five (5) minutes. The aqueous phase containing Pluronic F127 (2% w/v) was heated using a magnetic hot plate stirrer with constant magnetic stirring (300-400 rpm). The above lipid mixture with doxorubicin was slowly added to this aqueous phase (Pluronic F127) under constant stirring for thirty (30) minutes. Once the mixing was completed, the entire mixture was sonicate using a water bath sonicator for about ten (10) minutes. Finally, the solvent was removed using dialysis membrane of cut off 12 KDa size (Sigma Aldrich) against. DI water was used as a bulk medium for dialysis and the dialysis was performed for at least eight (8) hrs. During the period of dialysis bulk DI water was changed at least for 3 times (3×). Finally, the SLNP-AR5-PD3-Dox was concentrated according to the need using Amicon centrifugal filtration device (cut off size 10 KDa, at 3000 g).

Characterization of the SLNP-PD3-AR5-DOX was determined using a Malvern Zetasizer (Malvern Instrumentation Co., Westborough, MA, USA). Briefly, two (2) ml of SLNP-PD3-AR5-DOX (concentration of the SLNP was of 0.5-1 mg/ml) was placed in a 4-sided, clear, plastic cuvette and analyzed directly at 25° C. The results shown in FIG. 19 show the Zav size of the nanoparticles were approximately 101.7 nm with a PDI of approximately 0.158.

Additionally, Zeta potential of the SLNP-PD3-TR5 solid-lipid nanoparticle in aqueous dispersion was determined using a Malvern zeta seizer Instrument (Malvern Instrumentation Co, Westborough, MA, USA). Briefly, approximately one (1) ml of the SLNP (concentration approximately 2 mg/ml in 20 mM NaCl) was placed in a disposable capillary zeta potential cell available for the Zetasizer. The measurement was done at 25° C. The results show the Zeta potential determination of SLNP-PD3-AR5-DOX was approximately −10.5 mV (FIG. 20).

Example 12: Tumor Inhibition of LNP-PD3 in Multiple Combination(s) Using EMT6 Cells In Vivo In this experiment, evaluation of LNP-PD3 in multiple combination(s) was performed using the following protocols. Briefly, murine breast cancer EMT6 cells (cells (0.5× $10^6$) were inoculated subcutaneously in the right rear flank region of Balb/c mice. Animals were treated with vehicle control, LNP-DOX (Doxorubicin in liposome form) at 3 mg/kg, anti-PD1 antibody at 10 mg/kg, LNP-PD3 at 3 mg/kg, and a combination of LNP-DOX and LNP-PD3 at 3 mg/kg. After receiving two doses of LNP-DOX, the LNP-DOX treatment was replaced with vehicle. Tumor volumes were measured three (3) times in two dimensions using a caliper, and the volume was calculated using the formula: $V=(L \times W \times W) \times 0.5$, where V is tumor volume, L is tumor length (the longest tumor dimension), and W is tumor width (the longest tumor dimension perpendicular to L). The tumor growth inhibition (TGI) was calculated based on the tumor size data of day 21.

The results show that treatment of LNP-DOX alone or in combination with LNP-PD3 produces significant anti-tumor activity, the TGI was calculated at 68.74% and at 67.9%, ($p<0.05$). (FIG. 21).

Example 13: Tumor Inhibition of SLNP-PD3-TR5 Using EMT6 Cells In Vivo

In this experiment, evaluation of SLNP-PD3-TR5 was performed using the following protocols. Briefly, murine breast cancer EMT6 cells (cells (0.1×$10^6$) were inoculated subcutaneously in the right rear flank region of Balb/c mice. Animals were treated with vehicle control, TR5 (Toll-Like Receptor 7/8 agonist in liposome form) at 1 mg/kg, and SLNP-PD3-TR5 (Combination of TR5 at 1 mg/kg and Cholesterol at 5 mg/kg in liposome form). Tumor volumes were measured three (3) times in two dimensions using a caliper, and the volume was calculated using the formula: $V=(L \times W \times W) \times 0.5$, where V is tumor volume, L is tumor length (the longest tumor dimension), and W is tumor width (the longest tumor dimension perpendicular to L). The tumor growth inhibition (TGI) was calculated based on the tumor size data of day 21.

The results show, treatment with SLNP-PD3-TR5 and SLNP-TR5 produce significant anti-tumor activity when compared to the vehicle. The TGI was calculated at 74.72% and at 83.13%, ($p<0.05$). (FIG. 22).

Example 14: Tumor Inhibition of LNP-PD3 In Combination with LNP-ID3-NK1 Using B16F10 Cells In Vivo In this experiment, evaluation of LNP-PD3 in multiple combinations was performed using the following protocols. Briefly, murine melanoma cancer B16F10 cells (cells (0.2× $10^6$) were inoculated subcutaneously in the right rear flank region of C57BL/6 mice. Animals were treated with vehicle control, LNP-ID3-NK1 (ID3 at 3 mg/kg and NK1 at 0.3 mg/kg in liposome form), and combination of LNP-ID3-NK1 and LNP-PD3 two times weekly through iv injection. Tumor volumes were measured three (3) times in two dimensions using a caliper, and the volume was calculated using the formula: $V=(L \times W \times W) \times 0.5$, where V is tumor volume, L is tumor length (the longest tumor dimension), and W is tumor width (the longest tumor dimension perpendicular to L). The tumor growth inhibition (TGI) was calculated based on the tumor size data of day 18.

The results show that treatment with LNP-PD3 in combination with LNP-ID3-NK1 as well as LNP-ID3-NK1 produce a significant tumor growth inhibition, when compared to vehicle treated group. TGIs were calculated at 44.01%% and 54.31% ($p<0.01$). (FIG. 23).

Example 15: Human Clinical Trials for the Treatment of Human Carcinomas Through the Use of Formulated and/or Co-Formulated Nanocarriers Comprising PD-1 Prodrugs Formulated and/or co-formulated nanocarriers containing PD-1 Prodrugs are used in accordance with the present invention which specifically accumulate in a tumor cell and are used in the treatment of certain tumors and other immunological disorders and/or other diseases. In connection with each of these indications, two clinical approaches are successfully pursued.

I.) Adjunctive therapy: In adjunctive therapy, patients are treated with formulated and/or co-formulated nanocarriers containing PD-1 Prodrugs in combination with a chemotherapeutic or pharmaceutical or biopharmaceutical agent or a combination thereof. Primary cancer targets are treated under standard protocols by the addition of formulated and/or co-formulated nanocarriers containing PD-1 Prodrugs. Protocol designs address effectiveness as assessed by the following examples, including but not limited to, reduction in tumor mass of primary or metastatic lesions, increased progression free survival, overall survival, improvement of patient's health, disease stabilization, as well as the ability to reduce usual doses of standard chemotherapy and other biologic agents. These dosage reductions allow additional and/or prolonged therapy by reducing dose-related toxicity of the chemotherapeutic or biologic agent.

II.) Monotherapy: In connection with the use of the formulated and/or co-formulated nanocarriers containing PD-1 Prodrugs in monotherapy of tumors, the formulated and/or co-formulated nanocarriers containing PD-1 Prodrugs are administered to patients without a chemotherapeutic or pharmaceutical or biological agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patient's health, disease stabilization, as well as the ability to reduce usual doses of standard chemotherapy and other biologic agents.

Dosage

Dosage regimens may be adjusted to provide the optimum desired response. For example, a single formulated and/or co-formulated nanocarrier containing PD-1 Prodrugs may be administered, several divided doses may be administered over time, or the dose may be proportionally reduced or increased as indicated by the exigencies of the therapeutic situation. "Dosage Unit Form" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the formulated and/or co-formulated nanocarriers containing PD-1 Prodrugs, (b) the individual mechanics of the combination compound, if any, (c) the particular therapeutic or prophylactic effect to be achieved, and (d) the limitations inherent in the art of compounding such an compound for the treatment of sensitivity in individuals.

Clinical Development Plan (CDP)

The CDP follows and develops treatments of using formulated and/or co-formulated nanocarriers containing PD-1 Prodrugs in connection with adjunctive therapy or monotherapy. Trials initially demonstrate safety and thereafter confirm efficacy in repeat doses. Trials are open label comparing standard chemotherapy and/or the current standard of therapy plus formulated and/or co-formulated nanocarriers containing PD-1 Prodrugs. As will be appreciated, one non-limiting criteria that can be utilized in connection with enrollment of patients is expression of PD-1-L1/L2 in a tumor as determined by standard detection methods known in the art.

It is believed that formulated and/or co-formulated nanocarriers, or any of the embodiments disclosed herein, may possess satisfactory pharmacological profile and promising biopharmaceutical properties, such as toxicological profile, metabolism and pharmacokinetic properties, solubility, and permeability. It will be understood that determination of appropriate biopharmaceutical properties is within the knowledge of a person skilled in the art, e.g., determination of cytotoxicity in cells or inhibition of certain targets or channels to determine potential toxicity.

The present invention is not to be limited in scope by the embodiments disclosed herein, which are intended as single illustrations of individual aspects of the invention, and any that are functionally equivalent are within the scope of the invention. Various modifications to the models, methods, and life cycle methodology of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE I

Examples of Lipids.

| No. | Abbreviation | Name/Chemical Formula |
|---|---|---|
| 1 | CHOL | Cholesterol |
| 2 | DPPG•Na | 1,2-dipalmitoyl-sn-glycero-3-phospho-(1'-rac-glycerol) (sodium salt) |

TABLE I-continued

Examples of Lipids.

| No. | Abbreviation | Name/Chemical Formula |
|---|---|---|
| 3 | DMPG•Na | 1,2-dimyristoyl-sn-glycero-3-phospho-(1'-rac-glycerol) (sodium salt) |
| 4 | Lyso PC | 1-decanoyl-2-hydroxy-sn-glycero-3-phosphocholine |
| 5 | (Δ9-Cis) PG | 1,2-dioleoyl-sn-glycero-3-phospho-(1'-rac-glycerol) (sodium salt) |
| 6 | Soy Lyso PC | L-α-lysophosphatidylcholine (Soy) |
| 7 | PG | 1,2-dilauroyl-sn-glycero-3-phospho-(1'-rac-glycerol) (sodium salt) |
| 8 | PA-PEG3-mannose | 1,2-dipalmitoyl-sn-glycero-3-phospho((ethyl-1',2',3'-triazole)triethyleneglycolmannose) (ammonium salt) |
| 9 | C16 PEG2000 Ceramide | N-palmitoyl-sphingosine-1-{succinyl[methoxy(polyethylene glycol)2000]} |
| 10 | MPLA | Monophosphoryl Lipid A |

TABLE II

Examples of Helper Lipids.

| No. | Abbreviation | Name |
|---|---|---|
| 1 | DOTAP | 1,2-dioleoyl-3-trimethylammonium-propane (chloride salt) |
| 2 | DODMA | 1,2-dioleyloxy-3-dimethylaminopropane |
| 3 | DLinDMA | 1,2-dilinoleyloxy-3-dimethylaminopropane |
| 4 | DLin-KC2-DMA | 2,2-dilinoleyl-4-dimethylaminoethyl-[1,3]-dioxolane |
| 5 | Δ9-Cis PE (DOPE) | 1,2-Dioleoyl-sn-glycero-3-phosphoethanolamine |
| 6 | DOPC | 1,2-dioleoyl-sn-glycero-3-phosphocholine |
| 7 | CHOL | Cholesterol |
| 8 | PEG-C-DMA | N-[(methoxy poly(ethylene glycol)2000)carbamyl]-1,2-dimyristyloxlpropyl-3-amine |
| 9 | CHEMS | cholesteryl hemisuccinate |
| 10 | DPPC | 1,2-dipalmitoyl-sn-glycero-3-phosphocholine |
| 11 | DSPC | 1,2-distearoyl-sn-glycero-3-phosphocholine |
| 12 | MO-CHOL | 4-(2-aminoethyl)-morpholino-cholesterolhemisuccinate |
| 13 | DSPE-PEG(2000) Carboxylic Acid | (1,2-distearoyl-sn-glycero-3-phosphoethanolamine-N-[carboxy(polyethylene glycol) |
| 14 | Hydro Soy PC ("HSPC") | L-α-phosphatidylcholine, hydrogenated (Soy) powder |

TABLE III

Examples of Phospholipids/Fatty Acids.

| No. | Name |
|---|---|
| 1 | Oleic acid |
| 2 | linolenic acid |
| 3 | arachidonic acid |
| 4 | docosahexaenoic (DHA) |
| 5 | Palmitic acid |
| 6 | Palmitoleic acid |
| 7 | Stearic acid |
| 8 | Eicosapentaenoic acid (EPA) |
| 9 | DSPE-PEG(2000) Carboxylic Acid (1,2-distearoyl-sn-glycero-3-phosphoethanolamine-N-[carboxy(polyethylene glycol) |
| 10 | DOPE-PEG(2000) Carboxylic acid (1,2-dioleoyl-sn-glycero-3-phosphoethanolamine-N-[carboxy(polyethylene glycol)-2000] (sodium salt) |

The invention claimed is:

1. A PD-1 Prodrug composition comprising,
   (i) a drug moiety;
   (ii) a lipid moiety; and
   (iii) a linkage unit ("LU"), whereby the drug moiety comprises a PD-1 antagonist and whereby the LU conjugates the drug moiety with the lipid moiety, and wherein the PD-1 Prodrug composition has the following chemical structure:

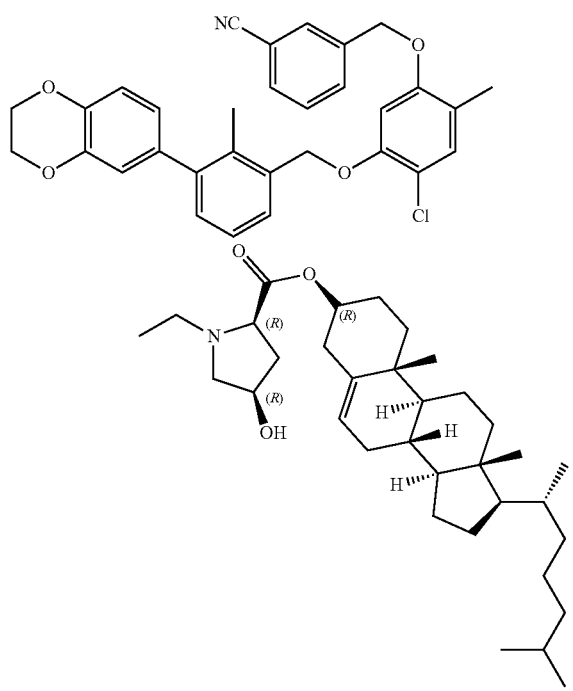

2. The PD-1 Prodrug composition of claim 1, wherein the drug moiety comprises the chemical structure set forth as PD3.

3. The PD-1 Prodrug composition of claim 1, wherein the lipid moiety comprises cholesterol.

4. A nanocarrier comprising, a PD-1 Prodrug whereby the nanocarrier releases an active PD-1 inhibitor after cleavage of a LU, and wherein the PD-1 Prodrug composition has the following chemical structure:

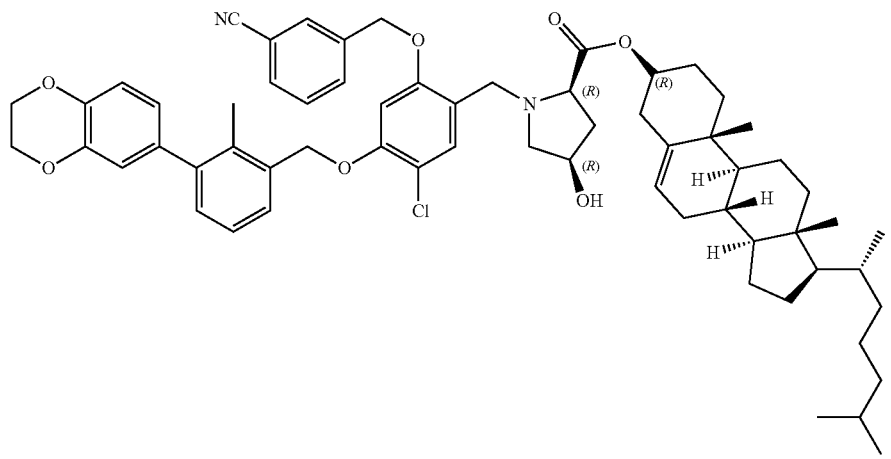

5. The nanocarrier of claim 4, further comprising a helper lipid, whereby the helper lipid is set forth in the follow table:

| No. | Abbreviation | Name |
| --- | --- | --- |
| 1 | DOTAP | 1,2-dioleoyl-3-trimethylammonium-propane (chloride salt) |
| 2 | DODMA | 1,2-dioleyloxy-3-dimethylaminopropane |
| 3 | DLinDMA | 1,2-dilinoleyloxy-3-dimethylaminopropane |
| 4 | DLin-KC2-DMA | 2,2-dilinoleyl-4-dimethylaminoethyl-[1,3]-dioxolane |
| 5 | A9-CIS PE (DOPE) | 1,2-Dioleoyl-sn-glycero-3-phosphoethanolamine |
| 6 | DOPC | 1,2-dioleoyl-sn-glycero-3-phosphocholine |
| 7 | CHOL | Cholesterol |
| 8 | PEG-C-DMA | N-[(methoxy poly(ethylene glycol)2000)carbamyl]-1,2-dimyristyloxlpropyl-3-amine |
| 9 | CHEMS | cholesteryl hemisuccinate |
| 10 | DPPC | 1,2-dipalmitoyl-sn-glycero-3-phosphocholine |
| 11 | DSPC | 1,2-distearoyl-sn-glycero-3-phosphocholine |
| 12 | MO-CHOL | 4-(2-aminoethyl)-morpholino-cholesterolhemisuccinate |
| 13 | DSPE-PEG(2000) Carboxylic Acid | (1,2-distearoyl-sn-glycero-3-phosphoethanolamine-N-[carboxy(polyethylene glycol)] |
| 14 | Hydro Soy PC ("HSPC") | L-a-phosphatidylcholine, hydrogenated (Soy) powder |

6. The nanocarrier of claim 4, wherein the PD-1 Prodrug comprises PD3.

7. The nanocarrier of claim 4, wherein the PD-1 Prodrug comprises PD3 and further comprises cholesterol.

8. The nanocarrier of claim 4, whereby the nanocarrier is further co-formulated with one or more immune modulating agent or a lipid-prodrug thereof, wherein the immune modulating agent is selected from the group consisting of immunogenic-cell death inducing chemotherapeutics, toll-receptor agonists, STING agonists, CTLA-4 inhibitors, IDO inhibitors, TGFβ inhibitors, CD1D agonists and/or prodrugs thereof.

9. The nanocarrier of claim 4, whereby the nanocarrier is further co-formulated with an ICD-inducing chemotherapeutic, wherein the ICD-inducing chemotherapeutic is selected from the group consisting of DOX, MTO, OXA, CP, Bortezomib, Carfilzimib, or Paclitaxel.

10. The nanocarrier of claim 4, whereby the nanocarrier is further co-formulated with a toll-receptor agonist or a lipid-prodrug thereof, wherein the toll-receptor agonist is selected from the group consisting of Resiquimod (R848), Gardiquimod, 852A, DSR 6434, Telratolimod, CU-T12-9, monophosphoryl Lipid A (MPLA), 3D(6-acyl)-PHAD®, SMU127, or Pam3CSK4.

11. The nanocarrier of claim 4, wherein the nanocarrier comprises a liposome.

12. The nanocarrier of claim 11, wherein the liposome is LNP-PD3.

13. The nanocarrier of claim 4, wherein the nanocarrier comprises a solid-lipid nanoparticle (SLNP).

14. The SLNP nanocarrier of claim 13, wherein the SLNP is SLNP-PD3.

15. A method of treating a subject diagnosed with cancer comprising,
    (i) administering to a subject in need of such treatment an effective amount of a nanocarrier, wherein the nanocarrier comprises a PD-1 Prodrug, and wherein PD-1 Prodrug has the following chemical structure:

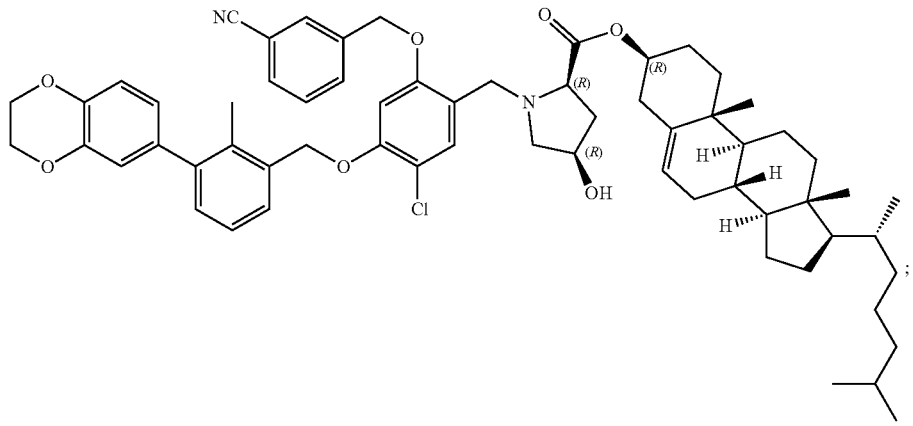

and
    (ii) a pharmaceutically acceptable salt thereof.

* * * * *